(12) United States Patent
Chen et al.

(10) Patent No.: US 7,119,102 B2
(45) Date of Patent: Oct. 10, 2006

(54) SUBSTITUTED 3-AMINO-THIENO[2,3-B]PYRIDINE-2-CARBOXYLIC ACID AMIDE COMPOUNDS AND PROCESSES FOR PREPARING AND THEIR USES

(75) Inventors: Zhidong Chen, New Milford, CT (US); Pier Francesco Cirillo, Woodbury, CT (US); Darren DiSalvo, New Milford, CT (US); Weimin Liu, Sandy Hook, CT (US); Daniel Richard Marshall, Sandy Hook, CT (US); Lifen Wu, New Milford, CT (US); Erick Richard Roush Young, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 132 days.

(21) Appl. No.: 11/002,828

(22) Filed: Dec. 2, 2004

(65) Prior Publication Data

US 2005/0182053 A1 Aug. 18, 2005

Related U.S. Application Data

(60) Provisional application No. 60/527,522, filed on Dec. 5, 2003.

(51) Int. Cl.
| | |
|---|---|
| A61K 31/4365 | (2006.01) |
| A61K 31/506 | (2006.01) |
| A61K 31/5377 | (2006.01) |
| C07D 413/14 | (2006.01) |
| C07D 409/14 | (2006.01) |

(52) U.S. Cl. .................. 514/301; 514/233.8; 514/256; 514/274; 544/111; 544/300; 544/333; 546/114

(58) Field of Classification Search .............. 546/114; 544/111, 300, 333
See application file for complete search history.

(56) References Cited

U.S. PATENT DOCUMENTS

2004/0053957 A1 3/2004 Cywin et al.

2004/0180922 A1 9/2004 Cywin et al.
2005/0038104 A1 2/2005 Chen et al.

FOREIGN PATENT DOCUMENTS

| WO | WO 03/037886 | 5/2003 |
|---|---|---|
| WO | WO 03/103661 | 12/2003 |

OTHER PUBLICATIONS

Karin et al. Nature Reviews Drug Discovery, 2004, 3, 17-26.*

* cited by examiner

Primary Examiner—Kamal A. Saeed
Assistant Examiner—Jason M. Nolan
(74) Attorney, Agent, or Firm—Michael Morris; Mary-Ellen M. Devlin; David Dow

(57) ABSTRACT

Disclosed are compounds of formula (I):

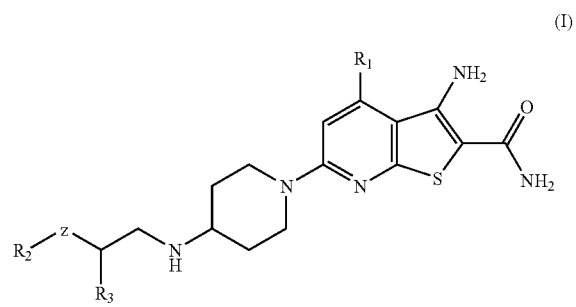

wherein the variables $R_1$, $R_2$, $R_3$ and Z are described herein, which are useful as inhibitors of the kinase activity of the IκB kinase (IKK) complex. The compounds are therefore useful in the treatment of IKK mediated diseases including autoimmune diseases inflammatory diseases and cancer. Also disclosed are pharmaceutical compositions comprising these compounds and processes for preparing these compounds.

13 Claims, No Drawings

SUBSTITUTED 3-AMINO-THIENO[2,3-B]PYRIDINE-2-CARBOXYLIC ACID AMIDE COMPOUNDS AND PROCESSES FOR PREPARING AND THEIR USES

RELATED APPLICATIONS

This application claims priority to U.S. provisional application No. 60/527,522 filed on Dec. 5, 2003. The application is also related to U.S. patent application Ser. Nos. 10/453,175 and 10/730,172.

TECHNICAL FIELD OF THE INVENTION

This invention relates to substituted 3-amino-thieno[2,3-b]pyridine-2-carboxylic acid amide compounds useful as inhibitors of the kinase activity of the IκB kinase (IKK) complex. The compounds are therefore useful in the treatment of IKK-mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNF-α and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell,* 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.,* 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell,* 1994, 78, 773), freeing NF-κB to translocate to the nucleus. The phosphorylation of IκB is carried out by the IκB kinases (see for example a review by M. Karin and M. Delhase, *Seminars in Immunology,* 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKγ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An IKKβ mutant having alanines in place of serines at 177 and 181 prevented IKKβ phosphorylation and subsequent activation of the IKK complex by TNFα, IL-1 and other upstream activators. These results support a key role for IKKβ in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. In these studies, NF-κB activation was prevented by expression of a non-degradable version of the IκB protein. Expression of this inhibitor in synovial cells derived from rheumatoid arthritis patients reduced the expression of TNF-α, IL-6, IL-1β and IL-8 while the anti-inflammatory molecules IL-10, IL-1ra and IL-11 were not affected. Matrix metalloproteinases (MMP1 and MMP3) were also down-regulated (J. Bonderson et al., *Proc. Natl. Acad. Sci. U.S.A.,* 1999, 96, 5668). Transgenic expression of the IκB inhibitor in T cells caused a significant reduction in the severity and onset of collagen—induced arthritis in mice (R. Seetharaman et al., *J. Immunol.* 1999, 163, 1577). These experiments indicate that suppression of NF-κB in the diseased joint could reduce both the severity and progression of RA. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.,* 1998, 160, 410). Expression of this inhibitor in certain tumor cells enhances killing of these cells by chemotherapeutic reagents (A. A. Beg and D. Baltimore, *Science,* 1996, 274, 782).

Analysis of biopsies from lungs of patients with chronic obstructive pulmonary disease (COPD) found an increased expression of NF-κB that correlated with disease severity (A. Di Stefano et al., *Eur. Resp. J.,* 2002, 1, 437). Inhibition of NF-κB activation with inhibitors of IKK-β was among the anti-inflammatory approaches reported to be potentially useful in the treatment of COPD (P. J. Barnes, *Nature Rev. Drug Disc.,* 2002, 1, 437). Likewise, inhibition of NF-κB activity has been mentioned as a therapeutic approach for asthma (A. Pahl and I. Szelenyi, *Infl. Res.,* 2002, 51, 273).

A recent review describes the essential role of inflammatory mediators in the development cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American,* 2002, 46).

A number of studies indicate that activation of NF-κB also plays a key role in the pathogenesis and development of cancer (see for example reviews by B. Haefner, *Drug Disc. Today,* 2002, 7, 653 and M. Karin et al., *Nat. Rev.* Cancer, 2002, 2, 301). Studies have shown that cells in which NF-κB is constitutively active are resistant to apoptosis. This can contribute to carcinogenesis by preventing cell death in cells that have undergone chromosomal changes or damage. In addition tumor cells with constitutively active NF-κB are resistant to anti-cancer therapies including chemotherapy and radiation. Further studies have linked activated NF-κB to a variety of lymphoid-, myeloid- and epithelial-derived malignancies including leukemia, lymphomas and breast, gastric, colorectal, lung, and pancreatic cancers. Thus it is suggested that inhibitors of NF-κB, including inhibitors of IKKα and IKKβ, may be useful either alone or in combination with other anti-cancer therapies in treating cancer.

Collectively, the studies described above provide support that inhibition of NF-κB function through inhibition of IKK may be a useful therapeutic approach to treatment of autoimmune and inflammatory disease, cardiovascular disease and cancer.

Studies have also been done in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., *Science*, 1999, 284, 321), supporting a key role for IKKβ in and NF-κB activation following inflammatory stimuli.

A conditional knockout was generated by expressing a liver-specific inducible dominant negative IκBα transgene (I. Lavon et al., *Nature Medicine*, 2000, 6, 573). These mice were viable with no signs of liver dysfunction even after one year but they did have impaired immune function. This study supports the idea that inhibition of IKKβ can result in immune suppression without damage to the liver.

IKKα knock-out mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., *Science*, 1999, 284, 316; K. Takeda et al., *Science*, 1999, 284, 313). Recent studies with knockout and knock-in mice have revealed distinct roles for IKKα in development and cell signaling. In contrast to the studies with IKKα knock-out mice, mice having a kinase inactive version of IKKα knocked in are viable and fertile, indicating that the perinatal lethality and abnormalities seen in the IKKα knock-out mice are not due to the lack of kinase activity. However, these mice do have defects in B cell maturation and development of secondary lymphoid organs (U. Senftleben et al., *Science*, 2001, 293, 1495). This phenotype appears to be due to a defect in processing of the NF-κB2/p100 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., *Cell*, 2001, 107, 763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., *Immunological Rev.*, 1999, 169, 107) and rheumatoid arthritis (A. Gause and C. Borek, *Biodrugs*, 2001, 15, 73). In addition, an inhibitor of IKKα may be useful in the treatment of breast cancer since NF-κB is constitutively active in a number of breast tumors and many of these tumors depend on Cyclin D1 for proliferation.

Some inhibitors of IKKβ have been reported. For example, WO 01/58890 and WO 03/037886 describe heteoaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., *Nature*, 1998, 396, 77).

Substituted thienopyridines having cell adhesion inhibiting activity are reported in US 2001/0020030 A1 and A. O. Stewart et al., *J. Med. Chem.*, 2001, 44, 988. Thienopyridines exhibiting gonadotropin releasing hormone antagonizing activity are reported in U.S. Pat. No. 6,313,301. Substituted thienopyridines described as telomerase inhibitors are disclosed in U.S. Pat. No. 5,656,638.

A number of 4,6-disubstituted thieno[2,3-b]pyridine-2-carboxylic acid amides have been described in the chemical literature. Examples include 3-amino-4,6-dimethyl-thieno[2,3-b]pyridine-2-carboxylic acid amide, 3-amino-6-methyl-thieno[2,3-b]pyridine-2,4-dicarboxylic acid diamide, 3-amino-4-methyl-6-phenyl-thieno[2,3-b]-pyridine-2-carboxamide, 3-amino-6-methyl-4-phenyl-thieno[2,3-b]pyridine-2-carboxylic acid amide, 3-amino-6-(4-bromo-phenyl)-4-methyl-thieno[2,3-b]pyridine-2-carboxylic acid amide, 3-amino4-(4-bromo-phenyl)-6-methyl-thieno[2,3-b]pyridine-2-carboxylic acid amide, 3-amino-6-methyl-thieno[2,3-b]pyridine-2,4-dicarboxylic acid 2-amide 4-butylamide, 3-amino-6-furan-2-yl-4-phenyl-thieno[2,3-b]pyridine-2-carboxylic acid amide, 3-amino-6-furan-2-yl-4-pyridin-3-yl-thieno[2,3-b]pyridine-2-carboxylic acid amide, 3-amino-4-(4-chloro-phenyl)-6-phenyl-thieno[2,3-b]pyridine-2-carboxylic acid amide, 3-amino-4-(4-fluoro-phenyl)-6-furan-2-yl-thieno[2,3-b]pyridine-2-carboxylic acid amide, 3-amino-4-(4-chloro-phenyl)-6-furan-2-yl-thieno[2,3-b]pyridine-2-carboxylic acid amide, 3-amino-4-(4-bromo-phenyl)-6-furan-2-yl-thieno[2,3-b]pyridine-2-carboxylic acid amide, 3-amino-4,6-bis-(4-chloro-phenyl)-thieno[2,3-b]pyridine-2-carboxylic acid amide, 3-amino-6-naphth-2-yl-4-pyridin-3-yl-thieno[2,3-b]pyridine-2-carboxylic acid amide, 3-amino-6-methyl-thieno[2,3-b]pyridine-2,4-dicarboxylic acid 2-amide 4-(2-hydroxyethyl)amide, 3-amino-6-methyl-4-piperidin-1-yl-thieno[2,3-b]-pyridine-2-carboxamide and 3-amino-4-methyl-6-hydroxy-thieno[2,3-b]-pyridine-2-carboxamide reported as intermediates for synthesis of tricyclic heterocycles and evaluated for anti-allergic activity (G. Wagner et al., *Pharmazie*, 1990, 45, 102).

Other examples includes 3-amino-4,6-diphenyl-thieno[2,3-b]pyridine-2-carboxylic acid amide (A. M. Shestopalov et al., *J. Org. Chem. USSR*, (Engl. Transl.) 1984, 20, 1382), 3-amino-6-methyl-4-pyridin-4-yl-thieno[2,3-b]pyridine-2-carboxylic acid amide and 3-amino-6-methyl-4-pyridin-3-yl-thieno[2,3-b]pyridine-2-carboxylic acid amide (G. Wagner et al., *Pharmazie*, 1993, 48, 514), 3-amino-4-methoxymethyl-6-methyl-thieno[2,3-b]pyridine-2-carboxylic acid amide (E. I. Kaigorodova et al., *Chem. Heterocycl. Compd.* (*Engl. Transl.*), 1996, 32, 1234), 3-amino-6-phenyl-4-thiophen-2-yl-thieno[2,3-b]pyridine-2-carboxylic acid amide, 3-amino-4-furan-2-yl-6-methyl-thieno[2,3-b]pyridine-2-carboxylic acid amide, 3-amino-4-(4-chloro-phenyl)-6-methyl-thieno[2,3-b]pyridine-2-carboxylic acid amide and 3-amino-4-furan-2-yl-6-phenyl-thieno[2,3-b]pyridine-2-carboxylic acid amide (F. A. Attaby, *Phosphorus, Sulfur, Silicon Relat. Elem.*, 1998, 139, 1), 3-amino-6-(4-chloro-phenyl)-4-thiophen-2-yl-thieno[2,3-b]pyridine-2-carboxylic acid amide (Y. Sharanin et al., *J. Org. Chem. USSR*, (Engl. Transl.) 1996, 32, 1207), 3-amino-6-phenyl-4-pyridin-3-yl-thieno[2,3-b]pyridine-2-carboxylic acid amide (A. Krauze, *Eur. J. Med. Chem. Chim. Ther.*, 1999, 34, 301) and 3-amino-6-thiophen-2-yl-4-trifluoromethyl-thieno[2,3-b]pyridine-2-carboxylic acid amide (M. I. Abdel-Monem et al., *Pharmazie*, 2001, 56, 41).

In no case are these compounds described as having the ability to inhibit IKKα or IKKβ.

SUMMARY OF THE INVENTION

It is therefore an object of this invention to provide novel compounds according to the following formula (I):

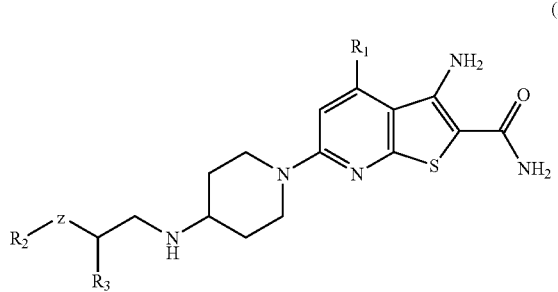

wherein the variables $R_1$, $R_2$, $R_3$ and Z are described herein which inhibit IKK. It is a further object of the invention to provide methods for treating diseases and pathological conditions exacerbated by IKK such as, but not limited to autoimmune diseases, inflammatory diseases and cancer. It is yet a further object of the invention to provide novel processes for preparation of the above-mentioned novel compounds.

DETAILED DESCRIPTION OF THE INVENTION

A first aspect of the invention comprises a method of treating an inflammatory or autoimmune condition by administration of certain novel and known molecules of the formula (I):

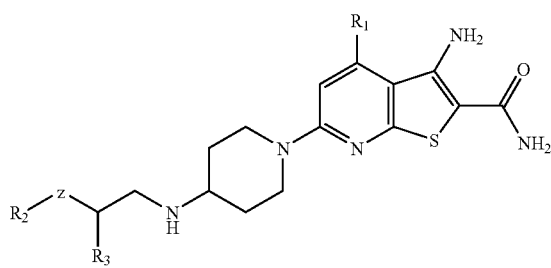

wherein:
$R_1$ is
(a) phenyl or heteroaryl selected from furanyl, thienyl, pyridyl, pyrrolyl, imidazolyl and benzofuranyl, optionally substituted with one to two $R_4$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O) heteroaryl, wherein the heteroaryl is selected from furanyl, thienyl, pyridyl and pyrrolyl,
(c) $R_7(CH_2)_mO$—,
(d) $R_7OCH_2$—,
(e) $R_7(CH_2)_mNH$—,
(f) $R_7(CH_2)_p(CH=CH)_m$—,
(g) $C_{1-6}$alkyl, optionally partially of fully halogenated and optionally substituted with one to two $R_8$,
(h) $C_{1-8}$alkoxy, optionally partially of fully halogenated and optionally substituted with one to two $R_8$,
(i) $C_{1-8}$alkylS(O)$_n$—, optionally partially of fully halogenated and optionally substituted with one to two $R_8$,
(j) —N($R_5$)($R_6$), or
(k) —C(O)NHR', wherein R' is $R_7$, pyridyl or —$CH_3$;
$R_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, optionally substituted with one to three $R_4$;
$R_3$ is —OH or —H;
$R_4$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$S(O)_n$-p-tolyl, —$NO_2$, —OH, —$CF_3$, —$N(R_5)(R_6)$, —$NHC(O)NHC_{1-6}$alkyl, —$C(O)N(R_5)(R_6)$, phenyl optionally substituted with halogen, $C_{1-6}$alkyl, —CN or $C_{1-6}$alkoxy, and heteroaryl chosen from $R_9$;
$R_5$ and $R_6$ are independently selected from H, $C_{1-6}$alkyl, —$C(O)C_{1-6}$alkyl, —$SO_2C_{1-6}$alkyl, phenyl, pyridyl, benzyl, piperidinyl, phenylethyl and $(CH_3)_3COC(O)$—;
$R_7$ is a phenyl group optionally substituted with one or two groups selected from halogen, $C_{1-6}$alkyl, —CN, —$CO_2C_{1-6}$alkyl, —$C(O)NR_5R_6$, —$SO_2NH_2$, —$NO_2$, —OH, —$NH_2$, —$CF_3$ and $C_{1-6}$alkoxy, or $R_7$ is $C_{3-6}$cycloalkyl, —$CH_2OH$, naphthalene-2-yl, naphthalene-1-yl, pyridyl or thienyl;
$R_8$ is selected from oxo, —OH, —$NR_4R_5$, —$CO_2H$ and $C_{1-6}$alkoxy;
$R_9$ is is a heteroaryl selected from the group of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl and methyl imidizolyl, carbanomethylsulfanyl, methoxypiperdinyl, methoxypyridinyl, bromopyridynyl and methoxypyrimidynyl;
m is 0 or 1;
n is 0, 1 or 2;
p is 0, 1, 2 or 3;
Z is a bond or —O—$CH_2$—;

and pharmaceutically acceptable salts, esters, tautomers, individual isomers, and mixtures of isomers thereof.

In its second aspect, the invention provides novel compounds of formula (I) as described above wherein:
$R_1$ is
(a) $R_7(CH=CH)$—,
(b) $C_{1-6}$alkyl,
(c) —$C_{2-3}$alkylOH,
(d) —$CF_3$,
(e) —$C_{1-6}$alkoxy, optionally partially or fully halogenated (f) —OC$_{2-3}$alkylOH,
(g) —C$_{1-6}$alkylthio, or
(h) —C(O)NHR', wherein R' is R$_6$, pyridyl or —CH$_3$;

R$_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, benzofuranyl, benzothienyl, benzimidazolyl, benzthiazolyl, benzoxazolyl, quinolinyl, isoquinolinyl, quinazolinyl, quinoxalinyl and naphthyridinyl, optionally substituted with one to three R$_4$;

R$_3$ is —OH or —H;

R$_4$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N(R$_5$)(R$_6$), —NHC(O)NHC$_{1-6}$alkyl, —C(O)N(R$_5$)(R$_6$), phenyl optionally substituted with halogen, C$_{1-6}$alkyl, —CN or C$_{1-6}$alkoxy, and heteroaryl chosen from R$_9$;

R$_5$ and R$_6$ are independently selected from H, C$_{1-6}$alkyl, —C(O)C$_{1-6}$alkyl, —SO$_2$C$_{1-6}$alkyl, phenyl, pyridyl, benzyl, piperidinyl, phenylethyl and (CH$_3$)$_3$COC(O)—;

R$_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or R$_7$ is C$_{3-6}$cycloalkyl, —CH$_2$OH, naphthalene-2-yl, naphthalene-1-yl, pyridyl or thienyl;

R$_9$ is is a heteroaryl selected from the group of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl and methyl imidizolyl, carbanomethylsulfanyl, methoxypiperdinyl, methoxypyridinyl, bromopyridynyl and methoxypyrimidynyl;

n is 0, 1 or 2;

Z is a bond or —O—CH$_2$—;

and pharmaceutically acceptable salts, esters, tautomers, individual isomers, and mixtures of isomers thereof.

In another embodiment, there are provided novel compounds of the formula (I) as described above and wherein:

R$_1$ is
(a) R$_7$(CH=CH)—,
(b) C$_{1-6}$alkyl,
(c) —CF$_3$,
(d) —C$_{1-6}$alkoxy, optionally partially or fully halogenated
(e) —C$_{1-6}$alkylthio, or
(f) —C(O)NHR', wherein R' is R$_6$, pyridyl or —CH$_3$;

R$_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, benzofuranyl, benzothienyl, benzimidazolyl, benzthiazolyl, benzoxazolyl, quinolinyl, isoquinolinyl, quinazolinyl, quinoxalinyl and naphthyridinyl, optionally substituted with one to three R$_9$;

R$_3$ is —OH;

R$_4$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

R$_5$ and R$_6$ are independently selected from H, C$_{1-6}$alkyl, —C(O)C$_{1-6}$alkyl, —SO$_2$C$_{1-6}$alkyl, phenyl, pyridyl, benzyl, piperidinyl, phenylethyl and (CH$_3$)$_3$COC(O)—;

R$_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or R$_7$ is C$_{3-6}$cycloalkyl, —CH$_2$OH, naphthalene-2-yl, naphthalene-1-yl, pyridyl or thienyl;

n is 0, 1 or 2;

Z is a bond or —O—CH$_2$—;

and pharmaceutically acceptable salts, esters, tautomers, individual isomers, and mixtures of isomers thereof.

In yet another embodiment of the invention there are provided novel compounds of the formula (I) as described above and wherein:

R$_1$ is
(a) R$_7$(CH=CH)—,
(b) C$_{1-6}$alkyl,
(c) —CF$_3$,
(d) —C$_{1-6}$alkoxy, optionally partially or fully halogenated
(e) —C$_{1-6}$alkylthio, or
(f) —C(O)NHR', wherein R' is R$_6$, pyridyl or —CH$_3$;

R$_2$ is heteroaryl selected from the group consisting of, thienyl, thiazolyl, imidazolyl, pyridinyl, pyrimidinyl, pyrazinyl, indolyl, benzothienyl, benzimidazolyl, benzthiazolyl, quinolinyl and isoquinolinyl; optionally substituted with one to three R$_4$;

R$_3$ is —OH;

R$_4$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

R$_5$ and R$_6$ are independently selected from H, C$_{1-6}$alkyl, —C(O)C$_{1-6}$alkyl, —SO$_2$C$_{1-6}$alkyl, phenyl, pyridyl, benzyl, piperidinyl and phenylethyl;

R$_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or R$_7$ is C$_{3-6}$cycloalkyl, —CH$_2$OH, naphthalene-2-yl, naphthalene-1-yl, pyridyl or thienyl;

n is 0, 1 or 2;

Z is a bond or —OCH$_2$—;

and pharmaceutically acceptable salts, esters, tautomers, individual isomers, and mixtures of isomers thereof.

In still another embodiment of the invention there are provided novel compounds of the formula (I) as described above and wherein:

R$_1$ is
(a) R$_7$(CH=CH)—,
(b) C$_{1-6}$alkyl,
(c) —CF$_3$,
(d) —C$_{1-6}$alkoxy, optionally partially or fully halogenated
(e) —C$_{1-6}$alkylthio, or
(f) —C(O)NHR', wherein R' is R$_6$, pyridyl or —CH$_3$;

R$_2$ is heteroaryl selected from the group consisting of, 3-thienyl, 2-thiazolyl, 2-imidazolyl, 2-, 3- and 4-pyridinyl, 4-pyrimidinyl, 2-pyrazinyl, 2-indolyl, 2-benzothienyl, 2-benzimidazolyl, 2-benzthiazolyl, 2-, 3-, 4- and 6-quinolinyl and 1- and 3-isoquinolinyl; optionally substituted with one to three R$_4$;

R$_3$ is —OH;

R$_4$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

$R_5$ and $R_6$ are independently selected from H, $C_{1-6}$alkyl, —C(O)$C_{1-6}$alkyl, —SO$_2$$C_{1-6}$alkyl, phenyl, pyridyl, benzyl, piperidinyl and phenylethyl;

$R_7$ is a phenyl group optionally substituted with one or two groups selected from halogen, $C_{1-6}$alkyl, —CN, —CO$_2$$C_{1-6}$alkyl, —C(O)NR$_5$R$_6$, —SO$_2$NH$_2$, —NO$_2$, —OH, —NH$_2$, —CF$_3$ and $C_{1-6}$alkoxy, or $R_7$ is $C_{3-6}$cycloalkyl, —CH$_2$OH, naphthalene-2-yl, naphthalene-1-yl, pyridyl or thienyl;

n is 0, 1 or 2;

Z is a bond or —O—CH$_2$—;

and pharmaceutically acceptable salts, esters, tautomers, individual isomers, and mixtures of isomers thereof.

In a further embodiment of the invention there are provided novel compounds of the formula (I) as described above and wherein:

$R_1$ is
(a) $C_{1-3}$alkyl,
(b) —CF$_3$, or
(c) —OCH$_2$CF$_3$ $R_2$ is heteroaryl selected from the group consisting of, 3-thienyl, 2-thiazolyl, 2-imidazolyl, 2-, 3- and 4-pyridinyl, 4-pyrimidinyl, 2-pyrazinyl, 2-indolyl, 2-benzothienyl, 2-benzimidazolyl, 2-benzthiazolyl, 2-, 3-, 4- and 6-quinolinyl and 1- and 3-isoquinolinyl; optionally substituted with one to three $R_4$;

$R_3$ is —OH;

$R_4$ is chosen from $C_{1-6}$alkyl, $C_{1-6}$alkoxy, hydroxy$C_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

$R_5$ and $R_6$ are independently selected from H, $C_{1-6}$alkyl, —C(O)$C_{1-6}$alkyl, —SO$_2$$C_{1-6}$alkyl, phenyl, pyridyl, benzyl, piperidinyl and phenylethyl;

n is 0, 1 or 2;

Z is a bond;

and pharmaceutically acceptable salts, esters, tautomers, individual isomers, and mixtures of isomers thereof.

In a further embodiment of the invention, there are provided the following compounds:

| Structure | Name |
|---|---|
| 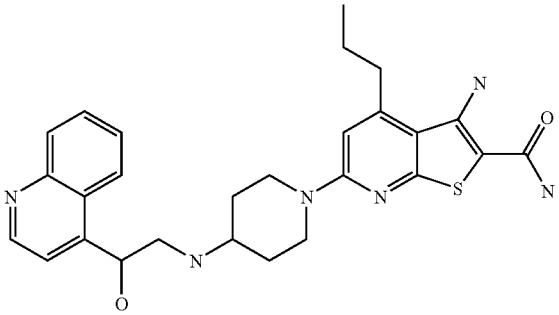 | 3-Amino-6-[4-(2-hydroxy-2-quinolin-4-yl-ethylamino)-piperidin-1-yl]-4-propyl-thieno[2,3-b]pyridine-2-carboxylic acid amide |
| 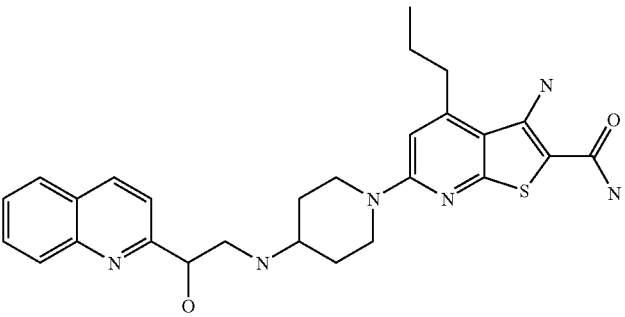 | 3-Amino-6-[4-(2-hydroxy-2-quinolin-2-yl-ethylamino)-piperidin-1-yl]-4-propyl-thieno[2,3-b]pyridine-2-carboxylic acid amide |
| 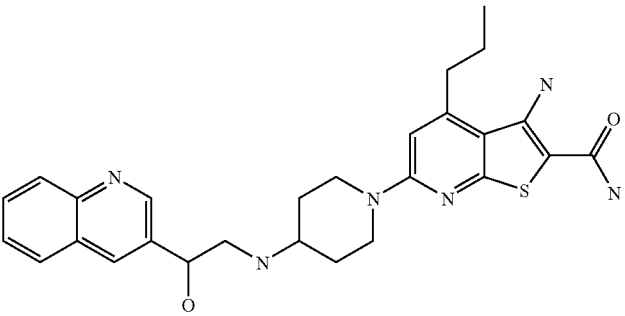 | 3-Amino-6-[4-(2-hydroxy-2-quinolin-3-yl-ethylamino)-piperidin-1-yl]-4-propyl-thieno[2,3-b]pyridine-2-carboxylic acid amide |

| Structure | Name |
|---|---|
| 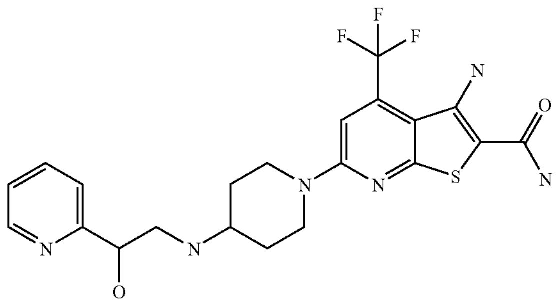 | 3-Amino-6-[4-(2-hydroxy-2-pyridin-2-yl-ethylamino)-piperidin-1-yl]-4-trifluoromethyl-thieno[2,3-b]pyridine-2-carboxylic acid amide |
| 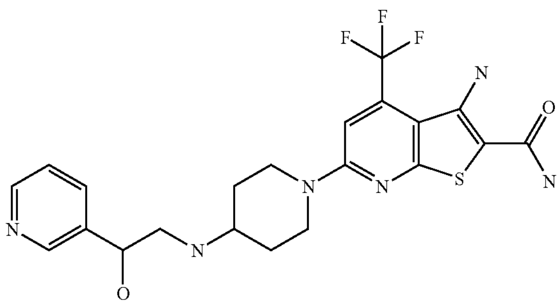 | 3-Amino-6-[4-(2-hydroxy-2-pyridin-3-yl-ethylamino)-piperidin-1-yl]-4-trifluoromethyl-thieno[2,3-b]pyridine-2-carboxylic acid amide |
| 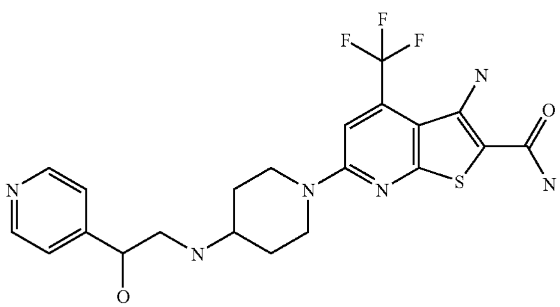 | 3-Amino-6-[4-(2-hydroxy-2-pyridin-4-yl-ethylamino)-piperidin-1-yl]-4-trifluoromethyl-thieno[2,3-b]pyridine-2-carboxylic acid amide |
| 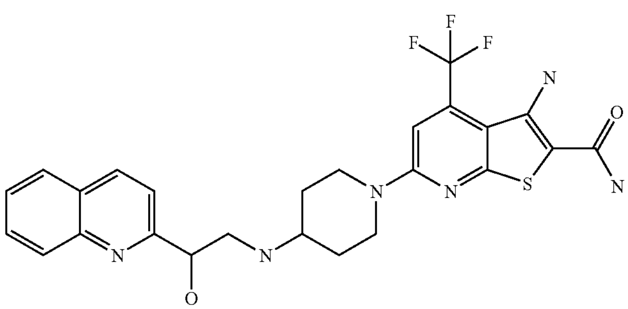 | 3-Amino-6-[4-(2-hydroxy-2-quinolin-2-yl-ethylamino)-piperidin-1-yl]-4-trifluoromethyl-thieno[2,3-b]pyridine-2-carboxylic acid amide |
| 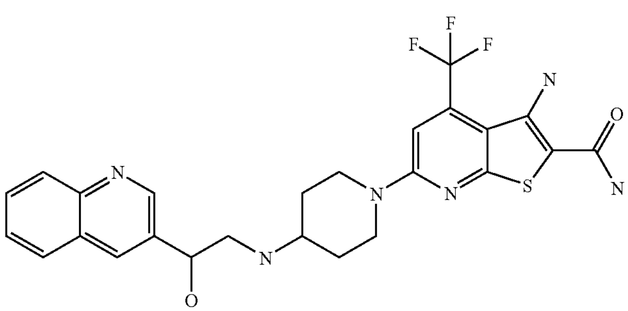 | 3-Amino-6-[4-(2-hydroxy-2-quinolin-3-yl-ethylamino)-piperidin-1-yl]-4-trifluoromethyl-thieno[2,3-b]pyridine-2-carboxylic acid amide |

-continued

| Structure | Name |
|---|---|
| 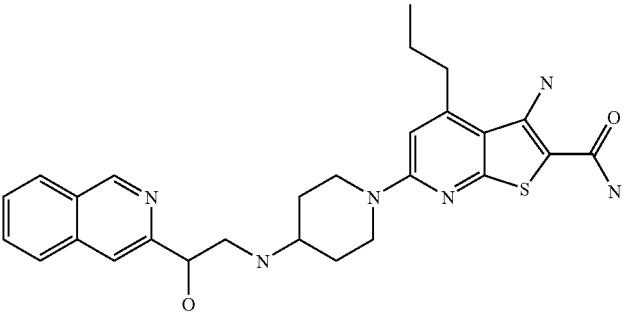 | 3-Amino-6-[4-(2-hydroxy-2-isoquinolin-3-yl-ethylamino)-piperidin-1-yl]-4-propyl-thieno[2,3-b]pyridine-2-carboxylic acid amide |
| 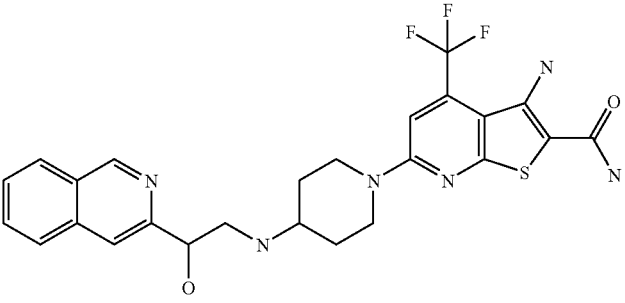 | 3-Amino-6-[4-(2-hydroxy-2-isoquinolin-3-yl-ethylamino)-piperidin-1-yl]-4-trifluoromethyl-thieno[2,3-b]pyridine-2-carboxylic acid amide |
| 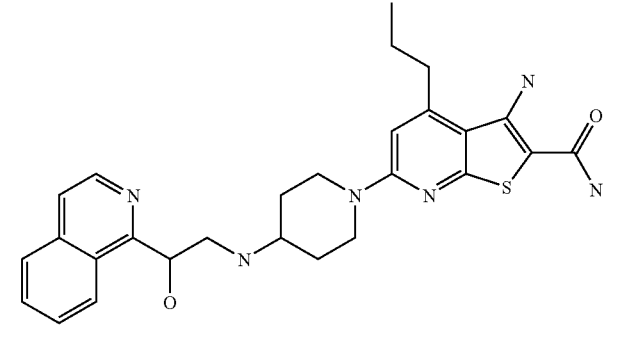 | 3-Amino-6-[4-(2-hydroxy-2-isoquinolin-1-yl-ethylamino)-piperidin-1-yl]-4-propyl-thieno[2,3-b]pyridine-2-carboxylic acid amide |
| 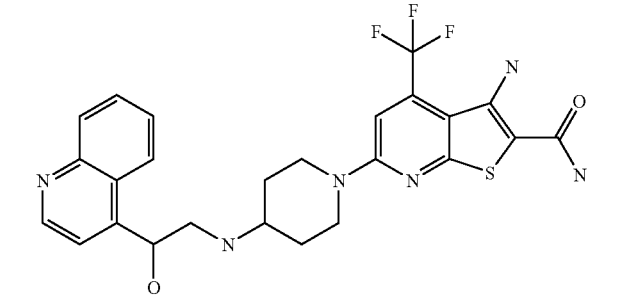 | 3-Amino-6-[4-(2-hydroxy-2-quinolin-4-yl-ethylamino)-piperidin-1-yl]-4-trifluoromethyl-thieno[2,3-b]pyridine-2-carboxylic acid amide |

-continued

| Structure | Name |
|---|---|
| 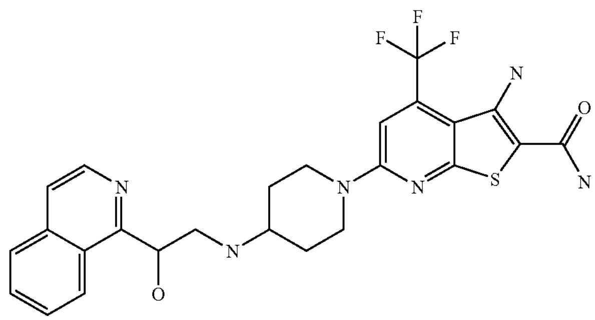 | 3-Amino-6-[4-(2-hydroxy-2-isoquinolin-1-yl-ethylamino)-piperidin-1-yl]-4-trifluoromethyl-thieno[2,3-b]pyridine-2-carboxylic acid amide |
| 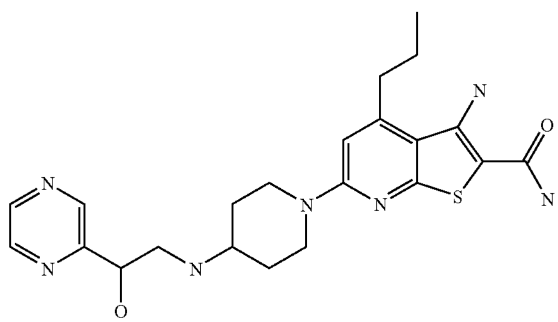 | 3-Amino-6-[4-(2-hydroxy-2-pyrazin-2-yl-ethylamino)-piperidin-1-yl]-4-propyl-thieno[2,3-b]pyridine-2-carboxylic acid amide |
| 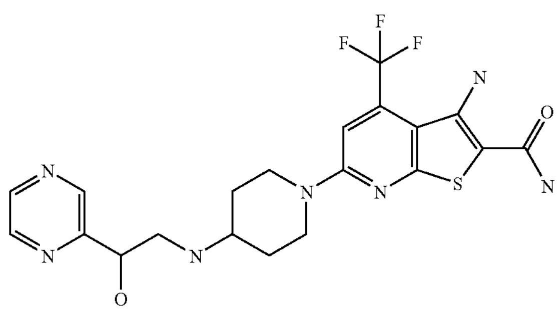 | 3-Amino-6-[4-(2-hydroxy-2-pyrazin-2-yl-ethylamino)-piperidin-1-yl]-4-trifluoromethyl-thieno[2,3-b]pyridine-2-carboxylic acid amide |
| 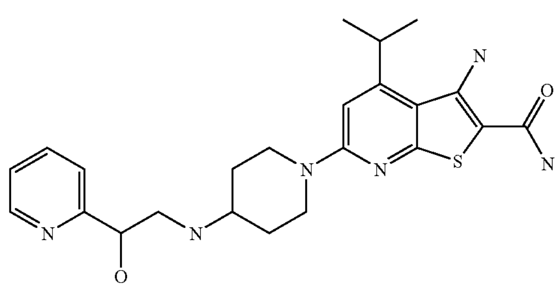 | 3-Amino-6-[4-(2-hydroxy-2-pyridin-2-yl-ethylamino)-piperidin-1-yl]-4-isopropyl-thieno[2,3-b]pyridine-2-carboxylic acid amide |
| 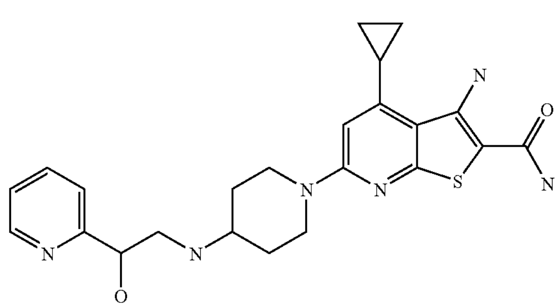 | 3-Amino-4-cyclopropyl-6-[4-(2-hydroxy-2-pyridin-2-yl-ethylamino)-piperidin-1-yl]-thieno[2,3-b]pyridine-2-carboxylic acid amide |

-continued

| Structure | Name |
|---|---|
| 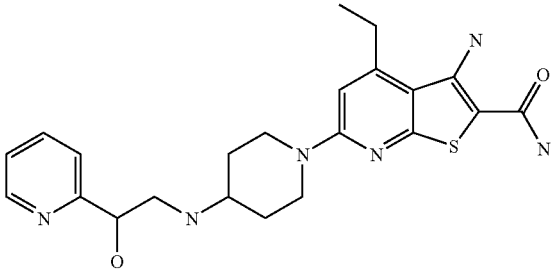 | 3-Amino-4-ethyl-6-[4-(2-hydroxy-2-pyridin-2-yl-ethylamino)-piperidin-1-yl]-thieno[2,3-b]pyridine-2-carboxylic acid amide |
| 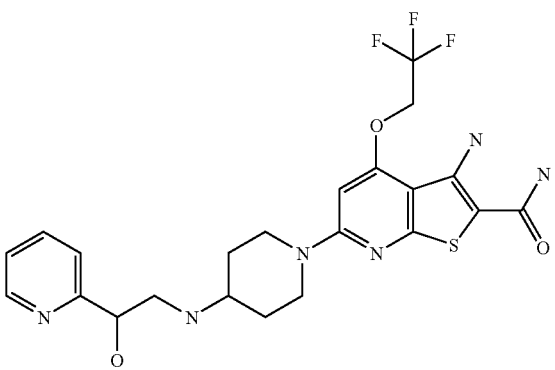 | 3-Amino-6-[4-(2-hydroxy-2-pyridin-2-yl-ethylamino)-piperidin-1-yl]-4-(2,2,2-trifluoro-ethoxy)-thieno[2,3-b]pyridine-2-carboxylic acid amide |
| 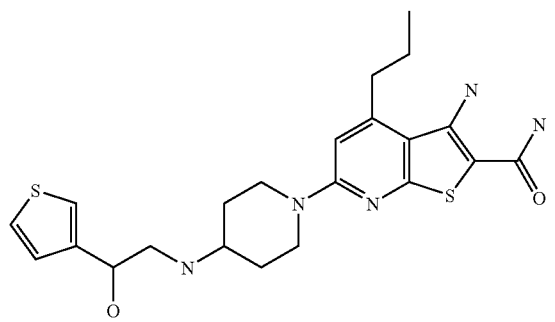 | 3-Amino-6-[4-(2-hydroxy-2-thiophen-3-yl-ethylamino)-piperidin-1-yl]-4-propyl-thieno[2,3-b]pyridine-2-carboxylic acid amide |
| 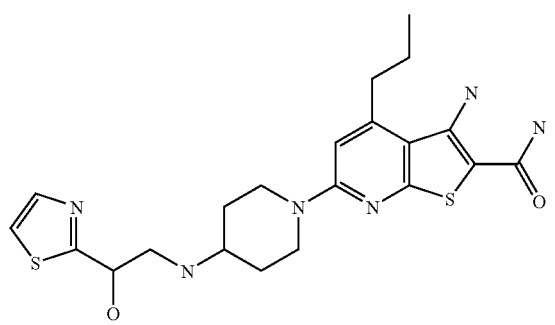 | 3-Amino-6-[4-(2-hydroxy-2-thiazol-2-yl-ethylamino)-piperidin-1-yl]-4-propyl-thieno[2,3-b]pyridine-2-carboxylic acid amide |

-continued

| Structure | Name |
|---|---|
| 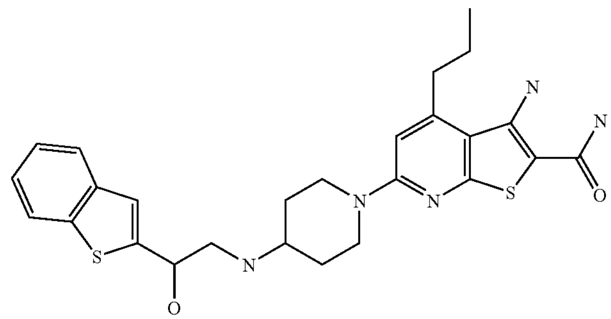 | 3-Amino-6-[4-(2-benzo[b]thiophen-2-yl-2-hydroxy-ethylamino)-piperidin-1-yl]-4-propyl-thieno[2,3-b]pyridine-2-carboxylic acid amide |
| 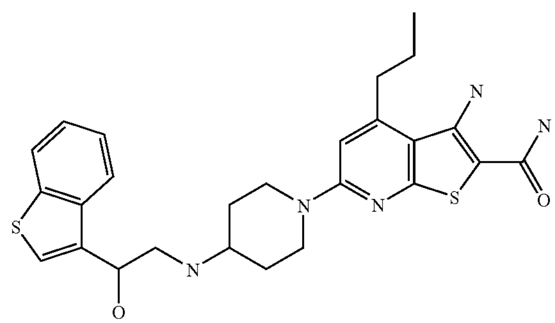 | 3-Amino-6-[4-(2-benzo[b]thiophen-3-yl-2-hydroxy-ethylamino)-piperidin-1-yl]-4-propyl-thieno[2,3-b]pyridine-2-carboxylic acid amide |
| 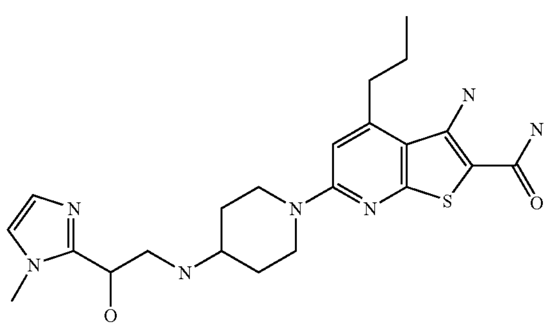 | 3-Amino-6-{4-[2-hydroxy-2-(1-methyl-1H-imidazol-2-yl)-ethylamino]-piperidin-1-yl}-4-propyl-thieno[2,3-b]pyridine-2-carboxylic acid amide |
| 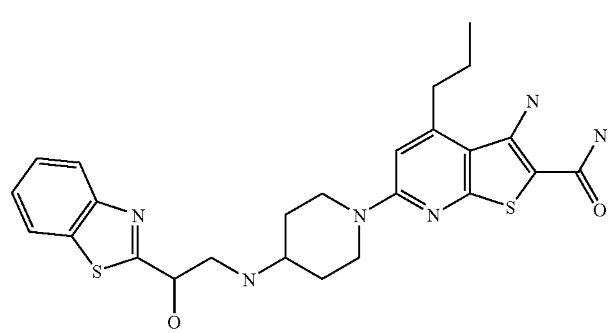 | 3-Amino-6-[4-(2-benzothiazol-2-yl-2-hydroxy-ethylamino)-piperidin-1-yl]-4-propyl-thieno[2,3-b]pyridine-2-carboxylic acid amide |

-continued

| Structure | Name |
|---|---|
| 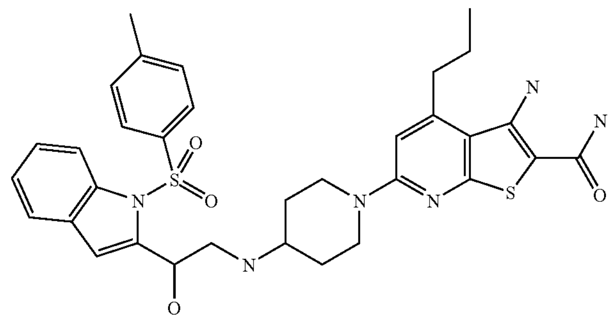 | 3-Amino-6-(4-{2-hydroxy-2-[1-(toluene-4-sulfonyl)-1H-indol-2-yl]-ethylamino}-piperidin-1-yl)-4-propyl-thieno[2,3-b]pyridine-2-carboxylic acid amide |
| 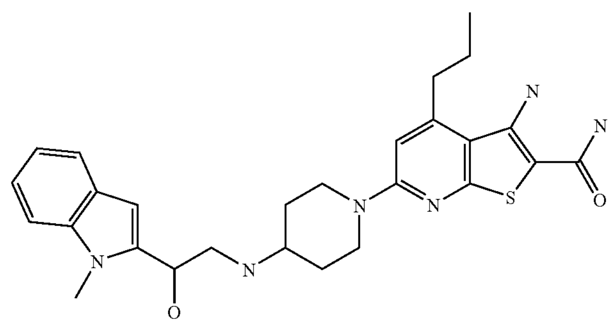 | 3-Amino-6-{4-[2-hydroxy-2-(1-methyl-1H-indol-2-yl)-ethylamino]-piperidin-1-yl}-4-propyl-thieno]2,3-b]pyridine-2-carboxylic acid amide |
| 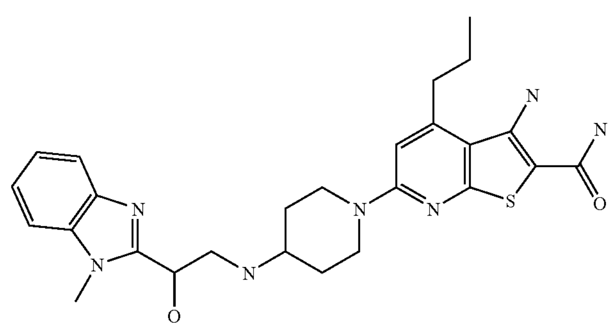 | 3-Amino-6-{4-[2-hydroxy-2-(1-methyl-1H-benzoimidazol-2-yl)-ethylamino]-piperidin-1-yl}-4-propyl-thieno[2,3-b]pyridine-2-carboxylic acid amide |
| 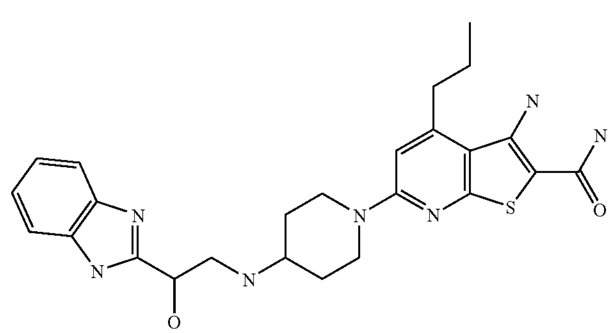 | 3-Amino-6-{4-[2-(1H-benzoimidazol-2-yl)-2-hydroxy-ethylamino]-piperidin-1-yl}-4-propyl-thieno[2,3-b]pyridine-2-carboxylic acid amide |

-continued

| Structure | Name |
|---|---|
| 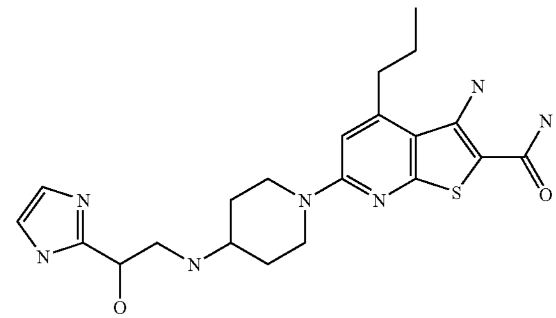 | 3-Amino-6-{4-[2-hydroxy-2-(1H-imidazol-2-yl)-ethylamino]-piperidin-1-yl}-4-propyl-thieno[2,3-b]pyridine-2-carboxylic acid amide |
| 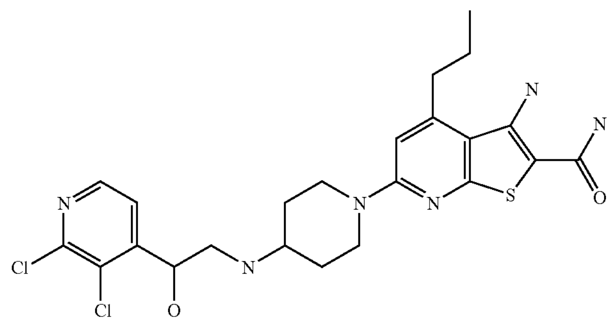 | 3-Amino-6-{4-[2-(2,3-dichloro-pyridin-4-yl)-2-hydroxy-ethylamino]-piperidin-1-yl}-4-propyl-thieno[2,3-b]pyridine-2-carboxylic acid amide |
| 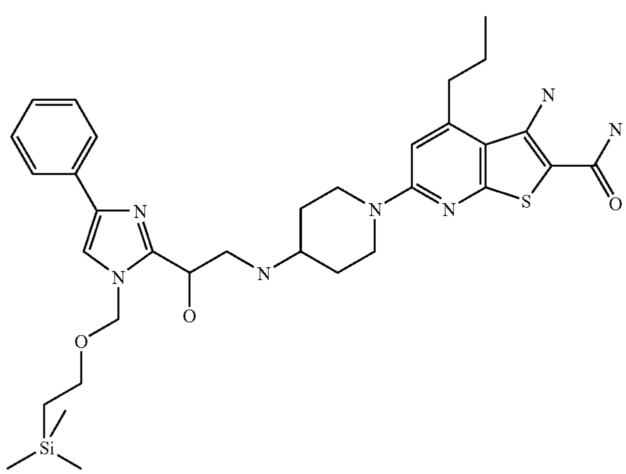 | 3-Amino-6-(4-{2-hydroxy-2-[4-phenyl-1-(2-trimethylsilanyl-ethoxymethyl)-1H-imidazol-2-yl]-ethylamino}-piperidin-1-yl)-4-propyl-thieno[2,3-b]pyridine-2-carboxylic acid amide |
| 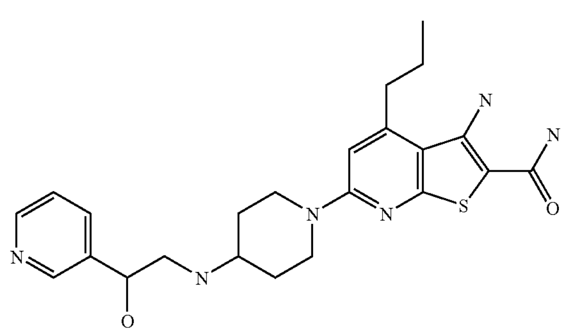 | 3-Amino-6-[4-(2-hydroxy-2-pyridin-3-yl-ethylamino)-piperidin-1-yl]-4-propyl-thieno[2,3-b]pyridine-2-carboxylic acid amide |

| Structure | Name |
|---|---|
| 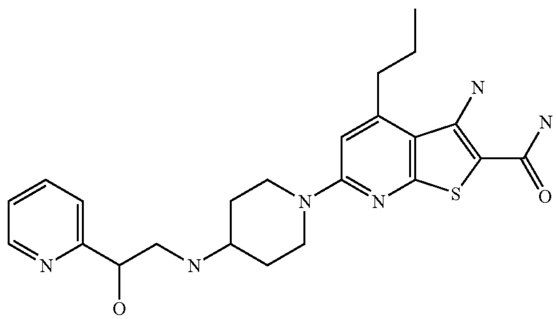 | 3-Amino-6-[4-(2-hydroxy-2-pyridin-2-yl-ethylamino)-piperidin-1-yl]-4-propyl-thieno[2,3-b]pyridine-2-carboxylic acid amide |
| 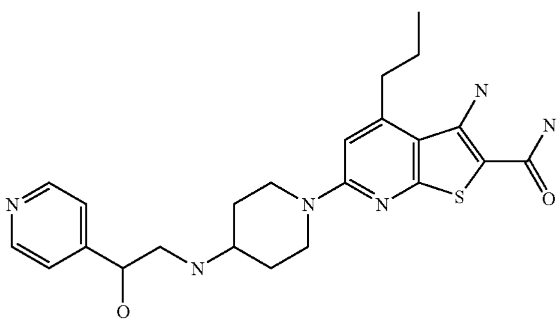 | 3-Amino-6-[4-(2-hydroxy-2-pyridin-4-yl-ethylamino)-piperidin-1-yl]-4-propyl-thieno[2,3-b]pyridine-2-carboxylic acid amide |
| 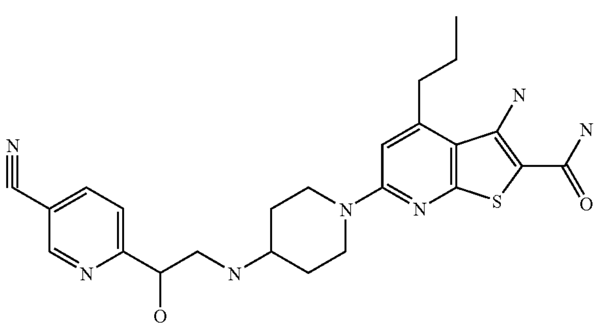 | 3-Amino-6-{4-[2-(5-cyano-pyridin-2-yl)-2-hydroxy-ethylamino]-piperidin-1-yl}-4-propyl-thieno[2,3-b]pyridine-2-carboxylic acid amide |
| 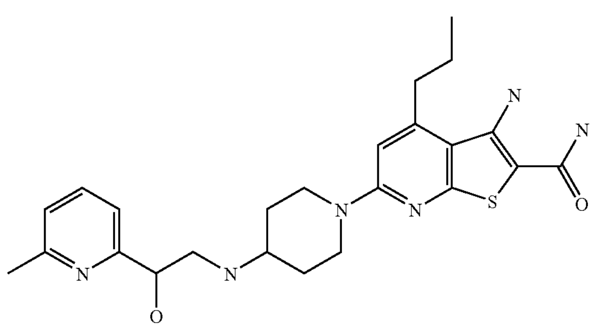 | 3-Amino-6-{4-[2-hydroxy-2-(6-methyl-pyridin-2-yl)-ethylaminol-piperidin-1-yl}-4-propyl-thieno[2,3-b]pyridine-2-carboxylic acid amide |

-continued

| Structure | Name |
|---|---|
| 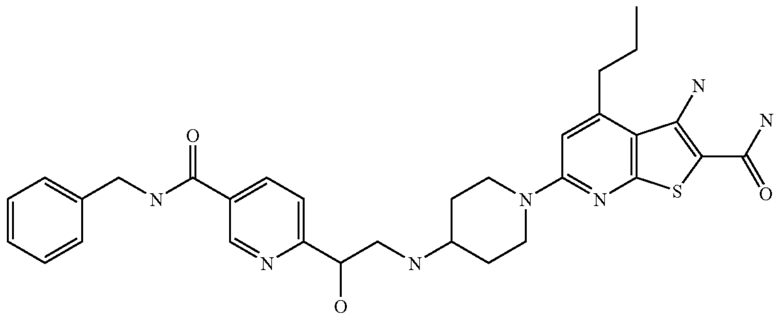 | 3-Amino-6-{4-[2-(5-benzylcarbamoyl-pyridin-2-yl)-2-hydroxy-ethylamino]-piperidin-1-yl}-4-propyl-thieno[2,3-b]pyridine-2-carboxylic acid amide |
| 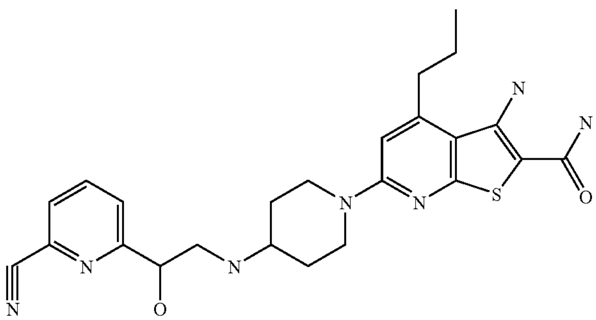 | 3-Amino-6-{4-[2-(6-cyano-pyridin-2-yl)-2-hydroxy-ethylamino]-piperidin-1-yl}-4-propyl-thieno[2,3-b]pyridine-2-carboxylic acid amide |
| 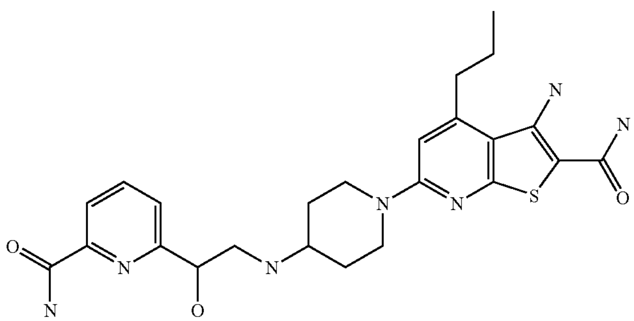 | 3-Amino-6-{4-[2-(6-carbamoyl-pyridin-2-yl)-2-hydroxy-ethylamino] piperidin-1-yl}-4-propyl-thieno[2,3-b]pyridine-2-carboxylic acid amide |
| 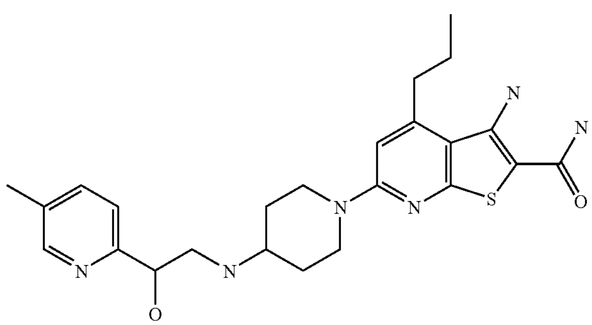 | 3-Amino-6-{4-[2-hydroxy-2-(5-methyl-pyridin-2-yl)-ethylamino]-piperidin-1-yl}-4-propyl-thieno[2,3-b]pyridine-2-carboxylic acid amide |
| 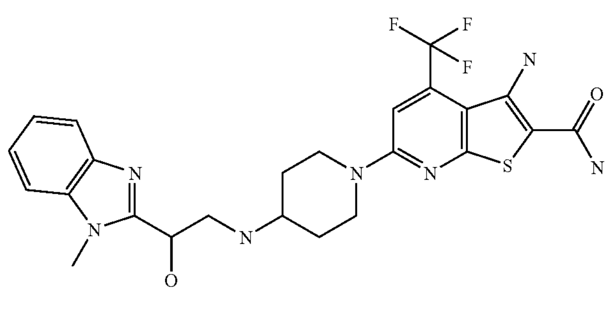 | 3-Amino-6-{4-[2-hydroxy-2-(1-methyl-1H-benzoimidazol-2-yl)-ethylamino]-piperidin-1-yl}-4-trifluoromethyl-thieno[2,3-b]pyridine-2-carboxylic acid amide |

-continued

| Structure | Name |
|---|---|
| 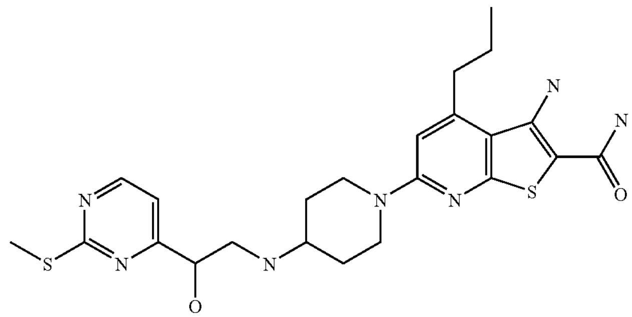 | 3-Amino-6-{4-[2-hydroxy-2-(2-methylsulfanyl-pyrimidin-4-yl)-ethylamino]-piperidin-1-yl}-4-propyl-thieno[2,3-b]pyridine-2-carboxylic acid amide |
| 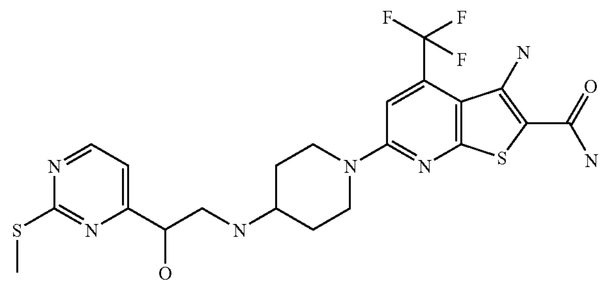 | 3-Amino-6-{4-[2-hydroxy-2-(2-methylsulfanyl-pyrimidin-4-yl)-ethylamino]-piperidin-1-yl}-4-trifluoromethyl-thieno[2,3-b]pyridine-2-carboxylic acid amide |
| 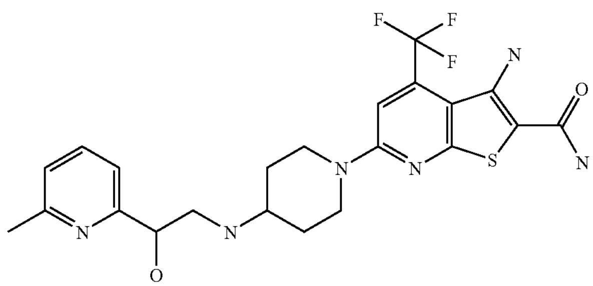 | 3-Amino-6-{4-[2-hydroxy-2-(6-methyl-pyridin-2-yl)-ethylamino]-piperidin-1-yl}-4-trifluoromethyl-thieno[2,3-b]pyridine-2-carboxylic acid amide |
| 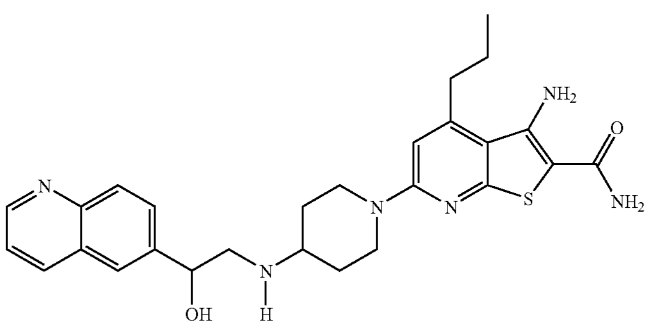 | 3-Amino-6-[4-(2-hydroxy-2-quinolin-6-yl-ethylamino)-piperidin-1-yl]-4-propyl-thieno[2,3-b]pyridine-2-carboxylic acid amide |
| 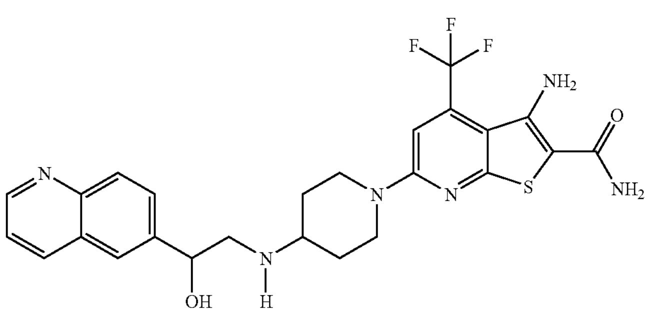 | 3-Amino-6-[4-(2-hydroxy-2-quinolin-6-yl-ethylamino)-piperidin-1-yl]-4-trifluoromethyl-thieno[2,3-b]pyridine-2-carboxylic acid amide |

-continued

| Structure | Name |
|---|---|
| 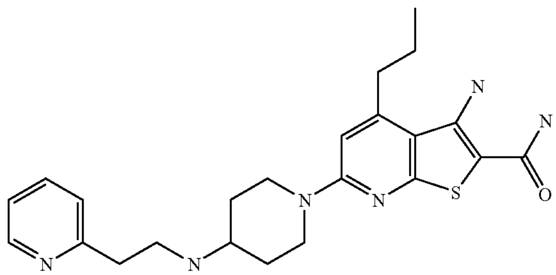 | 3-Amino-4-propyl-6-[4-(2-pyridin-2-yl-ethylamino)-piperidin-1-yl]-thieno[2,3-b]pyridine-2-carboxylic acid amide |
| 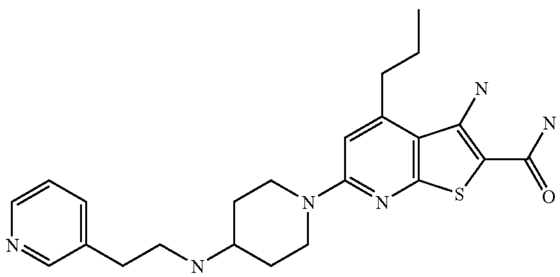 | 3-Amino-4-propyl-6-[4-(2-pyridin-3-yl-ethylamino)-piperidin-1-yl]-thieno[2,3-b]pyridine-2-carboxylic acid amide |
| 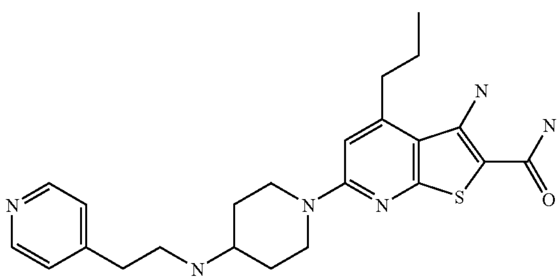 | 3-Amino-4-propyl-6-[4-(2-pyridin-4-yl-ethylamino)-piperidin-1-yl]-thieno[2,3-b]pyridine-2-carboxylic acid amide |
| 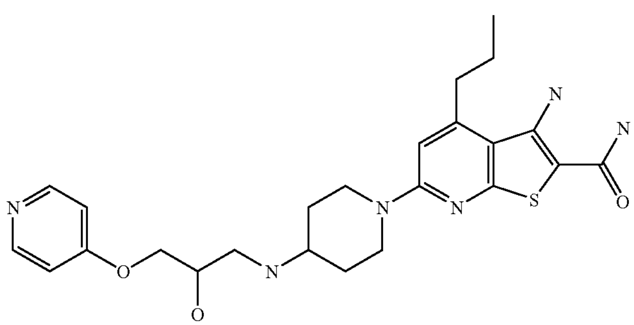 | 3-Amino-6-{4-[2-hydroxy-3-(pyridin-4-yloxy)-propylamino]-piperidin-1-yl}-4-propyl-thieno[2,3-b]pyridine-2-carboxylic acid amide |
| 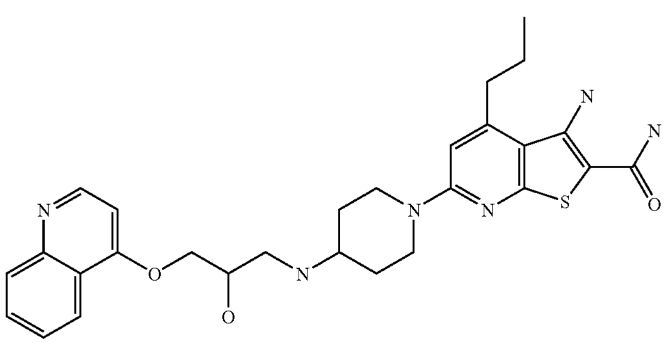 | 3-Amino-6-{4-[2-hydroxy-3-(quinolin-4-yloxy)-propylamino]-piperidin-1-yl}-4-propyl-thieno[2,3-b]pyridine-2-carboxylic acid amide |

-continued

| Structure | Name |
|---|---|
| 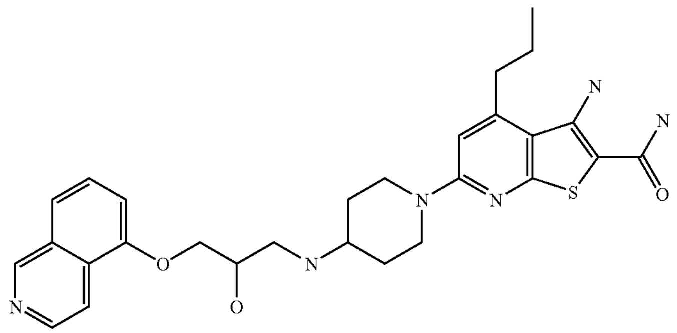 | 3-Amino-6-{4-[2-hydroxy-3-(isoquinolin-5-yloxy)-propylamino]-piperidin-1-yl}-4-propyl-thieno[2,3-b]pyridine-2-carboxylic acid amide |
| 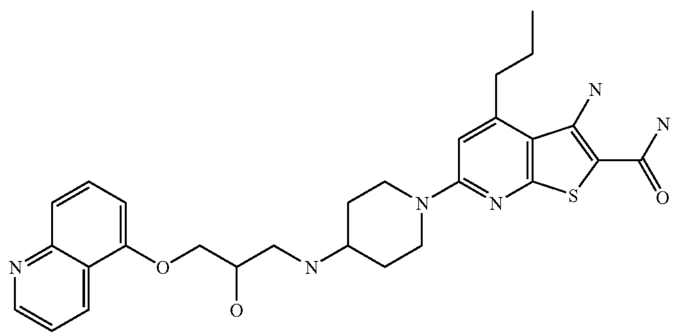 | 3-Amino-6-{4-[2-hydroxy-3-(quinolin-5-yloxy)-propylamino]-piperidin-1-yl}-4-propyl-thieno[2,3-b]pyridine-2-carboxylic acid amide |
| 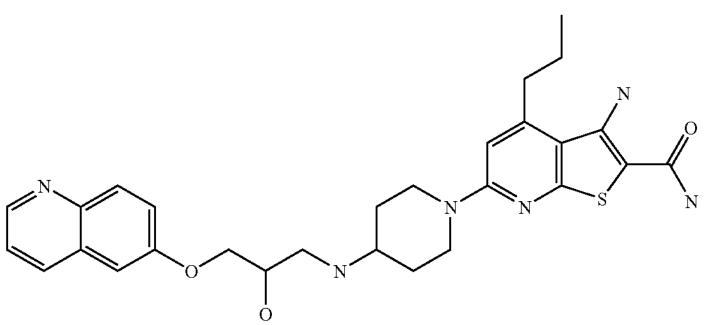 | 3-Amino-6-{4-[2-hydroxy-3-(quinolin-6-yloxy)-propylamino]-piperidin-1-yl}-4-propyl-thieno[2,3-b]pyridine-2-carboxylic acid amide |
| Chiral | 3-Amino-6-{4-[(S)-2-hydroxy-3-(quinolin-6-yloxy)-propylamino]-piperidin-1-yl}-4-trifluoromethyl-thieno[2,3-b]pyridine-2-carboxylic acid amide |

-continued

| Structure | Name |
|---|---|
| Chiral | 3-Amino-6-{4-[(R)-2-hydroxy-3-(quinolin-6-yloxy)-propylamino]-piperidin-1-yl}-4-trifluoromethyl-thieno[2,3-b]pyridine-2-carboxylic acid amide |
| Chiral | 3-Amino-6-[4-((R)-2-hydroxy-2-pyridin-2-yl-ethylamino)-pipendin-1-yl]-4-trifluoromethyl-thieno[2,3-b]pyridine-2-carboxylic acid amide |
| Chiral | 3-Amino-6-[4-((S)-2-hydroxy-2-pyridin-2-yl-ethylamino)-piperidin-1-yl]-4-trifluoromethyl-thieno[2,3-b]pyridine-2-carboxylic acid amide |
| 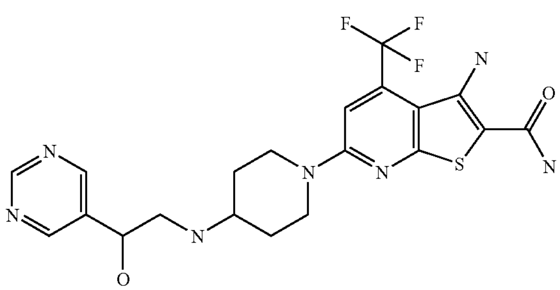 | 3-Amino-6-[4-(2-hydroxy-2-pyrimidin-5-yl-ethylamino)-pipendin-1-yl]-4-trifluoromethyl-thieno[2,3-b]pyridine-2-carboxylic acid amide |

-continued

| Structure | Name |
|---|---|
| Chiral | 3-Amino-6-{4-[(S)-2-(6-chloro-pyridin-2-yl)-2-hydroxy-ethylamino]-piperidin-1-yl}-4-propyl-thieno[2,3-b]pyridine-2-carboxylic acid amide |
| Chiral | 3-Amino-6-{4-[(R)-2-(6-chloro-pyridin-2-yl)-2-hydroxy-ethylamino]-piperidin-1-yl}-4-propyl-thieno[2,3-b]pyridine-2-carboxylic acid amide |
| Chiral | 3-Amino-6-{4-[(S)-2-(6-chloro-pyridin-2-yl)-2-hydroxy-ethylamino]-piperidin-1-yl}-4-trifluoromethyl-thieno[2,3-b]pyridine-2-carboxylic acid amide |
| Chiral | 3-Amino-6-{4-[(R)-2-(6-chloro-pyridin-2-yl)-2-hydroxy-ethylamino]-piperidin-1-yl}-4-trifluoromethyl-thieno[2,3-b]pyridine-2-carboxylic acid amide |

-continued

| Structure | Name |
|---|---|
| Chiral | 3-Amino-6-{4-[(S)-2-hydroxy-2-(6-methyl-pyridin-2-yl)-ethylamino]-piperidin-1-yl}-4-trifluoromethyl-thieno[2,3-b]pyridine-2-carboxylic acid amide |
| Chiral | 3-Amino-6-{4-[(R)-2-hydroxy-2-(6-methyl-pyridin-2-yl)-ethylamino]-piperidin-1-yl}-4-trifluoromethyl-thieno[2,3-b]pyridine-2-carboxylic acid amide |
| 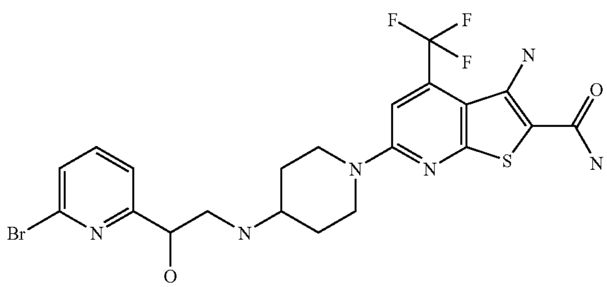 | 3-Amino-6-{4-[2-(6-bromo-pyridin-2-yl)-2-hydroxy-ethylamino]-piperidin-1-yl}-4-trifluoromethyl-thieno[2,3-b]pyridine-2-carboxylic acid amide |
| 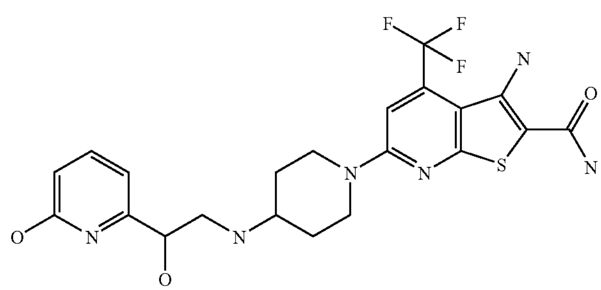 | 3-Amino-6-{4-[2-hydroxy-2-(6-hydroxy-pyridin-2-yl)-ethylamino]-piperidin-1-yl}-4-trifluoromethyl-thieno[2,3-b]pyridine-2-carboxylic acid amide |
| 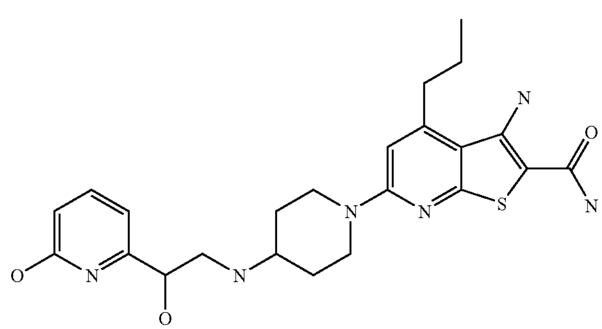 | 3-Amino-6-{4-[2-hydroxy-2-(6-hydroxy-pyridin-2-yl)-ethylamino]-piperidin-1-yl}-4-propyl-thieno[2,3-b]pyridine-2-carboxylic acid amide |

-continued

| Structure | Name |
|---|---|
| 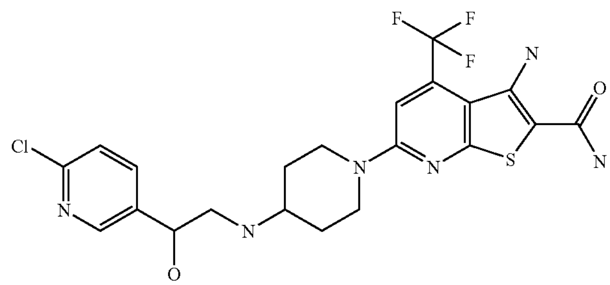 | 3-Amino-6-{4-[2-(6-chloro-pyridin-3-yl)-2-hydroxy-ethylamino]-piperidin-1-yl}-4-trifluoromethyl-thieno[2,3-b]pyridine-2-carboxylic acid amide |
| 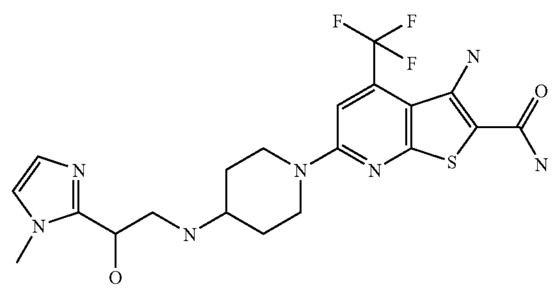 | 3-Amino-6-{4-[2-hydroxy-2-(1-methyl-1H-imidazol-2-yl)-ethylamino]-piperidin-1-yl}-4-trifluoromethyl-thieno[2,3-b]pyridine-2-carboxylic acid amide |
| 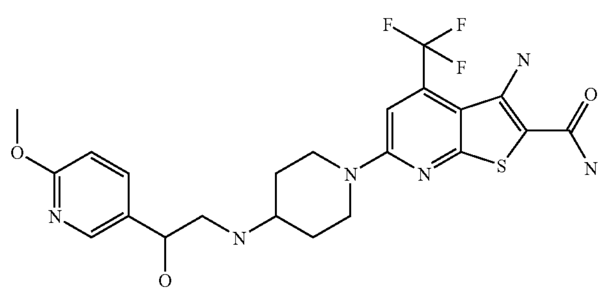 | 3-Amino-6-{4-[2-hydroxy-2-(6-methoxy-pyridin-3-yl)-ethylamino]-piperidin-1-yl}-4-trifluoromethyl-thieno[2,3-b]pyridine-2-carboxylic acid amide |
| 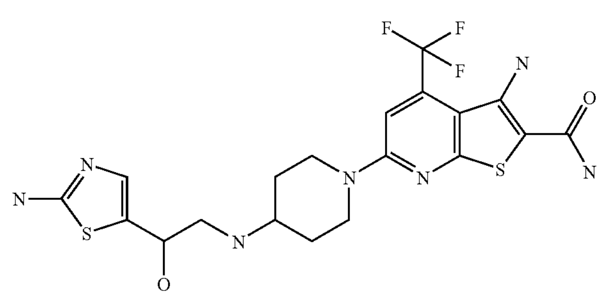 | 3-Amino-6-{4-[2-(2-amino-thiazol-5-yl)-2-hydroxy-ethylamino]-piperidin-1-yl}-4-trifluoromethyl-thieno[2,3-b]pyridine-2-carboxylic acid amide |
| 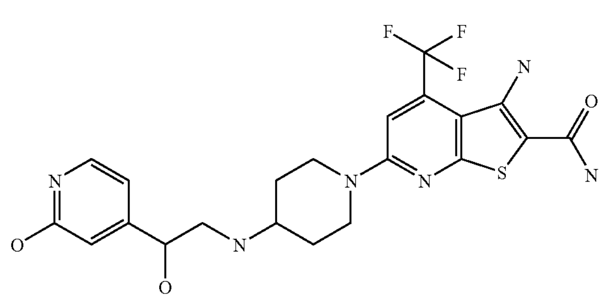 | 3-Amino-6-{4-[2-hydroxy-2-(2-hydroxy-pyridin-4-yl)-ethylamino]-piperidin-1-yl}-4-trifluoromethyl-thieno[2,3-b]pyridine-2-carboxylic acid amide |

| Structure | Name |
|---|---|
| 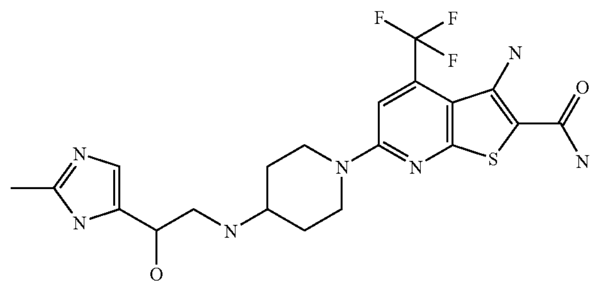 | 3-Amino-6-{4-[2-hydroxy-2-(2-methyl-3H-imidazol-4-yl)-ethylamino]-piperidin-1-yl}-4-trifluoromethyl-thieno[2,3-b]pyridine-2-carboxylic acid amide |
| 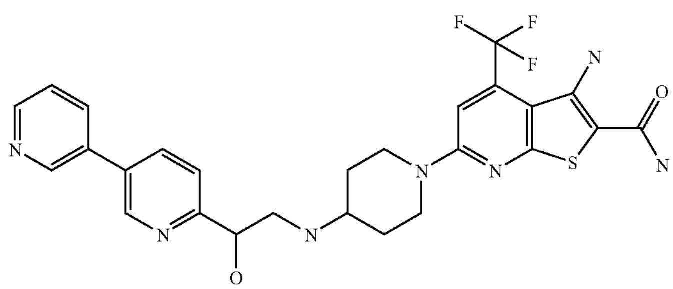 | 3-Amino-6-[4-(2-[3,3']bipyridinyl-6-yl-2-hydroxy-ethylamino)-piperidin-1-yl]-4-trifluoromethyl-thieno[2,3-b]pyridine-2-carboxylic acid amide |
| 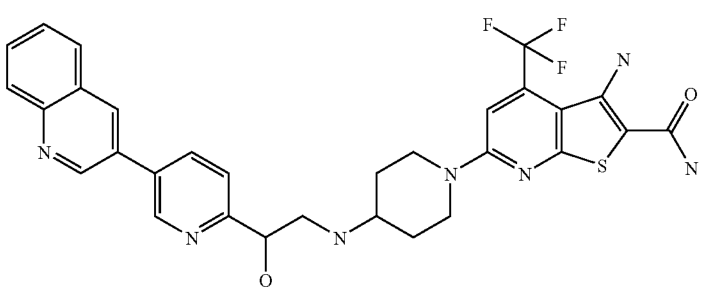 | 3-Amino-6-{4-[2-hydroxy-2-(5-quinolin-3-yl-pyridin-2-yl)-ethylamino]-piperidin-1-yl}-4-trifluoromethyl-thieno[2,3-b]pyridine-2-carboxylic acid amide |
| 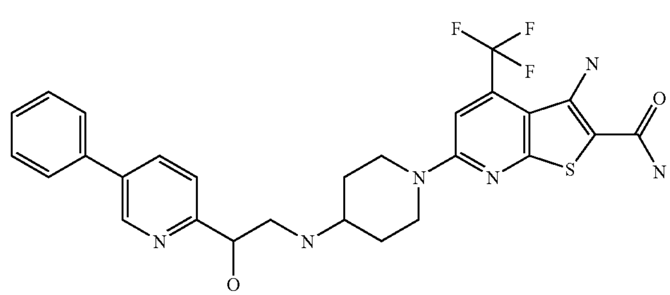 | 3-Amino-6-{4-[2-hydroxy-2-(5-phenyl-pyridin-2-yl)-ethylamino]-piperidin-1-yl}-4-trifluoromethyl-thieno[2,3-b]pyridine-2-carboxylic acid amide |
| | 3-Amino-6-{4-[2-(5-bromo-pyridin-2-yl)-2-hydroxy-ethylamino]-piperidin-1-yl}-4-trifluoromethyl-thieno[2,3-b]pyridine-2-carboxylic acid amide |

-continued

| Structure | Name |
|---|---|
| 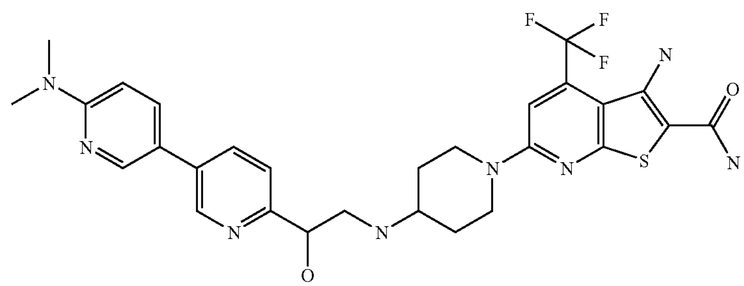 | 3-Amino-6-{4-[2-(6'-dimethylamino-[3,3']bipyridinyl-6-yl)-2-hydroxy-ethylamino]-piperidin-1-yl}-4-trifluoromethyl-thieno[2,3-b]pyridine-2-carboxylic acid amide |
| 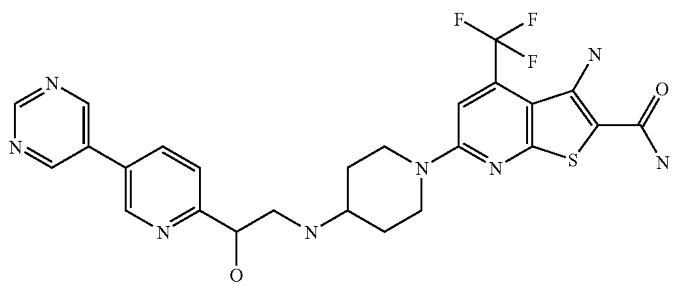 | 3-Amino-6-{4-[2-hydroxy-2-(5-pyrimidin-5-yl-pyridin-2-yl)-ethylamino]-piperidin-1-yl}-4-trifluoromethyl-thieno[2,3-b]pyridine-2-carboxylic acid amide |
| 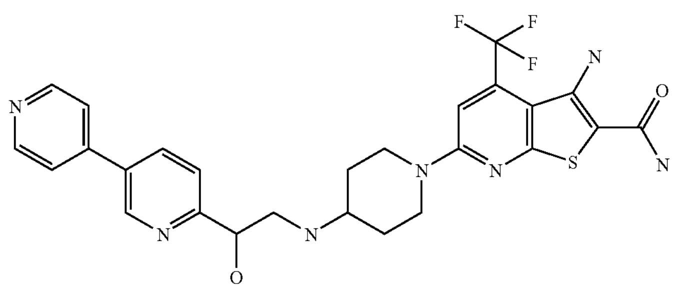 | 3-Amino-6-[4-(2-[3,4']bipyridinyl-6-yl-2-hydroxy-ethylamino)-piperidin-1-yl]-4-trifluoromethyl-thieno[2,3-b]pyridine-2-carboxylic acid amide |
| 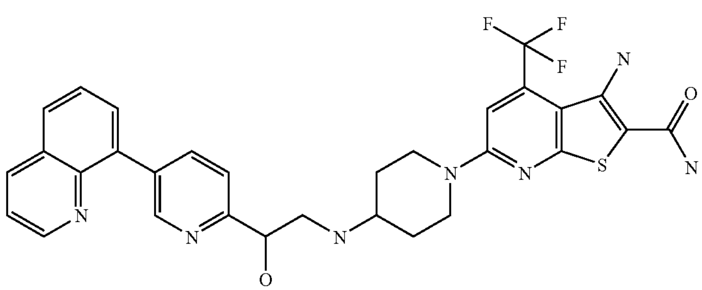 | 3-Amino-6-{4-[2-hydroxy-2-(5-quinolin-8-yl-pyridin-2-yl)-ethylamino]-piperidin-1-yl}-4-b]pyridine-2-carboxylic acid amide |
| 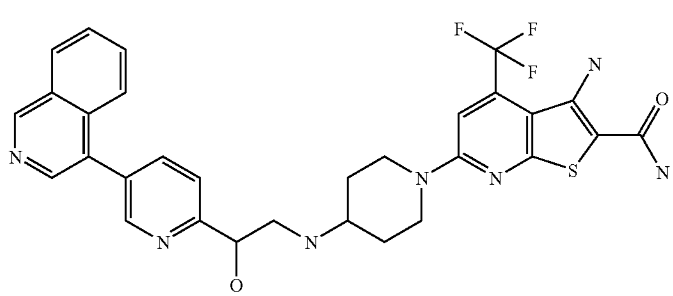 | 3-Amino-6-{4-[2-hydroxy-2-(5-isoquinolin-4-yl-pyridin-2-yl)-ethylamino]-piperidin-1-yl}-4-trifluoromethyl-thieno[2,3-b]pyridine-2-carboxylic acid amide |

| Structure | Name |
|---|---|
| 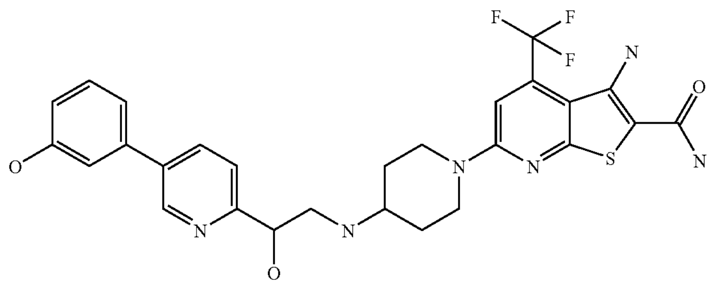 | 3-Amino-6-(4-{2-hydroxy-2-[5-(3-hydroxy-phenyl)-pyridin-2-yl]-ethylamino}-pipendin-1-yl)-4-trifluoromethyl-thieno[2,3-b]pyridine-2-carboxylic acid amide |
| 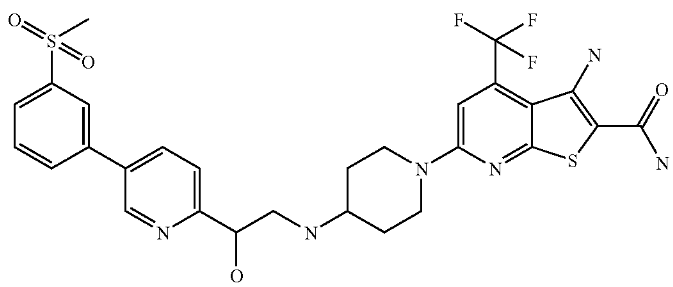 | 3-Amino-6-(4-{2-hydroxy-2-[5-(3-methanesulfonyl-phenyl)-pyridin-2-yl]-ethylamino}-piperidin-1-yl)-4-trifluoromethyl-thieno[2,3-b]pyridine-2-carboxylic acid amide |
| 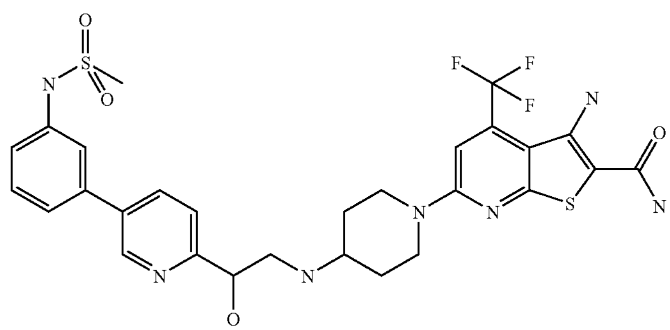 | 3-Amino-6-(4-{2-hydroxy-2-[5-(3-methanesulfonylamino-phenyl)-pyridin-2-yl]-ethylamino}-piperidin-1-yl)-4-trifluoromethyl-thieno[2,3-b]pyridine-2-carboxylic acid amide |
| 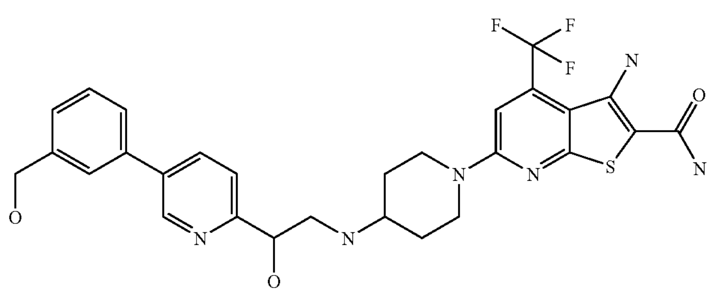 | 3-Amino-6-(4-{2-hydroxy-2-[5-(3-hydroxymethyl-phenyl)-pyridin-2-yl]-ethylamino}-piperidin-1-yl)-4-trifluoromethyl-thieno[2,3-b]pyridine-2-carboxylic acid amide |
| 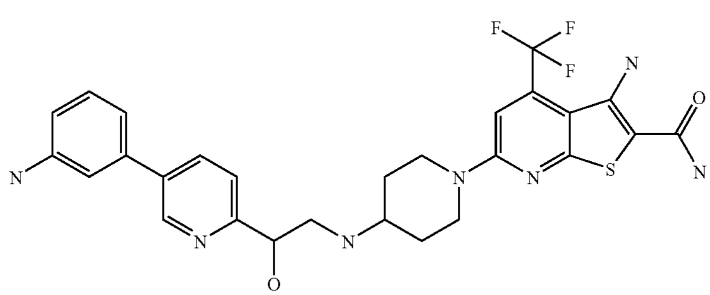 | 3-Amino-6-(4-{2-[5-(3-amino-phenyl)-pyridin-2-yl]-2-hydroxy-ethylamino}-piperidin-1-yl)-4-trifluoromethyl-thieno[2,3-b]pyridine-2-carboxylic acid amide |

-continued

| Structure | Name |
|---|---|
| 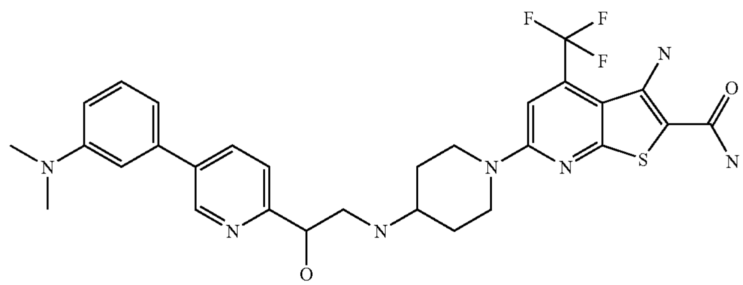 | 3-Amino-6-(4-{2-[5-(3-dimethylamino-phenyl)-pyridin-2-yl]-2-hydroxy-ethylamino}-piperidin-1-yl)-4-trifluoromethyl-thieno[2,3-b]pyridine-2-carboxylic acid amide |
| 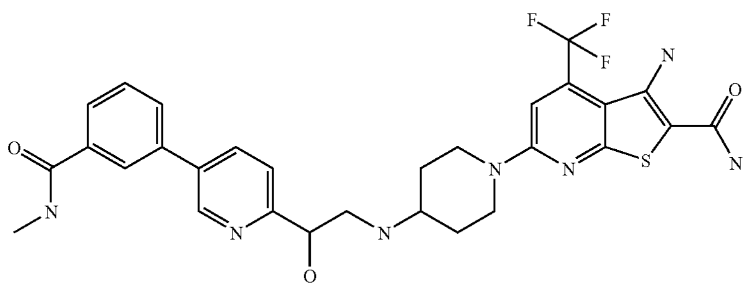 | 3-Amino-6-(4-{2-hydroxy-2-[5-(3-methylcarbamoyl-phenyl)-pyridin-2-yl]-ethylamino)-piperidin-1-yl)-4-trifluoromethyl-thieno[2,3-b]pyridine-2-carboxylic acid amide |
| 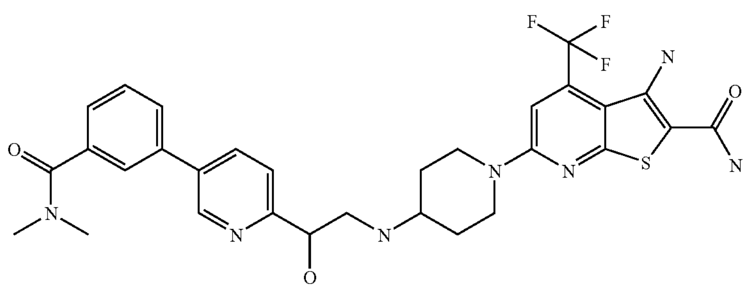 | 3-Amino-6-(4-{2-[5-(3-dimethylcarbamoyl-phenyl)-pyridin-2-yl]-2-hydroxy-ethylamino}-piperidin-1-yl)-4-trifluoromethyl-thieno[2,3-b]pyridine-2-carboxylic acid amide |
| 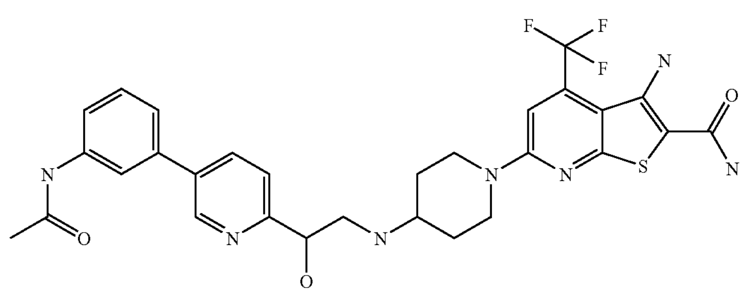 | 6-(4-{2-[5-(3-Acetylamino-phenyl)-pyridin-2-yl]-2-hydroxy-ethylamino}-piperidin-1-yl)-3-amino-4-trifluoromethyl-thieno[2,3-b]pyridine-2-carboxylic acid amide |
| 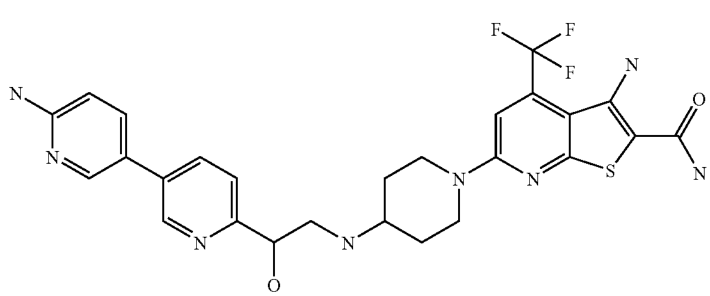 | 3-Amino-6-{4-[2-(6'-amino-3,3']bipyridinyl-6-yl)-2-hydroxy-ethylamino]-piperidin-1-yl}-4-trifluoromethyl-thieno[2,3-b]pyridine-2-carboxylic acid amide |

-continued

| Structure | Name |
|---|---|
| 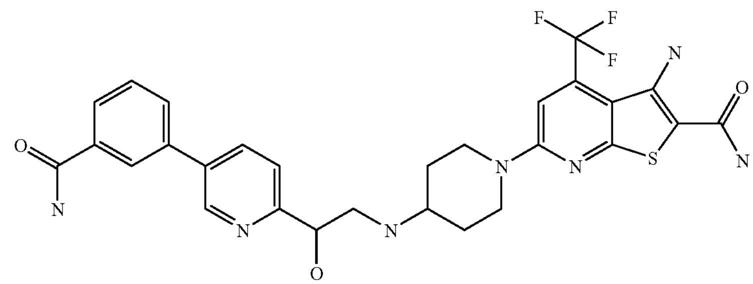 | 3-Amino-6-(4-{2-[5-(3-carbamoyl-phenyl)-pyridin-2-yl]-2-hydroxy-ethylamino}-piperidin-1-yl)-4-trifluoromethyl-thieno[2,3-b]pyridine-2-carboxylic acid amide |
| 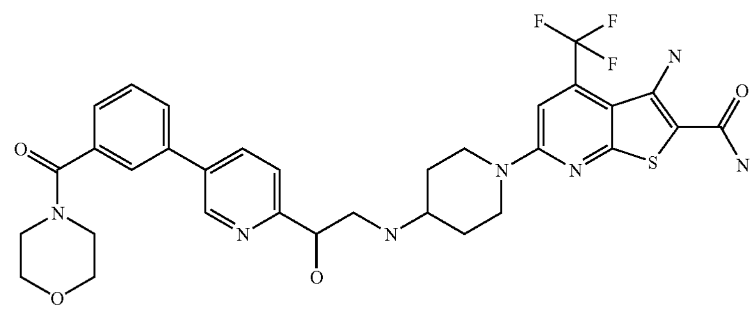 | 3-Amino-6-[4-(2-hydroxy-2-{5-[3-(morpholine-4-carbonyl)-phenyl]-pyridin-2-yl}-ethylamino)-piperidin-1-yl]-4-trifluoromethyl-thieno[2,3-b]pyridine-2-carboxylic acid amide |
| 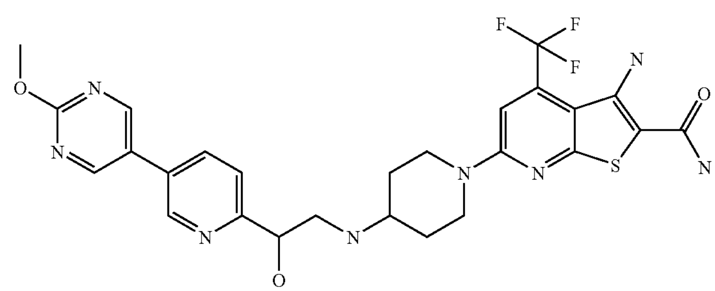 | 3-Amino-6-(4-{2-hydroxy-2-[5-(2-methoxy-pyrimidin-5-yl)-pyridin-2-yl]-ethylamino}-piperidin-1-yl)-4-trifluoromethyl-thieno[2,3-b]pyridine-2-carboxylic acid amide |
| 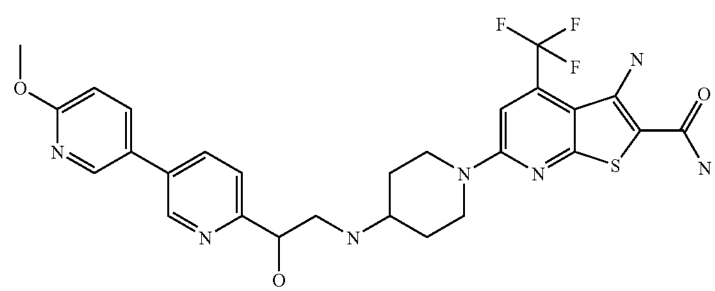 | 3-Amino-6-{4-[2-hydroxy-2-(6'-methoxy-[3,3']bipyridinyl-6-yl)-ethylamino]-piperidin-1-yl}-4-trifluoromethyl-thieno[2,3-b]pyridine-2-carboxylic acid amide |
| 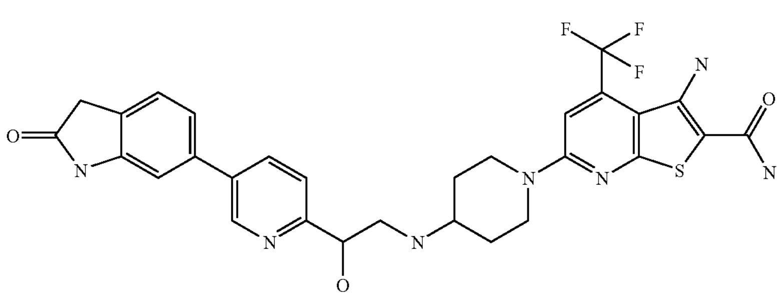 | 3-Amino-6-(4-{2-hydroxy-2-[5-(2-oxo-2,3-dihydro-1H-indol-6-yl)-pyridin-2-yl]-ethylamino}-piperidin-1-yl)-4-trifluoromethyl-thieno[2,3-b]pyridine-2-carboxylic acid amide |

-continued

| Structure | Name |
|---|---|
| 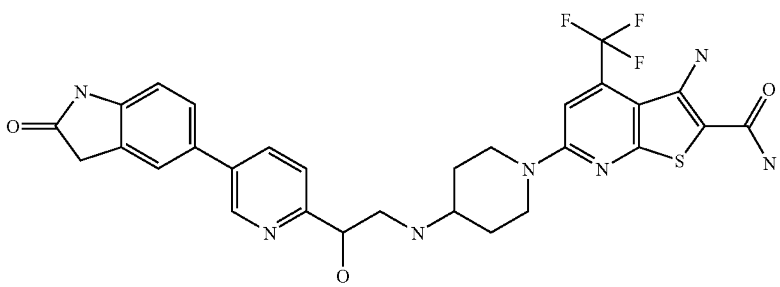 | 3-Amino-6-(4-{2-hydroxy-2-[5-(2-oxo-2,3-dihydro-1H-indol-5-yl)-pyridin-2-yl]-ethylamino}-piperidin-1-yl)-4-trifluoromethyl-thieno[2,3-b]pyridine-2-carboxylic acid amide |
| 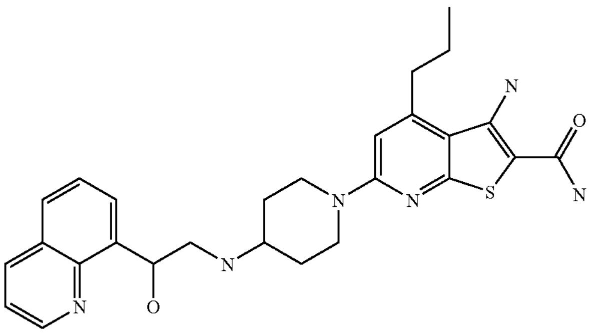 | 3-Amino-6-[4-(2-hydroxy-2-quinolin-8-yl-ethylamino)-piperidin-1-yl]-4-propyl-thieno[2,3-b]pyridine-2-carboxylic acid amide |
| 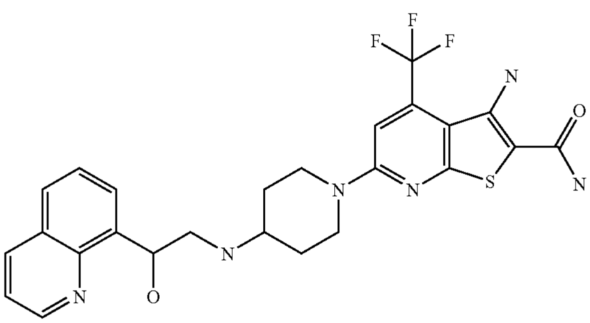 | 3-Amino-6-[4-(2-hydroxy-2-quinolin-8-yl-ethylamino)-piperidin-1-yl]-4-trifluoromethyl-thieno[2,3-b]pyridine-2-carboxylic acid amide |
| 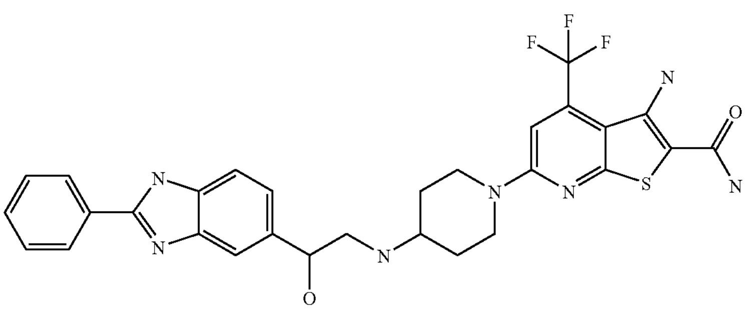 | 3-Amino-6-{4-[2-hydroxy-2-(2-phenyl-1H-benzoimidazol-5-yl)-ethylamino]-piperidin-1-yl}-4-trifluoromethyl-thieno[2,3-b]pyridine-2-carboxylic acid amide |
| 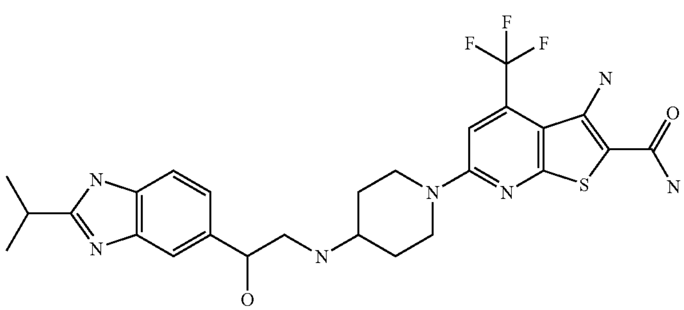 | 3-Amino-6-{4-[2-hydroxy-2-(2-isopropyl-1H-benzoimidazol-5-yl)-ethylamino]-piperidin-1-yl}-4-trifluoromethyl-thieno[2,3-b]pyridine-2-carboxylic acid amide |

-continued

| Structure | Name |
|---|---|
| 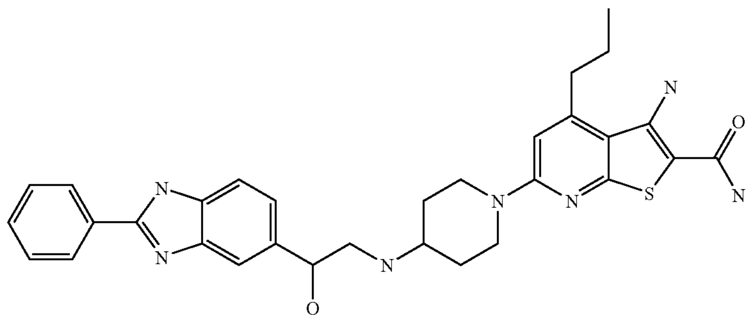 | 3-Amino-6-{4-(2-hydroxy-2-(2-phenyl-1H-benzoimidazol-5-yl)-ethylamino]-piperidin-1-yl}-4-propyl-thieno[2,3-b]pyridine-2-carboxylic acid amide |
| 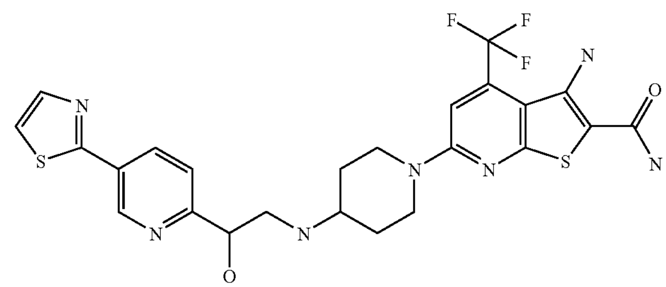 | 3-Amino-6-{4-[2-hydroxy-2-(5-thiazol-2-yl-pyridin-2-yl)-ethylamino]-piperidin-1-yl}-4-trifluoromethyl-thieno[2,3-b]pyridine-2-carboxylic acid amide |
| 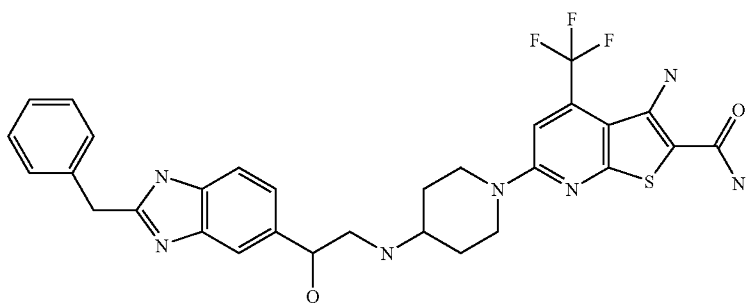 | 3-Amino-6-{4-[2-(2-benzyl-1H-benzoimidazol-5-yl)-2-hydroxy-ethylamino]-piperidin-1-yl}-4-trifluoromethyl-thieno[2,3-b]pyridine-2-carboxylic acid amide |
| 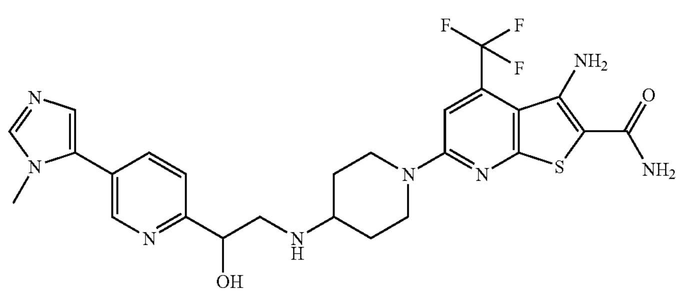 | 3-Amino-6-(4-{2-hydroxy-2-[5-(3-methyl-3H-imidazol-4-yl)-pyridin-2-yl]-ethylamino}-piperidin-1-yl)-4-trifluoromethyl-thieno[2,3-b]pyridine-2-carboxylic acid amide |
| 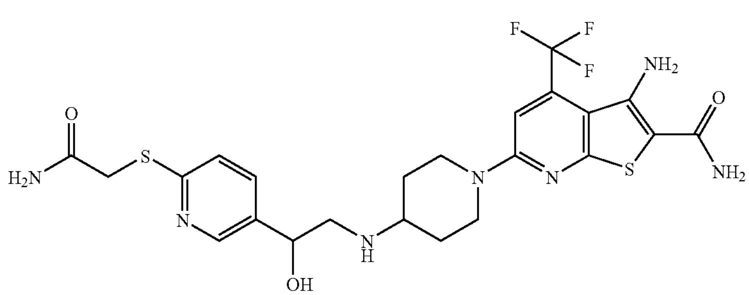 | 3-Amino-6-{4-[2-(6-carbamoylmethylsulfanyl-pyridin-3-yl)-2-hydroxy-ethylamino]-piperidin-1-yl}-4-trifluoromethyl-thieno[2,3-b]pyridine-2-carboxylic acid amide |

| Structure | Name |
|---|---|
| 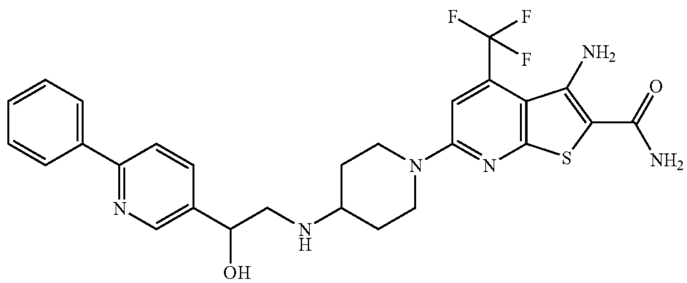 | 3-Amino-6-{4-[2-hydroxy-2-(6-phenyl-pyridin-3-yl)-ethylamino]-piperidin-1-yl}-4-trifluoromethyl-thieno[2,3-b]pyridine-2-carboxylic acid amide |
| 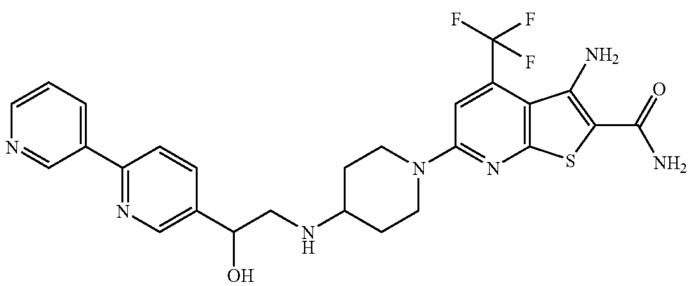 | 3-Amino-6-[4-(2-[2,3']bipyridinyl-5-yl-2-hydroxy-ethylamino)-piperidin-1-yl]-4-trifluoromethyl-thieno[2,3-b]pyridine-2-carboxylic acid amide |
| 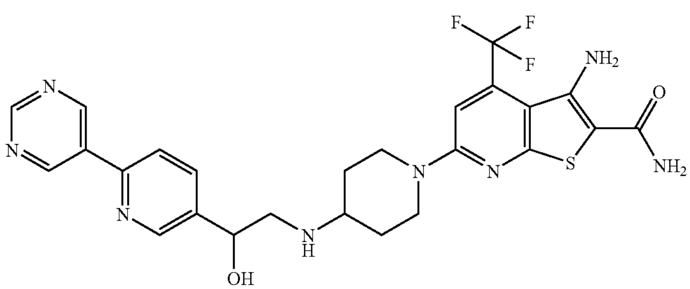 | 3-Amino-6-{4-[2-hydroxy-2-(6-pyrimidin-5-yl-pyridin-3-yl)-ethylamino]-piperidin-1-yl}-4-trifluoromethyl-thieno[2,3-b]pyridine-2-carboxylic acid amide |
| 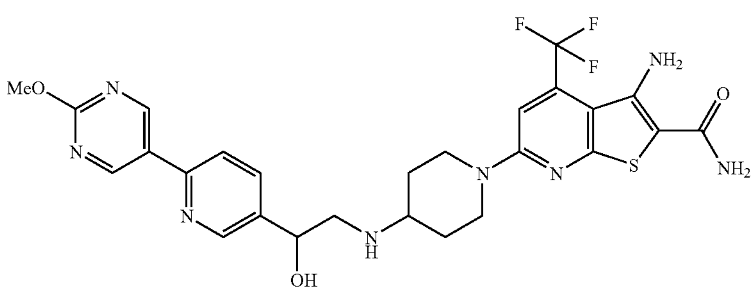 | 3-Amino-6-(4-{2-hydroxy-2-[6-(2-methoxy-pyrimidin-5-yl)-pyridin-3-yl]-ethylamino}-piperidin-1-yl)-4-trifluoromethyl-thieno[2,3-b]pyridine-2-carboxylic acid amide |
| 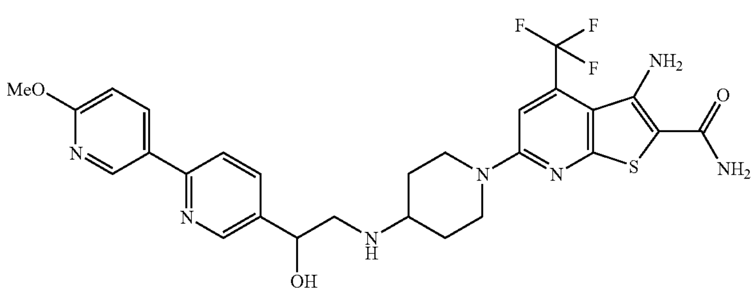 | 3-Amino-6-{4-[2-hydroxy-2-(6'-methoxy-[2,3']bipyridinyl-5-yl)-ethylamino]-piperidin-1-yl}-4-trifluoromethyl-thieno[2,3-b]pyridine-2-carboxylic acid amide |

| Structure | Name |
|---|---|
| (structure) | 3-Amino-6-{4[2-hydroxy-2-(6-quinolin-8-yl-pyridin-3-yl)-ethylamino]-piperidin-1-yl}-4-trifluoromethyl-thieno[2,3-b]pyridine-2-carboxylic acid amide |
| (structure) | 3-Amino-6-{4-[2-(6-bromo-pyridin-3-yl)-2-hydroxy-ethylamino]-piperidin-1-yl}-4-trifluoromethyl-thieno[2,3-b]pyridine-2-carboxylic acid amide |
| (structure) | 3-Amino-6-{4-[2-hydroxy-2-(6-methoxy-pyridin-2-yl)-ethylamino]-piperidin-1-yl}-4-trifluoromethyl-thieno[2,3-b]pyridine-2-carboxylic acid amide | and pharmaceutically acceptable salts, esters, tautomers, individual isomers, and mixtures of isomers thereof.

For all the compounds disclosed in this application, in the event the nomenclature is in conflict with the structure, it shall be understood that the compound is defined by the structure.

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—(C$_1$–C$_4$ alkyl)$_4$$^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:
DMF is dimethylformamide;
DMSO is dimethyl sulfoxide
EtOAc is ethyl acetate;
EtOH is ethanol;
HPLC is high-performance liquid chromatography
MeOH is methanol;
THF is tetrahydrofuran;
TLC is thin layer chromatography Terms not specifically defined herein should be given the meanings that would be given to them by one of skill in the art in light of the disclosure and the context. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched, unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heterocycloalkyl" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydrofuranyl, hexahydropyrimidinyl, hexahydropyridazinyl, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "halogen" refers to bromine, chlorine, fluorine or iodine.

The term "aryl" shall be understood to mean a 6–12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

As used herein above and throughout this application, "nitrogen" and "sulfur" include any oxidized form of nitrogen and sulfur and the quaternized form of any basic nitrogen.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1.

In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory, autoimmune and cardiovascular disorders and cancer. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitus, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Such cardiovascular disorders include but are not limited to atherosclerosis, myocardial infarction and stroke. Such cancers include but are not limited to lymphoid-, myeloid- and epithelial-derived malignancies including leukemia, lymphomas and breast, gastric, colorectal, lung, and pancreatic cancers. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The invention additionally provides for methods for making the compounds of the formula (I). The compounds of the invention may be prepared by the general methods and examples presented below, and methods known to those of ordinary skill in the art. Further reference in this regard may be made to U.S. application Ser. No. 10/453,173, incorporated herein by reference in its entirety. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization. Intermediates used in the Schemes below may be readily prepared by methods known in the art or described in the Synthetic Examples section below.

Compounds of formula I may be prepared by the procedure described in Scheme I.

Scheme I

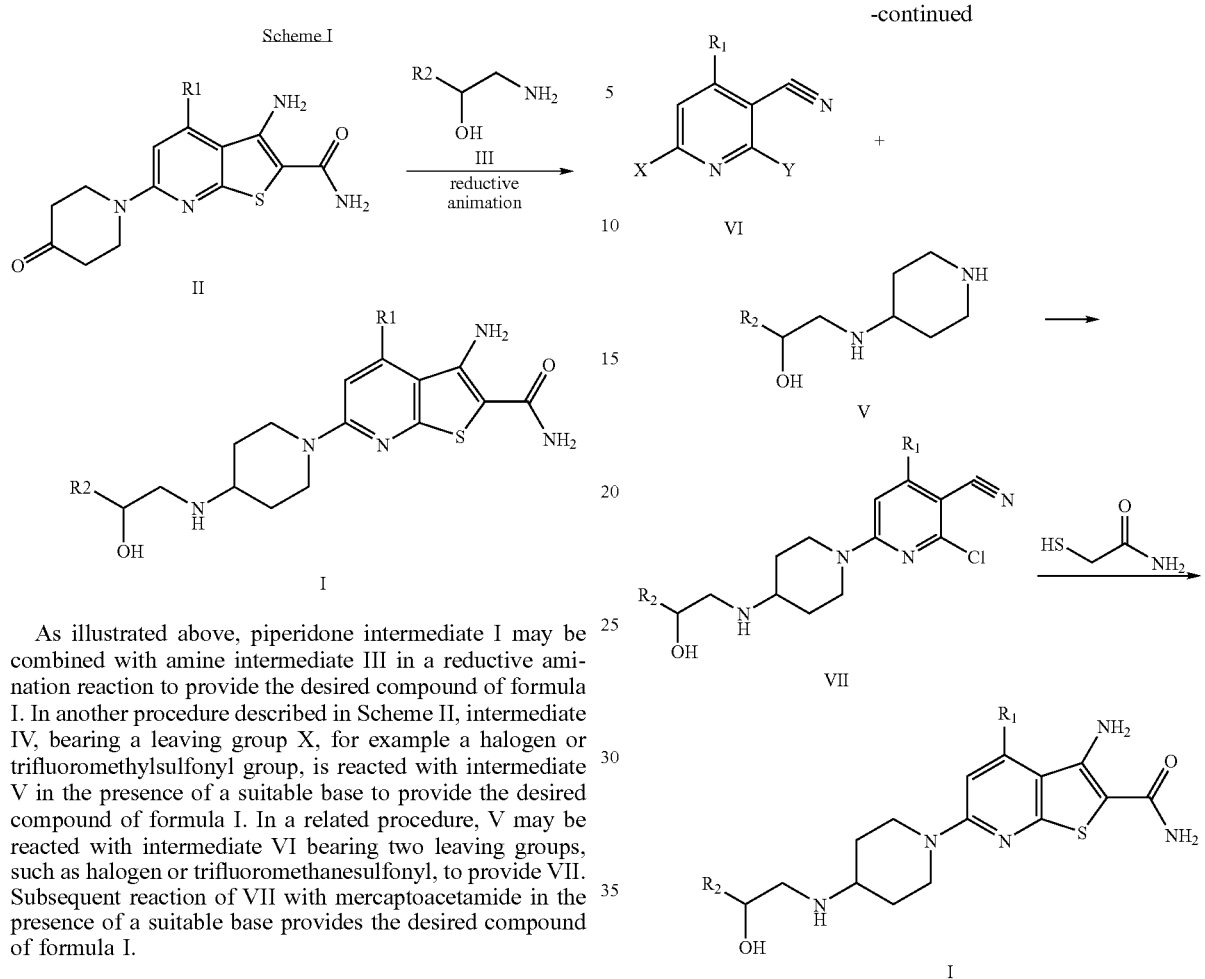

As illustrated above, piperidone intermediate I may be combined with amine intermediate III in a reductive amination reaction to provide the desired compound of formula I. In another procedure described in Scheme II, intermediate IV, bearing a leaving group X, for example a halogen or trifluoromethylsulfonyl group, is reacted with intermediate V in the presence of a suitable base to provide the desired compound of formula I. In a related procedure, V may be reacted with intermediate VI bearing two leaving groups, such as halogen or trifluoromethanesulfonyl, to provide VII. Subsequent reaction of VII with mercaptoacetamide in the presence of a suitable base provides the desired compound of formula I.

Scheme II

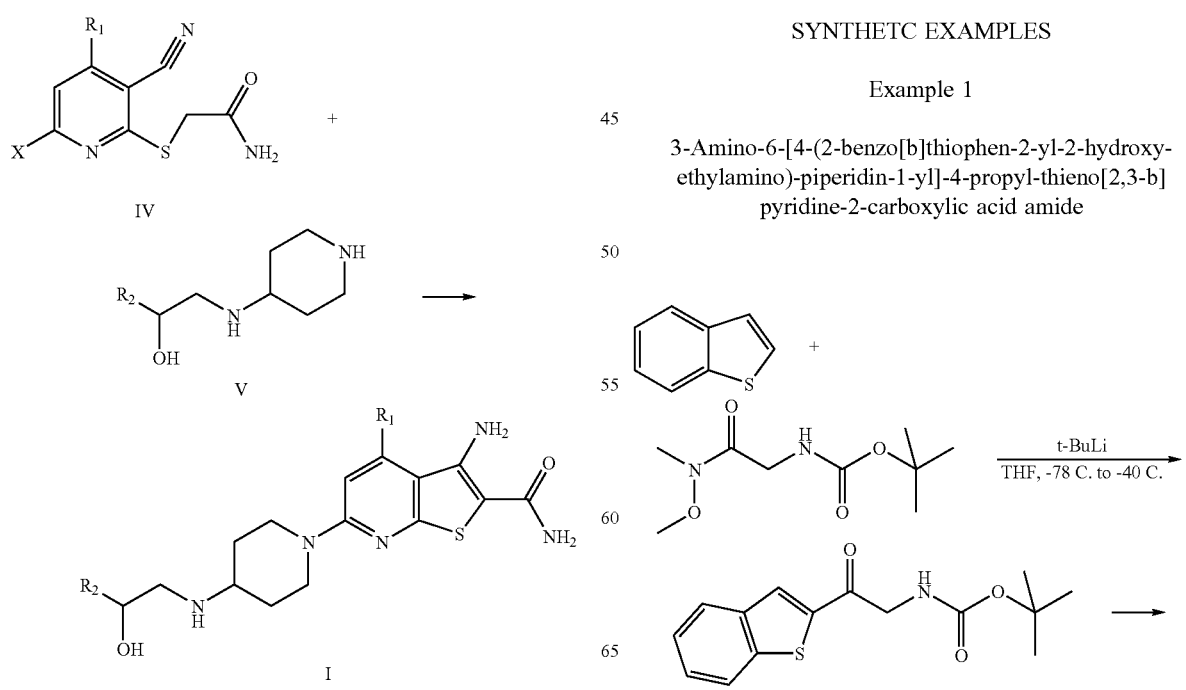

SYNTHETC EXAMPLES

Example 1

3-Amino-6-[4-(2-benzo[b]thiophen-2-yl-2-hydroxy-ethylamino)-piperidin-1-yl]-4-propyl-thieno[2,3-b]pyridine-2-carboxylic acid amide

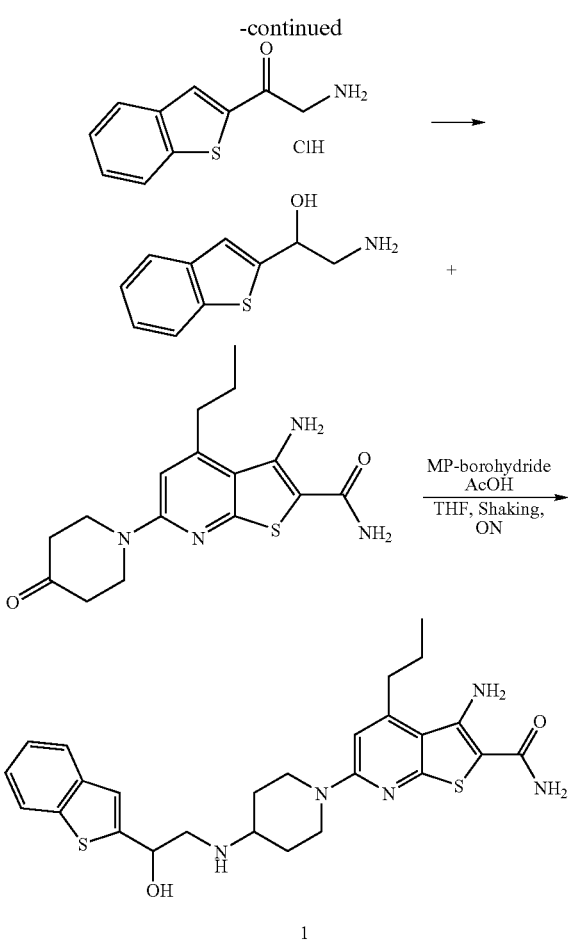

Benzothiophene (671.5 mg, 5.00 mmol) was dissolved into 10 mL of dry THF and cooled to −78° C. To this was added 1.7 M t-BuLi (3.00 mL, 5.10 mmol) in a dropwise fashion. The reaction stirred for 1 h. [(Methoxy-methyl-carbamoyl)-methyl]-carbamic acid tert-butyl ester (545.6 mg, 2.50 mmol) was added in 2.5 mL of dry THF in a dropwise fashion. The reaction was stirred for 2 h, warming to −40° C., then quenched with 15 mL of saturated NH$_4$Cl. The mixture was extracted with 2×20 mL of EtOAc and the organic phase washed with 1×20 mL of brine. The organic phase was dried with MgSO$_4$, filtered and concentrated. The residue was dissolved in CH$_2$Cl$_2$, applied to a SiO$_2$ column and purified (0–10% EtOAc/hexanes) to give 554 mg, 74.7%, of (2-benzo[b]thiophen-2-yl-2-oxo-ethyl)-carbamic acid tert-butyl ester.

(2-Benzo[b]thiophen-2-yl-2-oxo-ethyl)-carbamic acid tert-butyl ester (544 mg, 1.867 mmol) was dissolved into 3 mL of EtOAc and 10 mL of 4.0 M HCl in dioxane was added. The mixture was allowed to stir overnight with a white precipitate forming. The precipitate was triturated with 3×10 mL of EtOAc and dried under vacuum to give 400 mg, 94.7% of crude 2-amino-1-benzo[b]thiophen-2-yl-ethanone HCl salt. The material was carried on without further purification.

The above 2-amino-1-benzo[b]thiophen-2-yl-ethanone HCl salt (400.0 mg, 1.757 mmol) was dissolved into 3 mL of MeOH. The mixture was cooled in a wet ice bath and NaBH$_4$ (128.6 mg, 3.400 mmol) was added in one portion, resulting in H$_2$ formation. After 30 min, the mixture was concentrated to dryness on a rotary evaporator to give an oil. The material was suspended in 6 mL CH$_2$Cl$_2$/hexanes and concentrated to dryness. The cycle was repeated until 2-amino-1-benzo[b]thiophen-2-yl-ethanol was obtained as a gummy solid.

The above 2-amino-1-benzo[b]thiophen-2-yl-ethanol (57.9 mg, 0.300 mmol), 3-amino-6-(4-oxo-piperidin-1-yl)-4-propyl-thieno[2,3-b]pyridine-2-carboxylic acid amide (50.0 mg, 0.15 mmol), MP-borohydride (100 mg) and acetic acid (0.075 mL, 1.31 mmol) were mixed in a 2-dram vial in THF (4 mL) and shaken at room temperature for 21 h overnight. The reaction was filtered, and the borohydride resin was rinsed with MeOH, and then filtered again. The combined filtrates were concentrated in on a rotary evaporator to afford crude product. The residue was dissolved into a minimal amount of MeOH, applied to a 1 mm prep plate (Merck) and eluted with 5% MeOH/CH$_2$Cl$_2$, 1% NH$_3$ to give 21.3 mg, 27.9% of the title compound. ES$^+$ 510.1 m/z (MH$^+$).

The following compounds were also prepared by reaction of the appropriate amine with 3-amino-6-(4-oxo-piperidin-1-yl)-4-propyl-thieno[2,3-b]pyridine-2-carboxylic acid amide as described in Example 1:

3-Amino-6-[4-(2-hydroxy-2-thiazol-2-yl-ethylamino)-piperidin-1-yl]-4-propyl-thieno[2,3-b]pyridine-2-carboxylic acid amide ES$^+$ 460.8 m/z (MH$^+$) was prepared via the methods described in example 1 and Scheme II.

3-Amino-6-[4-(2-hydroxy-2-pyridin-3-yl-ethylamino)-piperidin-1-yl]-4-propyl-thieno[2,3-b]pyridine-2-carboxylic acid amide ES$^+$ 455.4 m/z (MH$^+$). was prepared via the methods described in example 1 and Scheme II.

3-Amino-6-[4-(2-hydroxy-2-pyridin-2-yl-ethylamino)-piperidin-1-yl]-4-propyl-thieno[2,3-b]pyridine-2-carboxylic acid amide ES$^+$ 455 m/z (MH$^+$) was prepared via the methods described in example 1 and Scheme II.

3-Amino-6-[4-(2-hydroxy-2-pyridin-4-yl-ethylamino)-piperidin-1-yl]-4-propyl-thieno[2,3-b]pyridine-2-carboxylic acid amide ES$^+$ 455.4 m/z (MH$^+$) was prepared via the methods described in example 1 and Scheme II.

3-Amino-6-[4-(2-benzo [b]thiophen-3-yl-2-hydroxy-ethylamino)-piperidin-1-yl]-4-propyl-thieno[2,3-b]pyridine-2-carboxylic acid amide ES$^+$ 510.6 m/z (MH$^+$) was prepared via the methods described in example 1 and Scheme II.

3-Amino-6-{4-[2-hydroxy-2-(1-methyl-1H-imidazol-2-yl)-ethylamino]-piperidin-1-yl}-4-propyl-thieno[2,3-b]pyridine-2-carboxylic acid amide ES$^+$ 458.7 m/z (MH$^+$) was prepared via the methods described in example 1 and Scheme II.

3-Amino-6-[4-(2-benzothiazol-2-yl-2-hydroxy-ethylamino)-piperidin-1-yl]-4-propyl-thieno[2,3-b]pyridine-2-carboxylic acid amide ES$^+$ 511.1 m/z (MH$^+$) was prepared via the methods described in example 1 and Scheme II.

3-Amino-6-(4-{2-hydroxy-2-[1-(toluene-4-sulfonyl)-1H-indol-2-yl]-ethylamino}-piperidin-1-yl)-4-propyl-thieno[2,3-b]pyridine-2-carboxylic acid amide ES$^+$ 647.0 m/z (MH$^+$) was prepared via the methods described in example 1 and Scheme II.

3-Amino-6-{4-[2-hydroxy-2-(1-methyl-1H-indol-2-yl)-ethylamino]-piperidin-1-yl}-4-propyl-thieno[2,3-b]pyridine-2-carboxylic acid amide ES$^+$ 507.7 m/z (MH$^+$) was prepared via the methods described in example 1 and Scheme II.

3-Amino-6-{4-[2-hydroxy-2-(1-methyl-1H-benzoimidazol-2-yl)-ethylamino]-piperidin-1-yl}-4-propyl-thieno[2,3-b]

pyridine-2-carboxylic acid amide ES⁺ 508.4 m/z (MH⁺) was prepared via the methods described in example 1 and Scheme II.

3-Amino-6-{4-[2-(1H-benzoimidazol-2-yl)-2-hydroxy-ethylamino]-piperidin-1-yl}-4-propyl-thieno[2,3-b]pyridine-2-carboxylic acid amide ES⁺ 494.1 m/z (MH⁺) was prepared via the methods described in example 1 and Scheme II.

3-Amino-6-{4-[2-hydroxy-2-(1H-imidazol-2-yl)-ethylamino]-piperidin-1-yl}-4-propyl-thieno[2,3-b]pyridine-2-carboxylic acid amide ES⁺ 444.4 m/z (MH⁺) was prepared via the methods described in example 1 and Scheme II.

3-Amino-6-{4-[2-(2,3-dichloro-pyridin-4-yl)-2-hydroxy-ethylamino]-piperidin-1-yl}-4-propyl-thieno[2,3-b]pyridine-2-carboxylic acid amide ES⁺ 523.1 m/z (MH⁺) was prepared via the methods described in example 1 and Scheme II.

3-Amino-6-{4-[2-hydroxy-2-(6-methyl-pyridin-2-yl)-ethylamino]-piperidin-1-yl}-4-propyl-thieno[2,3-b]pyridine-2-carboxylic acid amide ES⁺ 469.6 m/z (MH⁺) was prepared via the methods described in example 1 and Scheme II.

3-Amino-6-(4-{2-hydroxy-2-[4-phenyl-1-(2-trimethylsilanyl-ethoxymethyl)-1H-imidazol-2-yl]-ethylamino}-piperidin-1-yl)-4-propyl-thieno[2,3-b]pyridine-2-carboxylic acid amide ES⁺ 650.8 m/z (MH⁺) was prepared via the methods described in example 1 and Scheme II.

3-Amino-6-{4-[2-hydroxy-2-(5-methyl-pyridin-2-yl)-ethylamino]-piperidin-1-yl}-4-propyl-thieno[2,3-b]pyridine-2-carboxylic acid amide ES⁺ 469.4 m/z (MH⁺) was prepared via the methods described in example 1 and Scheme II.

3-Amino-4-propyl-6-[4-(2-pyridin-2-yl-ethylamino)-piperidin-1-yl]-thieno[2,3-b]pyridine-2-carboxylic acid amide ES⁺ 439.7 m/z (MH⁺) was prepared via the methods described in example 1 and Scheme II.

3-Amino-4-propyl-6-[4-(2-pyridin-3-yl-ethylamino)-piperidin-1-yl]-thieno[2,3-b]pyridine-2-carboxylic acid amide ES⁻437.3 m/z (M−1) was prepared via the methods described in example 1 and Scheme II.

3-Amino-4-propyl-6-[4-(2-pyridin-4-yl-ethylamino)-piperidin-1-yl]-thieno[2,3-b]pyridine-2-carboxylic acid amide ES⁻437.3m/z (M−1) was prepared via the methods described in example 1 and Scheme II.

Example 2

3-Amino-6-[4-(2-hydroxy-2-thiophen-3-yl-ethylamino)-piperidin-1-yl]-4-propyl-thieno[2,3-b]pyridine-2-carboxylic acid amide

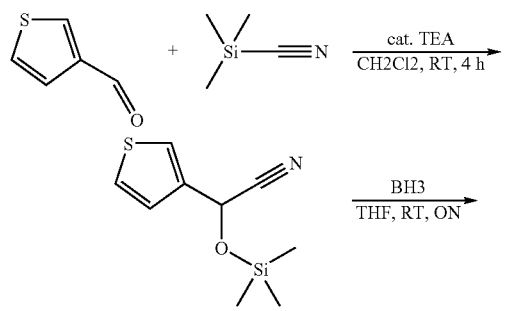

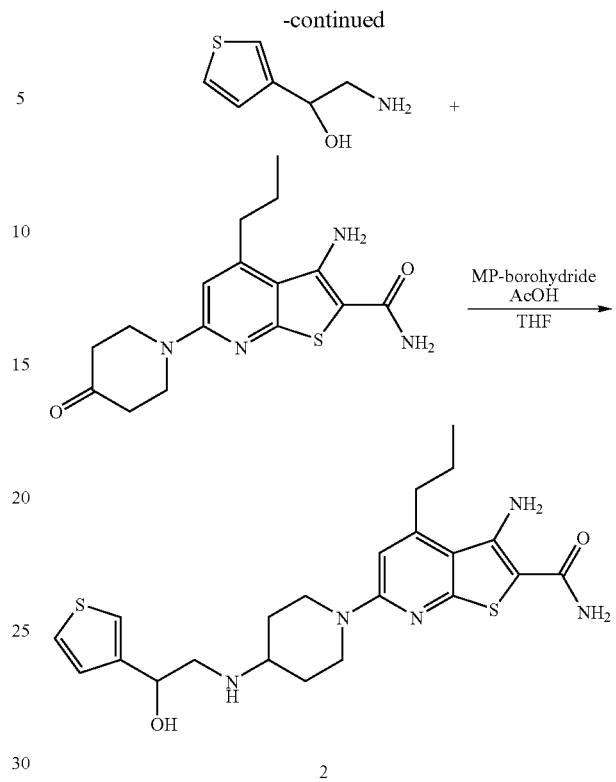

3-Thiophene carboxaldehyde (0.438 mL, 5.000 mmol) was dissolved into dry CH₂Cl₂ and placed under argon. To this was added trimethylsilyl cyanide (0.933 mL, 7.000 mmol) and triethylamine (0.070 mL, 0.500 mmol). The reaction mixture was allowed to stir for 4 h. The mixture was concentrated on a rotary evaporator to dryness to give thiophen-3-yl-trimethylsilanyloxy-acetonitrile as a clear oil.

The above thiophen-3-yl-trimethylsilanyloxy-acetonitrile was dissolved into 5 mL of dry THF. To this was added a 1.0 M solution of BH₃/THF (7.00 mL, 7.00 mmol). The reaction was stirred overnight. The mixture was concentrated on a rotary evaporator. The residue was dissolved into 10 mL of MeOH and concentrated on a rotary evaporator with heating. This cycle was repeated 4 times. The resulting crude amine was then carried on to the title compound using the procedure described in Example 1. ES⁺ 460.2 m/z (MH⁺).

Example 3

3-Amino-6-{4-[2-(5-cyano-pyridin-2-yl)-2-hydroxy-ethylamino]-piperidin-1-yl}-4-propyl-thieno[2,3-b]pyridine-2-carboxylic acid amide was prepared by method 6, method 1, [2-(5-Cyano-pyridin-2-yl)-2-hydroxy-ethyl]-carbamic acid tert-butyl ester was prepared in the following manner.

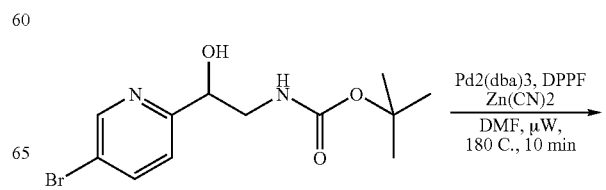

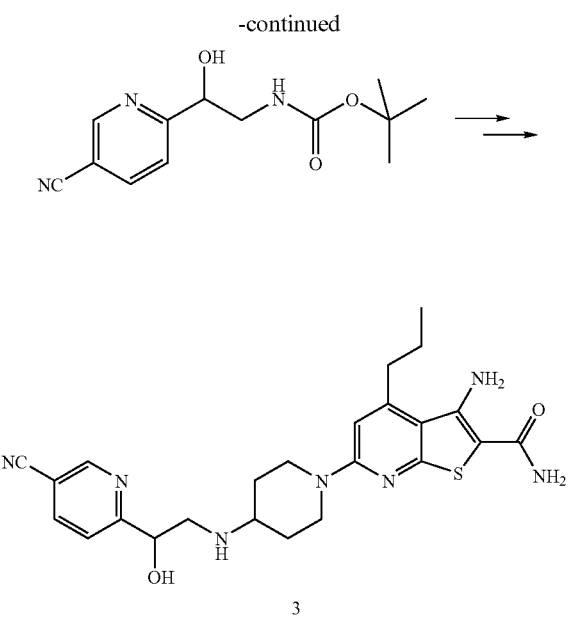

2-(5-Bromo-pyridin-2-yl)-2-hydroxy-ethyl]-carbamic acid tert-butyl ester (310 mg, 0.977 mmol), trisdibenzylidene bispalladium (22.9 mg, 0.025 mmol), 1,1'-Bis(diphenylphosphino)ferrocene (DPPF) (27.1, 0.049 mmol) and zinc cyanide (274 mg, 2.34 mmol) were placed in a microwave tube and sealed with 3 mL of dry DMF. The tube was heated in the Smith Synthesizer™ (Personal Chemistry) at 180° C. for 10 min. After cooling, the reaction mixture was diluted with 30 mL of EtOAc. The organic phase was washed with 2×20 mL H$_2$O and 1×20 mL of brine, dried with MgSO$_4$, filtered and concentrated. The residue was dissolved in CH$_2$Cl$_2$, applied to a SiO$_2$ column and purified (25–50% EtOAc/hexanes) to give 152.1 mg, 52% of [2-(5-cyano-pyridin-2-yl)-2-hydroxy-ethyl]-carbamic acid tert-butyl ester.

3-Amino-6-{4-[2-(5-cyano-pyridin-2-yl)-2-hydroxy-ethylamino]-piperidin-1-yl}-4-propyl-thieno[2,3-b]pyridine-2-carboxylic acid amide was prepared from the above amine using the procedure described in Example 1. ES$^+$ 480.3 m/z (MH$^+$).

Example 4

3-Amino-6-{4-[2-(6-cyano-pyridin-2-yl)-2-hydroxy-ethylamino]-piperidin-1-yl}-4-propyl-thieno[2,3-b]pyridine-2-carboxylic acid amide

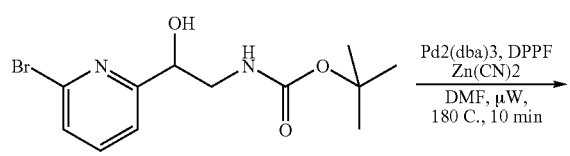

2-(6-Bromo-pyridin-2-yl)-2-hydroxy-ethyl]-carbamic acid tert-butyl ester (447.0 mg, 1.504 mmol), trisdibenzylidene bispalladium (33.9 mg, 0.037 mmol), DPPF (41.1, 0.075 mmol) and zinc cyanide (423.0 mg, 3.61 mmol) were placed in a microwave tube and sealed with 3 mL of dry DMF. The tube was heated in the Smith synthesizer™ (Personal Chemistry) at 180° C. for 10 min. After cooling, the reaction mixture was diluted with 30 mL of EtOAc. The organic phase was washed with 2×20 mL H$_2$O and 1×20 mL of brine. The organic phase was dried with MgSO$_4$, filtered and concentrated, the residue dissolved in CH$_2$Cl$_2$ applied to a SiO$_2$ column and purified (25–50% EtOAc/hexanes) to give 147.5 mg, 37.2% of [2-(6-cyano-pyridin-2-yl)-2-hydroxy-ethyl]-carbamic acid tert-butyl ester and 126.0, 28% of [2-(6-carbamoyl-pyridin-2-yl)-2-hydroxy-ethyl]-carbamic acid tert-butyl ester.

[2-(6-Cyano-pyridin-2-yl)-2-hydroxy-ethyl]-carbamic acid tert-butyl ester was deprotected by treatment with acid as described in Example 1. 3-Amino-6-{4-[2-(6-cyano-pyridin-2-yl)-2-hydroxy-ethylamino]-piperidin-1-yl}-4-propyl-thieno[2,3-b]pyridine-2-carboxylic acid amide was prepared via the procedure in Example 1. ES$^+$ 480.3 m/z (MH$^+$).

3-Amino-6-{4-[2-(6-carbamoyl-pyridin-2-yl)-2-hydroxy-ethylamino]-piperidin-1-yl}-4-propyl-thieno[2,3-b]pyridine-2-carboxylic acid amide was prepared by the deprotection of [2-(6-carbamoyl-pyridin-2-yl)-2-hydroxy-ethyl]-carbamic acid tert-butyl ester and further reaction by the procedure described in Example 1. ES$^+$ 498.3 m/z (MH$^+$).

Example 5
3-Amino-6-{4-[2-(5-benzylcarbamoyl-pyridin-2-yl)-2-hydroxy-ethylamino]-piperidin-1-yl}-4-propyl-thieno[2,3-b]pyridine-2-carboxylic acid amide
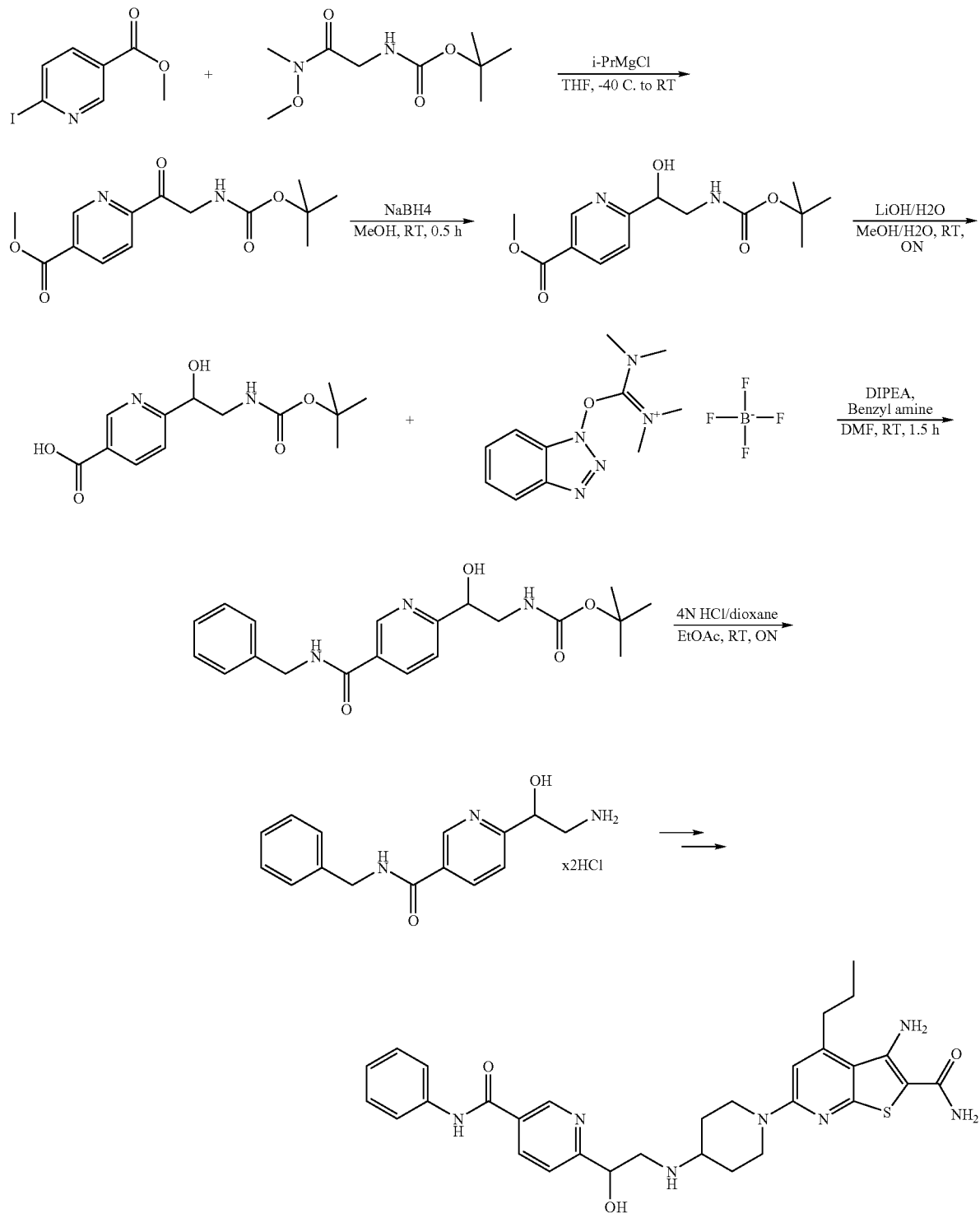

To 6-iodo-nicotinic acid methyl ester in 10 mL of dry THF at −40° C. was added a 2 M solution of i-propylmagnesium chloride (4.33 mL, 8.60 mmol) in a dropwise fashion. The reaction was allowed to stir for 1 h, warming to 0° C. The flask was cooled to −40° C. and [(methoxy-methyl-carbamoyl)-methyl]-carbamic acid tert-butyl ester was added in one portion. The reaction mixture was allowed to warm to room temperature over a 3 h period and stirred an additional h. The reaction was quenched with saturated NH₄Cl and 50 mL of EtOAc was added. The organic phase was washed with 2×20 mL H₂O and 1×20 mL of brine, dried (MgSO₄), filtered and concentrated. The residue was dissolved in CH₂Cl₂, applied to a SiO₂ column and purified (0–20% EtOAc/hexanes) to give 132.7 mg as a mixture of 6-(2-tert-butoxycarbonylamino-acetyl)-nicotinic acid methyl ester to nicotinic acid methyl ester (3.2/.0.18).

6-(2-tert-Butoxycarbonylamino-acetyl)-nicotinic acid methyl ester (132.7 mg, 0.451 mmol) was dissolved into 3 mL of MeOH. To this was added sodium borohydride (18.96 mg, 0.50 mmol) in one portion. After 0.5 h, the reaction mixture was concentrated on a rotary evaporator. The residue was dissolved into 20 mL of EtOAc. The organic phase was washed with 2×20 mL NH₄Cl and 1×20 mL of brine, dried (MgSO₄) filtered and concentrated to give 133 mg, 99.5% of 6-(2-tert-butoxycarbonylamino-1-hydroxy-ethyl)-nicotinic acid methyl ester.

6-(2-tert-Butoxycarbonylamino-1-hydroxy-ethyl)-nicotinic acid methyl ester (137.3 mg, 0.450 mmol) was dissolved into 3 mL of MeOH. To this was added LiOH monohydrate (56.5, 1.350 mmol). The reaction stirred at room temperature overnight. The reaction mixture was concentrated on a rotary evaporator, dissolved into 2 mL of water, and brought to pH 4 with AcOH. The mixture was extracted into 3×10 mL of EtOAc and the organic fractions combined. The organic phase was washed with 2×20 mL H₂O and 1×20 mL of brine, dried MgSO₄, filtered and concentrated to give 130 mg of 6-(2-tert-butoxycarbonylamino-1-hydroxy-ethyl)-nicotinic acid.

6-(2-tert-Butoxycarbonylamino-1-hydroxy-ethyl)-nicotinic acid (130 mg, 0.461 mmol), diisopropylethylamine (DIPEA) (0.426 mL, 2.44 mmol), [(benzotriazol-1-yloxy)-dimethylamino-methylene]-dimethyl-ammonium tetrafluoroborate (319 mg, 1.00 mmol), and benzyl amine (0.246 mL, 2.30 mmol) were dissolved into 3 mL of dry DMF and stirred overnight. LC-MS indicated formation of the coupled product. The mixture was diluted with 30 mL of EtOAc, the organic phase washed with 2×20 mL H₂O and 1×20 mL of brine, dried (MgSO₄) filtered and concentrated. The residue was dissolved in CH₂Cll₂, applied to a SiO₂ column and purified (10–30% EtOAc/hexanes) to give 47.8, 27.9% of [2-(5-benzylcarbamoyl-pyridin-2-yl)-2-hydroxy-ethyl]-carbamic acid tert-butyl ester.

[2-(5-Benzylcarbamoyl-pyridin-2-yl)-2-hydroxy-ethyl]-carbamic acid tert-butyl ester (47.0 mg, 0.129 mmol) was dissolved into 2 mL of EtOAc and 4.0 N HCl in dioxane (1.0 mL, 4 mmol) was added. The reaction was allowed to stir overnight. The resulting precipitate was triturated with 3×5 mL of THF and concentrated on a rotary evaporator to dryness to give 43 mg of 6-(2-amino-1-hydroxy-ethyl)-N-benzyl-nicotinamide 2HCl.

3-Amino-6-{4-[2-(5-benzylcarbamoyl-pyridin-2-yl)-2-hydroxy-ethylamino]-piperidin-1-yl}-4-propyl-thieno[2,3-b]pyridine-2-carboxylic acid amide was prepared from the above amine using the procedure described in Example 1. ES⁺ 588.3 m/z (MH⁺).

Example 6

3-Amino-6-{4-[2-hydroxy-2-(2-methylsulfanyl-pyrimidin-4-yl)-ethylamino]-piperidin-1-yl}-4-propyl-thieno[2,3-b]pyridine-2-carboxylic acid amide

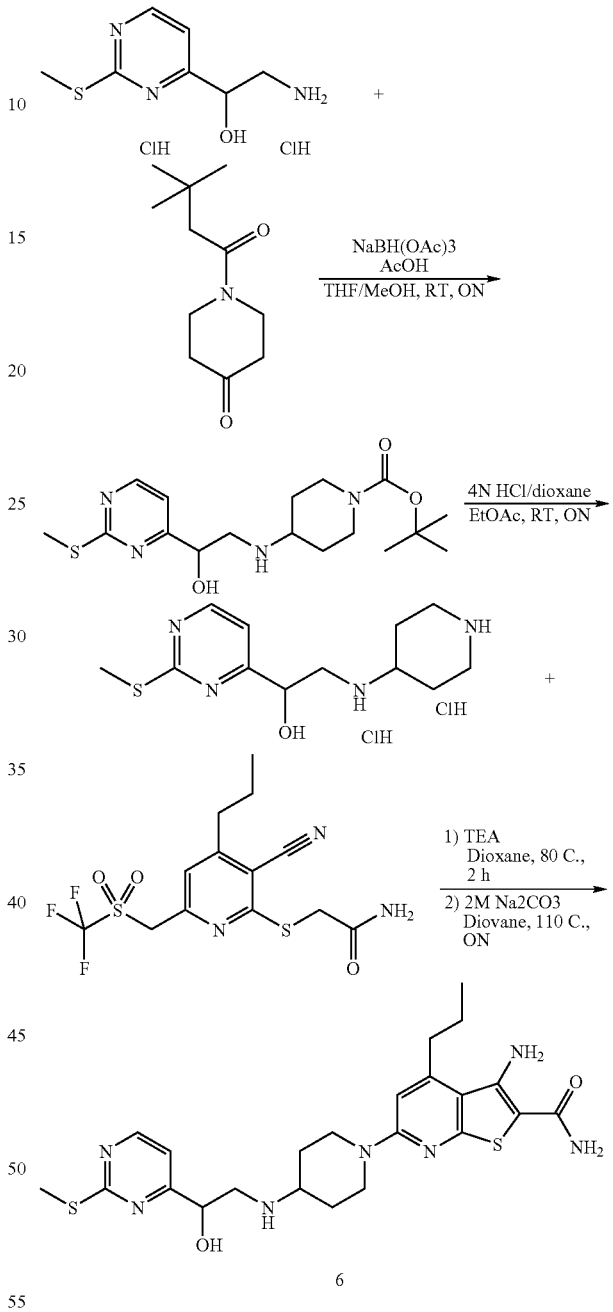

6

2-Amino-1-(2-methylsulfanyl-pyrimidin-4-yl)-ethanol dihydrochloride salt (0.339 g, 1.83 mmol) was dissolved into a minimum of MeOH and diluted with 10 mL of THF. To this was added t-butyl-4-oxo-1-piperidinecarboxylate (0.478 g, 2.40 mmol), AcOH (0.458 mL, 8.00 mmol) and sodium triacetoxyborohydride (1.696 g, 8.00 mmol) and the reaction was stirred overnight. LC-MS analysis indicated complete consumption of the starting material. The mixture was concentrated on a rotary evaporator, the residue dissolved in CH₂Cl₂ and applied to a SiO₂ column and purified (0–10% MeOH/CH₂Cl₂) to give 511.0 mg, 57.8% yield of 4-[2-hydroxy-2-(2-methylsulfanyl-pyrimidin-4-yl)-ethylamino]-piperidine-1-carboxylic acid tert-butyl ester.

4-[2-Hydroxy-2-(2-methylsulfanyl-pyrimidin-4-yl)-ethylamino]-piperidine-1-carboxylic acid tert-butyl ester (510.0 mg, 1.387 mmol) was dissolved into 3 mL of EtOAc and 3 mL of 4.0 M HCl in dioxane was added. The mixture was allowed to stir overnight with a white precipitate forming. The precipitate was triturated with 3×10 mL of EtOAc and dried under vacuum to give 441.4 mg, 93.2% of crude 1-(2-methylsulfanyl-pyrimidin-4-yl)-2-(piperidin-4-ylamino)-ethanol dihydrochloride salt. The material was carried on without further purification.

The above amino alcohol dihydrochloride salt (268.36 mg, 0.700 mmol), DIPA (0.610 mL, 3.50 mmol) and triflate (200 mg, 0.586 mmol) were dissolved into 10 mL of dioxane and heated at 80° C. for 2h. To the reaction mixture was added 5 mL of a 2.5 M $Na_2CO_3$ solution. The mixture was refluxed overnight. After cooling, the reaction mixture was diluted with 100 mL of EtOAc. The organic phase was washed with 2×50 mL $H_2O$ and 1×50 mL of brine, dried $Mg_2SO4$, filtered and concentrated to give a tan residue which was triturated with 3×10 mL of EtOAc to give 153.2 mg, 52%, of the title compound. $ES^+$502.4 m/z ($MH^+$).

Example 7

3-Amino-6-{4-[2-hydroxy-2-(1-methyl-1H-benzoimidazol-2-yl)-ethylamino]-piperidin-1-yl}-4-trifluoromethyl-thieno[2,3-b]pyridine-2-carboxylic acid amide

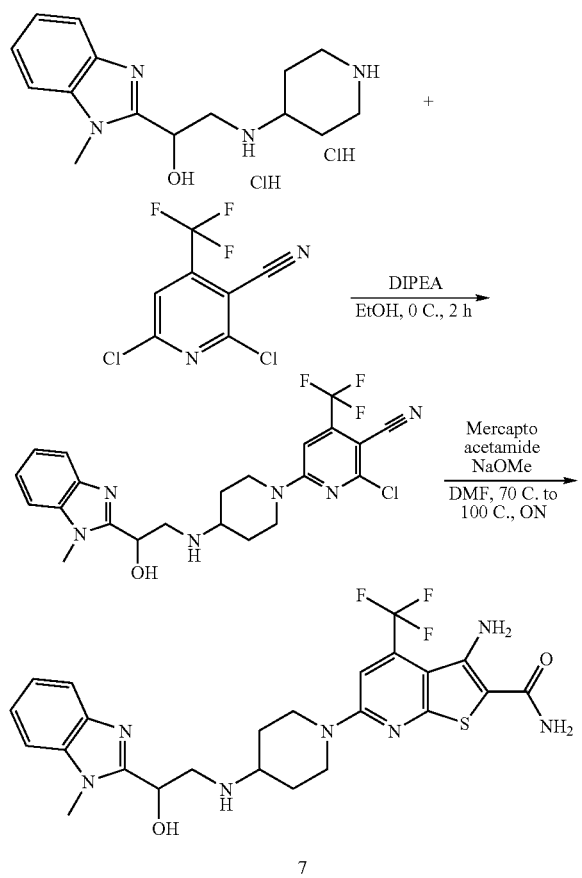

2,6-Dichloro-4-trifluoromethyl-nicotinonitrile (277 mg, 1.15 mmol) was dissolved into 10 mL of absolute EtOH and cooled in a wet ice bath. To this was added DIPEA (1.74 mL, 10 mmol) and 1-(1-methyl-1H-benzoimidazol-2-yl)-2-(piperidin-4-ylamino)-ethanol dihydrochloride (400 mg, 1.15 mmol). The mixture was stirred for 2 h. LC-MS anlysis indicated formation of the product. The reaction mixture was concentrated on a rotary evaporator and the residue was dissolved in $CH_2Cl_2$ and applied to a $SiO_2$ column and purified (0–10% MeOH/CH2Cl2) to give an oil, still contaminated with DIPEA. Trituration with EtOAc gave 344 mg, 62.4% of 6'-chloro4-[2-hydroxy-2-(1-methyl-1H-benzoimidazol-2-yl)-ethylamino]-4'-trifluoromethyl-3,4,5,6-tetrahydro-2H-[1,2']bipyridinyl-5'-carbonitrile.

6'-Chloro-4-[2-hydroxy-2-(1-methyl-1H-benzoimidazol-2-yl)-ethylamino]-4'-trifluoromethyl-3,4,5,6-tetrahydro-2H-[1,2']bipyridinyl-5'-carbonitrile (344.0 mg, 0.718) mmol was dissolved into 2 mL of dry DMF. To this was added a 1.09 M MeOHic solution of mercaptoacetamide (1.00 mL, 1.09 mmol) and a 1 M solution of MeOHic NaOMe (2.87 mL, 2.87 mmols). The reaction mixture was heated at 60° C. for 2 h. LC-MS indicated complete conversion to the mercaptoacetamide adduct. The reaction was then heated at 80° C. overnight. The reaction mixture was concentrated on a rotary evaporator with heating to 70° C. to give a dark orange oil. The oil was dissolved into a minimal amount of MeOH, applied to a $SIO_2$ column and eluted with 0–10% MeOH/$CH_2Cl_2$ and 0–10% MeOH/CH2Cl2-1% NH3) to give 213.7 mg, 55.8%, of the title compound. $ES^+$ 534.3 m/z ($MH^+$)

The following compounds were also prepared by using methods described in the preceeding examples:

3-Amino-6-{4-[2-hydroxy-2-(2-methylsulfanyl-pyrimidin-4-yl)-ethylamino]-piperidin-1-yl}-4-trifluoromethyl-thieno[2,3-b]pyridine-2-carboxylic acid amide $ES^+$ 528.5 m/z ($MH^+$) was prepared via the methods described in example 6 and Scheme II.

3-Amino-6-{4-[2-hydroxy-2-(6-methyl-pyridin-2-yl)-ethylamino]-piperidin-1-yl}-4-trifluoromethyl-thieno[2,3-b]pyridine-2-carboxylic acid amide $ES^+$ 495.3 m/z ($MH^+$). was prepared via the methods described in example 6 and Scheme II.

Example 8

3-Amino-6-[4-(2-hydroxy-2-quinolin-3-yl-ethylamino)-piperidin-1-yl]-4-propyl-thieno[2,3-b]pyridine-2-carboxylic acid amide

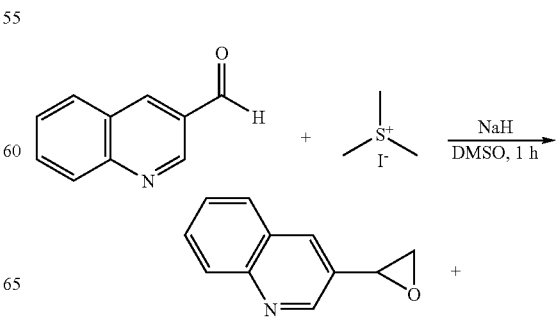

-continued

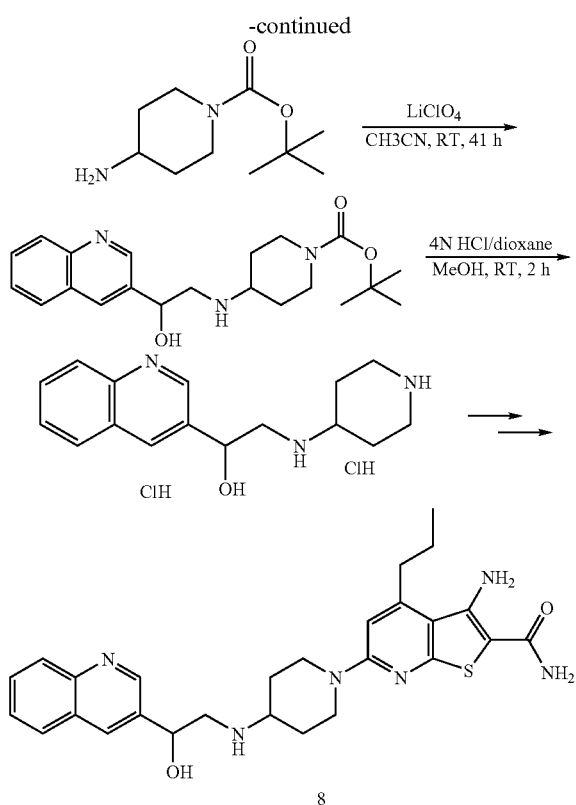

To a suspension of sodium hydride (60% in mineral oil, 480 mg, 12 mmol) in dry DMSO (5 mL) was added slowly a solution of trimethylsulfonium iodide (2.66 g, 13 mmol) in 12 mL dry DMSO at room temperature. After stirring for 5 min at room temperature, a solution of 3-quinolinecarboxaldehyde (300 mg, 1.91 mmol) in 7 mL DMSO was added. After addition of the aldehyde was complete, the solution changed from colorless to yellow, then to brownish green. Reaction progress was followed by LC-MS. After 1.5 h at room temperature, the reaction mixture was quenched with ice water and extracted with $CH_2Cl_2$ three times. The combined organic extracts were washed twice with brine, dried ($Na_2SO_4$) and filtered. The solvent was removed in vacuo to afford a brown oil that was purified by flash column chromatography on $SiO_2$ using $MeOH/CH_2Cl_2$ mixtures as eluent providing 190 mg of clean epoxide (1.11 mmol, 58% of theory) as a light yellow oil.

The quinoline epoxide obtained above (190 mg, 1.11 mmol) was dissolved in 5 mL anhydrous $CH_3CN$. 4-Amino-piperidine-1-tert-butyl-carboxylate (238 mg, 1.19 mmol) and lithium perchlorate (127 mg, 1.19 mmol) were added. The resulting suspension was diluted further with 10 mL $CH_3CN$ and stirred at room tremperature overnight, then in a 60° C. oil bath for 41 h. The solvent was removed in vacuo and the residue was partitioned between EtOAc and water. The aqueous layer was extracted once with EtOAc and the combined organics were washed with brine, dried ($Na_2SO_4$), filtered and concentrated in vacuo. The crude material was purified by flash column chromatography on $SiO_2$ using $MeOH/CH_2Cl_2$ mixtures as eluent to provide a colorless oil, which was dissolved in 5 mL MeOH and treated with 5 mL 4N HCl in dioxane. After 2 h TLC showed starting material was completely consumed. The solvent was removed in vacuo providing 265 mg of the dihydrochloride salt (0.77 mmol, 69% of theory) as a light yellow foam.

3-Amino-6-[4-(2-hydroxy-2-quinolin-3-yl-ethylamino)-piperidin-1-yl]-4-propyl-thieno[2,3-b]pyridine-2-carboxylic acid amide was prepared by the method described in Example 6 (mp: 213–216° C., ES$^+$ 505 m/z (MH$^+$)).

3-Amino-6-[4-(2-hydroxy-2-quinolin-4-yl-ethylamino)-piperidin-1-yl]-4-propyl-thieno[2,3-b]pyridine-2-carboxylic acid amide was prepared via the methods described in example 8 and Scheme II starting from 4-quinoline-carboxaldehyde. mp: 170–172° C., ES$^+$ 505 m/z (MH$^+$).

3-Amino-6-[4-(2-hydroxy-2-quinolin-2-yl-ethylamino)-piperidin-1-yl]-4-propyl-thieno[2,3-b]pyridine-2-carboxylic acid amide was prepared via the methods described in example 8 and Scheme II starting from 2-quinoline-carboxaldehyde. mp: 159–161° C., ES$^+$ 505 m/z (MH$^+$).

Example 9

3-Amino-6-[4-(2-hydroxy-2-pyridin-3-yl-ethylamino)-piperidin-1-yl]-4-trifluoromethyl-thieno[2,3-b]pyridine-2-carboxylic acid amide

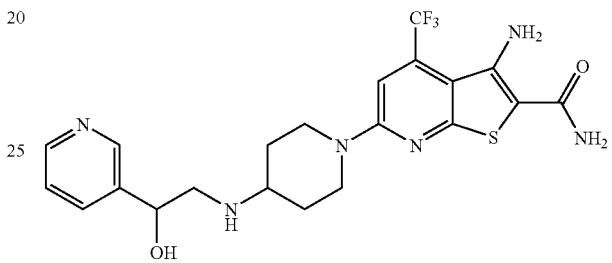

In a round-bottom flask 2-(3-pyridyl)-2-hydroxy-1-ethylamine (1.516 g, 10.97 mmol) was dispersed in 40 mL anhydrous dichloroethane. To this suspension was added tert-butyl 4-oxo-piperidine-1-carboxylate (1.822 g, 9.14 mmol) and glacial acetic acid (1.57 mL, 27.5 mmol). The mixture was stirred at room temperature for 20 min. Then sodium triacetoxy-borohydride was added (12.111 g, 57.14 mmol). The mixture was diluted with 10 mL $CH_3CN$ and stirred at room temperature over two days.

The reaction mixture was quenched with saturated NaHCO$_3$ solution and stirred for 30 min. It was then diluted with water and extracted with $CH_2Cl_2$ three times. The combined organic extracts were washed with brine, dried (MgSO$_4$), filtered, and the solvent was removed in vacuo. The residue was dissolved in $CH_2Cl_2$ and loaded onto a flash silica gel chromatography column. Purification using MeOH/CH$_2$Cl$_2$ mixtures as eluent afforded 1.017 g of the Boc-protected piperidine as a yellow oil (35% of theory).

The Boc-protected piperidine (1.017 g, 3.16 mmol) was dissolved in a round-bottom flask in 30 mL MeOH. To this was added 10 mL 4N HCl in dioxane (40 mmol) and the mixture was stirred at room temperature for 35 min. The progress of the reaction was followed by TLC (10% MeOH/ dichloromethane). The solvent was removed in vacuo to afford 1.07 mg of a pink foam, which was used without further purification.

The substituted 4-amino-piperidine dihydrochloride salt obtained above (931 mg, 3.16 mmol) was dispersed in 40 mL EtOH at 0° C. Added 2,6-dichloro-3-cyano-5-trifluoromethyl-pyridine (763 mg, 3.16 mmol) and then, dropwise, added Hunig's base (2.21 mL, 12.66 mmol). The mixture was stirred at 0° C. for 1 h. TLC showed complete conversion. The solvent was removed in vacuo and the residue was loaded onto a flash silica gel chromatography column. Purification using MeOH/dichloromethane mixtures as eluent afforded 709 mg of desired monochloro-pyridine as an orange foam (53% of theory).

In a round-bottom flask, the chloro-pyridine obtained above (709 mg, 1.67 mmol) was dissolved in 7 mL DMF. To this was added 2-mecaptoacetamide (10% in methanolic ammonia, 3.0 mL, 3.33 mmol) and 6.7 mL 0.5 M NaOMe in MeOH (3.4 mmol). Stirred at room temperaturefor 1 h, then added another 6.7 mL 0.5 M NaOMe in MeOH (3.4 mmol) and stirred overnight in 60° C. oil bath. Removed solvent under high vacuum, added water and extracted with EtOAc three times. Washed combined organics with brine, dried (Na$_2$SO$_4$), filtered, and removed solvent in vacuo. The residue was triturated in hot MeOH, and filtered through a Buchner funnel. The crude product was purified by flash column chromatography on SiO$_2$ using MeOH/dichloromethane mixtures as eluent. The title compound was obtained as a bright yellow solid, 305 mg (38% of theory). m.p.: 179–181° C., ES$^+$ 481 m/z (MH$^+$).

3-Amino-6-[4-(2-hydroxy-2-pyridin-2-yl-ethylamino)-piperidin-1-yl]-4-trifluoromethyl-thieno[2,3-b]pyridine-2-carboxylic acid amide was prepared via the methods described in example 9 and Scheme II starting from 2-(2-pyridyl)-2-hydroxy-1-ethylamine. mp: 201–202° C., ES$^+$ 481 m/z (MH$^+$).

3-Amino-6-[4-(2-hydroxy-2-pyridin-4-yl-ethylamino)-piperidin-1-yl]-4-trifluoromethyl-thieno[2,3-b]pyridine-2-carboxylic acid amide was prepared via the methods described in example 9 and Scheme II starting from 2-(4-pyridyl)-2-hydroxy-1-ethylamine. mp: 217–220° C., ES$^+$ 481 m/z (MH$^+$).

Example 10

3-Amino-6-[4-(2-hydroxy-2-quinolin-2-yl-ethylamino)-piperidin-1-yl]-4-trifluoromethyl-thieno[2,3-b]pyridine-2-carboxylic acid amide

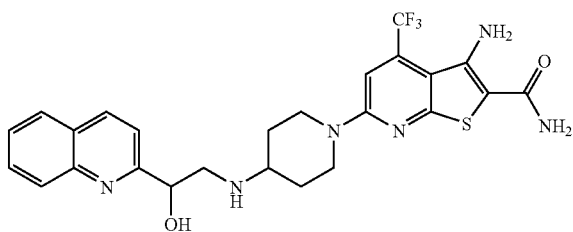

To a suspension of sodium hydride (60% in mineral oil, 800 mg, 20.0 mmol) in dry DMSO (5 mL) was added slowly a solution of trimethylsulfonium iodide (4.428 g, 21.7 mmol) in 21 mL dry DMSO at room temperature. After stirring for 5 min, to the solution was added a solution of 2-quinoline-carboxaldehyde (500 mg, 3.18 mmol) in 7 mL DMSO. The color of the mixture changed from colorless to yellow, then green. Reaction progress was followed by LC-MS and after 40 min was quenched with ice water. Extraction of the aqueous layer three times with CH$_2$Cl$_2$, and washing of the combined organics with brine, afforded a green solution. This was dried (Na$_2$SO$_4$), filtered, and the solvent was removed in vacuo. The residue was dissolved in CH$_2$Cl$_2$ and purified by flash column chromatography on SiO$_2$ using MeOH/dichloromethane mixtures as eluent. Thus were obtained 232 mg of the desired epoxide, as a yellow oil (42.6% of theory).

In a round bottom flask containing 4 mL anhydrous CH$_3$CN was dissolved the 2-quinoline epoxide obtained above (232 mg, 1.36 mmol). The 4-amino-piperidine-1-tert-butyl-carboxylate (290 mg, 1.45 mmol) was then added, followed by LiClO$_4$ (154 mg, 1.45 mmol). The addition is accompanied by a color change from yellow to orange. The mixture was diluted with 4 mL more anhydrous CH$_3$CN, stirred in a 60° C. oil bath overnight, then diluted with water and extracted with EtOAc three times. The combined organics were washed with brine, dried (Na$_2$SO$_4$), and filtered. The solvent was removed in vacuo and the residue was purified by flash column chromatography on SiO$_2$ using MeOH/dichloromethane mixtures as eluent. The pure substituted amino-piperidine was obtained as a yellow oil, 368 mg (73% of theory).

The Boc-protected piperidine obtained above (368 mg, 0.991 mmol) was dissolved in 10 mL MeOH. To this solution was added 5 mL 4N HCl in dioxane, and the mixture was left stirring at room temperature overnight. Removal of the solvent in vacuo afforded 386 mg of the dihydro-chloride salt as a yellow foam, which was used in the next step without purification.

The piperidine dihydrochloride salt obtained above (341 mg, 0.991 mmol) was dispersed in 20 mL absolute EtOH. The mixture was cooled to 0° C. and treated with the dichloro-pyridine (239 mg, 0.991 mmol), then Hunigs base was added dropwise to the resulting solution. After 1 h the solvent was removed in vacuo to yield a light yellow solid. Trituration in CH$_2$Cl$_2$, followed by filtration afforded 414 mg of monochloro-pyridine as a white solid (88% of theory).

In a round-bottom flask was dispersed in 7 mL DMSO the monocholoro-pyridine from above (412 mg, 0.866 mmol). To this mixture was added mercapto-acetamide (10% in methanolic ammonia, 0.95 mL, 1.04 mmol), followed by 2.1 mL 0.5 M sodium methoxide in MeOH. The mixture was stirred at room temperature for 3 h, then heated with stirring in a 60° C. oil bath. Another portion of sodium methoxide solution (2.1 mL) was added, and stirring was continued at 60° C. overnight. The solvent was removed under high vacuum to afford a bright yellow solid which was triturated in hot MeOH. Filtration through a vacuum Buchner funnel afforded 209 mg of pure, title compound (46% of theory). mp: 198–201° C., ES$^+$ 531 m/z (MH$^+$).

3-Amino-6-[4-(2-hydroxy-2-quinolin-3-yl-ethylamino)-piperidin-1-yl]-4-trifluoromethyl-thieno[2,3-b]pyridine-2-carboxylic acid amide was prepared via the methods described in example 10 and Scheme II starting from 3-quinoline-carboxaldehyde. ES$^+$ 531 m/z (MH$^+$).

3-Amino-6-[4-(2-hydroxy-2-quinolin-4-yl-ethylamino)-piperidin-1-yl]-4-trifluoromethyl-thieno[2,3-b]pyridine-2-carboxylic acid amide was prepared via the methods described in example 10 and Scheme II starting from 4-quinoline-carboxaldehyde. ES$^+$ 531 m/z (MH$^+$).

Example 11

3-Amino-6-[4-(2-hydroxy-2-isoquinolin-3-yl-ethylamino)-piperidin-1-yl]-4-propyl-thieno[2,3-b]pyridine-2-carboxylic acid amide

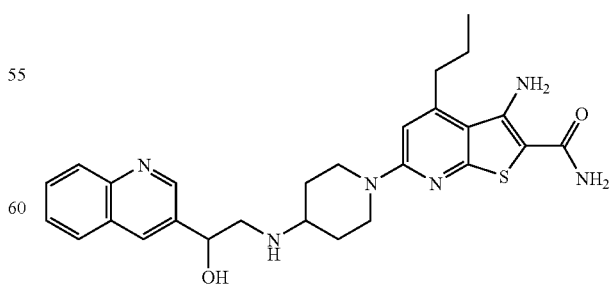

Methyl 3-isoquinoline carboxylate (1.50 g, 8.01 mmol) was placed in 60 ML anhydrous toluene and cooled to 0° C. The solution was treated dropwise with 1M DIBAL solution in toluene (8.2 mL, 8.2 mmol). The solution gradually changed from colorless to yellow and then orange during addition. After 2 h another 2 mL 1M DIBAL solution in toluene was added and the mixture was left stirring another 1 h at 0–10° C. The mixture was then quenched with aqueous Na K tartrate solution, stirred 15 min then diluted with brine and EtOAc. The layers were separated and the aqueous was extracted twice with EtOAc. The combined organics were washed with brine repeatedly (emulsion), dried (MgSO$_4$), filtered and the solvent was removed in vacuo. An orange oil was thus obtained, which was purified by flash column chromatography on SiO$_2$ using CH$_2$Cl$_2$/MeOH eluent mixtures. The desired isoquinoline carboxaldehyde was isolated as a yellow solid, 420 mg (33% of theory).

To a suspension of sodium hydride (60% in mineral oil, 0.792 g, 19.8 mmol) in dry DMSO (18 mL) was added slowly a solution of trimethylsulfonium iodide (4.3 g, 21.1 mmol) in 25 mL anhydrous DMSO at room temperature. After stirring for 5 min, the isoquinoline carboxaldehyde obtained above (520 mg, 3.31 mmol) was added as a solution in 2 mL anhydrous DMSO. The mixture was left stirring at room temperature for 1 h, then poured into ice water and extracted three times with CH$_2$Cl$_2$. The combined organic extracts were washed with brine and dried (Na$_2$SO$_4$), filtered and the solvent was removed in vacuo. The crude material was purified by column chromatography on SiO$_2$ using MeOH in dichloromethane as eluent. This afforded 319 mg of desired epoxide as a dark yellow oil.

The isoquinoline epoxide obtained above (319 mg, 1.86 mmol) and 4-amino-piperidine-1-tert-butyl-carboxylate (373 mg, 1.86 mmol) were combined in 7 mL anhydrous acetonitrile and treated with lithium perchlorate solid (198 mg, 1.86 mmol). The mixture was left stirring at room temperature for 1 day and at 60° C. overnight. The final color of the solution was orange. The mixture was quenched with dilute NaHCO$_3$ aqueous solution and extracted three times with EtOAc. The combined organics were washed with brine, dried (Na$_2$SO$_4$), filtered, and the solvent was removed in vacuo to afford an orange foam. This crude material was purified by flash column chromatography on SiO$_2$ using mixtures of dichloromethane and MeOH as eluent. The substituted amino-Boc-protected piperidine (375 mg) was isolated as a yellow foam. $^1$H NMR was consistent with desired regioisomer.

The Boc-piperidine obtained above (375 mg, 1.01 mmol) was dissolved in 30 mL MeOH and treated at room temperature with 4M HCl in 1,4-dioxane (8.75 mL). The mixture was left stirring at room temperature overnight. Removal of solvents in vacuo afforded the dihydrochloride salt as a pale yellow foam, 439 mg. This was used without purification in the next step.

The above isoquinolinyl-ethylamino-piperidine dihydrochloride salt (160 mg, 0.52 mmol) was dispersed in 4 mL anhydrous 1,4-dioxane. Triethylamine (0.73 mL, 5.2 mmol) was added and the mixture was stirred 5 min. Pyridine-triflate was added (250 mg, 0.65 mmol) and the mixture was diluted with 4 mL more dioxane. The reaction tube was placed in a 70° C. oil bath and stirred overnight. The reaction mixture was cooled and treated with 2M Na$_2$CO$_3$ aqueous solution. The tube was then sealed and the 2-phase mixture stirred vigorously at 100° C. for 7 h. After cooling, water was added and the mixture was extracted with EtOAc three times. The combined organics were washed with brine, dried (Na$_2$SO$_4$), filtered, and the solvent was removed in vacuo. A yellow-brown oil, 315 mg was obtained. This crude material was purified by flash column chromatography on SiO$_2$ using MeOH in dichloromethane mixtures to afford 98 mg of a tan foam. Trituration from hot MeOH afforded the title compound as a white solid, 62 mg (24% of theory). mp: 213–215° C. (dec), ES$^+$ 505 m/z (MH$^+$).

3-Amino-6-[4-(2-hydroxy-2-isoquinolin-3-yl-ethylamino)-piperidin-1-yl]-4-trifluoromethyl-thieno[2,3-b]pyridine-2-carboxylic acid amide was prepared via the methods described in example 11 and Scheme II starting from methyl-3-isoquinoline carboxylate. mp: 169–172° C., ES$^+$ 531 m/z (MH$^+$).

3-Amino-6-[4-(2-hydroxy-2-isoquinolin-1-yl-ethylamino)-piperidin-1-yl]-4-propyl-thieno[2,3-b]pyridine-2-carboxylic acid amide was prepared via the methods described in example 11 and Scheme II starting from methyl-1-isoquinoline carboxylate. mp: <150° C., ES$^+$ 505 m/z (MH$^+$).

3-Amino-6-[4-(2-hydroxy-2-isoquinoln-1-yl-ethylamino)-piperidin-1-yl]-4-trifluoromethyl-thieno[2,3-b]pyridine-2-carboxylic acid amide was prepared via the methods described in example 8, example 3 and Scheme II starting from methyl-1-isoquinoline carboxylate. ES$^+$ 531 m/z (MH$^+$).

3-Amino-6-[4-(2-hydroxy-2-quinolin-6-yl-ethylamino)-piperidin-1-yl]-4-propyl-thieno[2,3-b]pyridine-2-carboxylic acid amide was prepared via the methods described in example 11 and Scheme II starting from methyl-6-quinoline carboxylate. ES$^+$ 505 m/z (MH$^+$).

3-Amino-6-[4-(2-hydroxy-2-quinolin-6-yl-ethylamino)-piperidin-1-yl]-4-trifluoromethyl-thieno[2,3-b]pyridine-2-carboxylic acid amide was prepared via the methods described in example 11 and Scheme II starting from methyl-6-quinoline carboxylate. mp: 217–219° C, ES$^+$ 531 m/z (MH$^+$).

Example 12

3-Amino-6-[4-(2-hydroxy-2-pyrazin-2-yl-ethylamino)-piperidin-1-yl]-4-propyl-thieno[2,3-b]pyridine-2-carboxylic acid amide

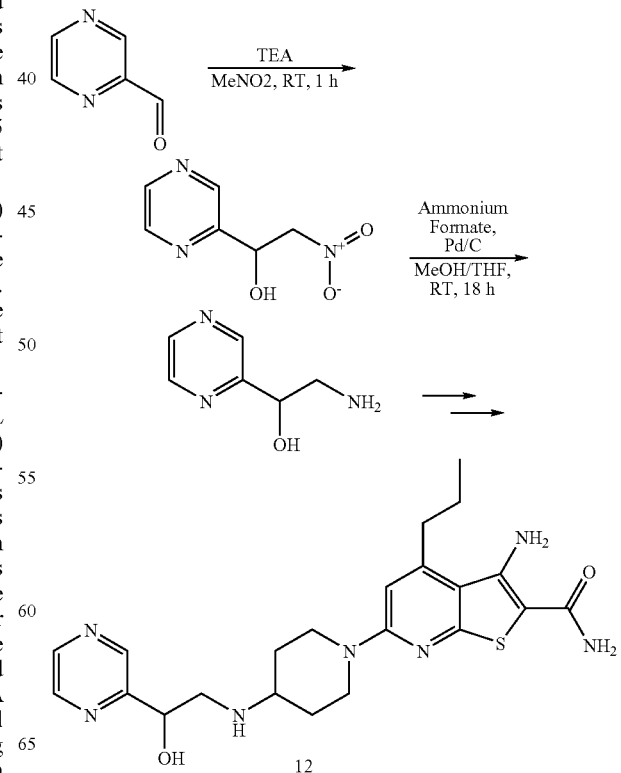

To a round bottom flask was added 2-pyrazinecarboxaldehyde (770 mg, 7.12 mmol) in 10 mL of nitromethane, followed by the addition of triethylamine (721 mg, 7.12 mmol). The reaction mixture was stirred at room temperature for 1 h. The reaction mixture was concentrated in vacuo. The residue was loaded onto a flash chromatography column. The column was eluted with 0–5% MeOH/CH$_2$Cl$_2$. The product fractions were collected and concentrated to afford 1124 mg (93.3%) of 2-nitro-1-pyrazin-2-yl-ethanol. (TLC: Rf=0.2, 5% MeOH/CH$_2$Cl$_2$, UV).

To a round bottom flask was added 2-nitro-1-pyrazin-2-yl-ethanol (1012 mg, 6 mmol), ammonium formate (1886 mg, 30 mmol) and palladium 10% on activated carbon (220 mg) in 40 mL of MeOH and 40 mL of THF. The reaction mixture was stirred at room temperature for 18 h. The reaction mixture was filtered through diatomaceous earth and concentrated in vacuo. The residue was loaded onto a flash chromatography column. The column was eluted with 0–5% 2M NH$_3$ in MeOH/CH$_2$Cl$_2$. The product fractions were collected and concentrated to afford 480 mg (57.7%) of yellow solid 2-amino-1-pyrazin-2-yl-ethanol. (TLC: Rf=0.15, 5% 2M NH$_3$ in MeOH/CH$_2$Cl$_2$, UV). MH$^+$=140.3. The above intermediate was carried on to the final compound using the procedure described in Example 6. MH$^+$=456.42

3-Amino-6-[4-(2-hydroxy-2-pyrazin-2-yl-ethylamino)-piperidin-1-yl]-4-trifluoromethyl-thieno[2,3-b]pyridine-2-carboxylic acid amide was prepared via the methods described in example 12 and Scheme II. ES$^+$ 482.41 m/z (MH$^+$)

Example 13

Trifluoro-methanesulfonic acid 6-carbamoylmethyl-sulfanyl-5-cyano-4-cyclopropyl-pyridin-2-yl ester

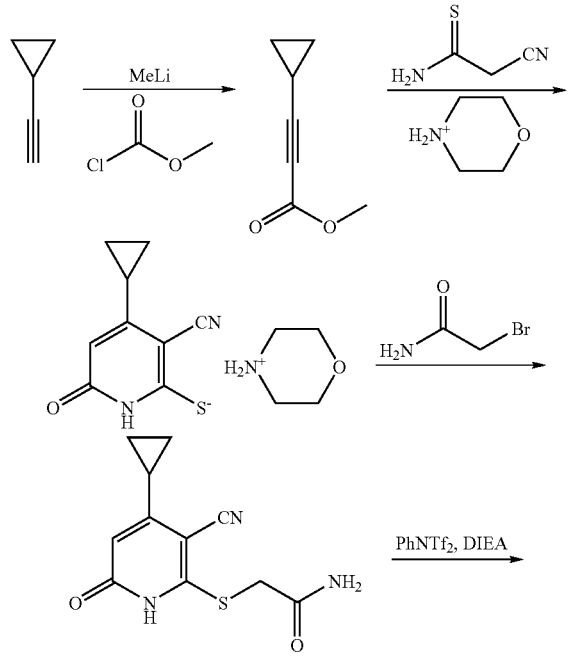

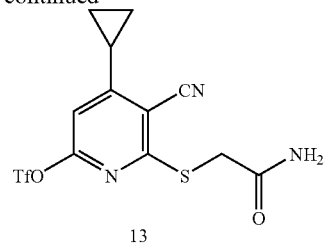

To a solution of cyclopropyl acetylene (10.0 g, 148 mmol) in 50 mL of ethyl ether at −78° C. under argon was added methyllithiium (1.4 M in ethyl ether, 107 mL, 150 mmol). This solution was stirred at −78° C. for 1 h. Methyl chloroformate (12.0 mL, 154 mmol) was added. The reaction mixture was warmed to room temperature in 2 h and was quenched with water. The organic layer was separated. The aqueous layer was extracted with ethyl ether (50 mL×3). The combined organic layer was dried over sodium sulfate and evaporated to give cyclopropyl-propynoic acid methyl ester as a yellow oil (13.25 g, 72%).

To a solution of cyclopropyl-propynoic acid methyl ester 1 (13.25 g, 0.107 mol) in 300 mL of absolute EtOH was added morpholine (9.7 mL, 0.11 mol) at room temperature under argon. This solution was heated at 45° C. for 40 min. 2-Cyanothoioacetamide (11.36 g, 0.110 mol) was added. This mixture was heated at 60° C. for 1.5 h. A yellow precipitate was formed. After standing at room temperature for 16 h, 3-cyano-4-cyclopropyl-6-oxo-1,6-dihydro-pyridine-2-thiol morpholine salt (15.02 g, 50%) was collected by filtration, washed with EtOH and then dried under vacuum at room temperature for 20 h.

3-Cyano-4-cyclopropyl-6-oxo-1,6-dihydro-pyridine-2-thiol morpholine salt (15.00 g, 53.69 mmol) was suspended in 15 mL of dry DMF. 2-Bromoacetamide (7.74 g, 55.0 mmol) was added. This mixture was stirred at room temperature for 30 min and quenched with water. The resultant solid was collected by filtration, washed with water and dried under high vacuum for 24 h to give 2-(3-cyano-4-cyclopropyl-6-oxo-1,6-dihydro-pyridin-2-ylsulfanyl)-acetamide as a pale colored solid (13.22 g, 99%)

2-(3-Cyano-4-cyclopropyl-6-oxo-1,6-dihydro-pyridin-2-ylsulfanyl)-acetamide (13.22 g, 53.03 mmol) and N-phenyl-trifluoromethanesulfonimide (20.00 g, 55.42 mmol) was suspended/dissolved in 100 mL of dichloromethane. Diisopropylethylamine (10.00 mL, 56.83 mmol) was added. This mixture was stirred at room temperature for 4 h. The title compound was collected by filtration and washed with dichloromethane. Yield: 17.80 g 88%. (ES$^+$ 382 m/z (MH$^+$).

Example 14

Trifluoro-methanesulfonic acid 6-carbamoylmethyl-sulfanyl-5-cyano-4-ethyl-pyridin-2-yl ester

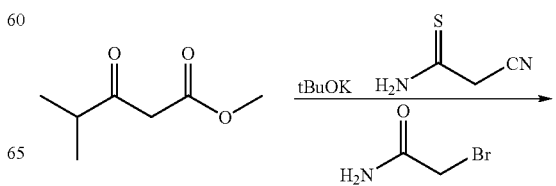

-continued

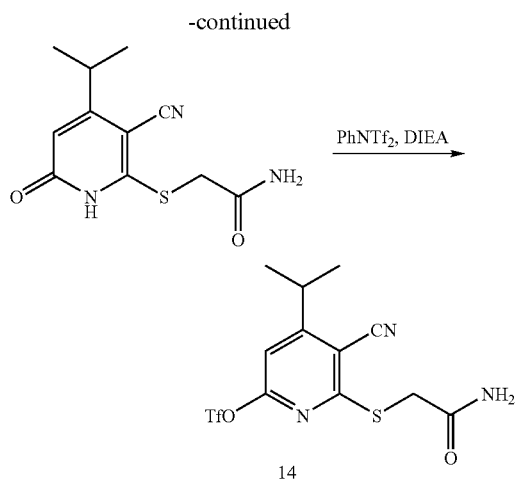

14

To a solution of ethyl isobutyrate (12.0 g, 15.1 mmol) in 15 mL of dry DMF was added 2-cyanothioacetamide (7.76 g, 15.2 mmol) followed by potassium tert-butoxide (9.00 g, 76.2 mmol). This mixture was heated at 80° C. under argon for 4 h, then cooled to room temperature. 2-Bromoacetamide (10.6 g, 75.3 mmol) was added. The resultant suspension was stirred at room temperature for 30 min. Water was added. 2-(3-Cyano-4-isopropyl-6-oxo-1,6-dihydro-pyridin-2-ylsulfanyl)-acetamide was collected by filtration and recrystallized from MeOH (4.62 g, 24%).

2-(3-Cyano-4-isopropyl-6-oxo-1,6-dihydro-pyridin-2-ylsulfanyl)-acetamide (4.62 g, 18.4 mmol) and N-phenyltrifluoromethanesulfonimide (7.00 g, 19.4 mmol) were suspended/dissolved in 100 mL of dichloromethane. Diisopropylethylamine (4.00 mL, 22.7 mmol) was added. This mixture was stirred at room temperature for 4 h. Trifluoro-methanesulfonic acid 6-carbamoylmethylsulfanyl-5-cyano-4-isopropyl-pyridin-2-yl ester was collected by filtration and washed with dichloromethane providing 4.64 g (66%). (ES+ 384 m/z (MH+). The title compound was prepared using a method analogous to that described in Example 13.

Example 15

3-Amino-6-[4-(2-hydroxy-2-pyridin-2-yl-ethylamino)-piperidin-1-yl]-4-isopropyl-thieno[2,3-b]pyridine-2-carboxylic acid amide

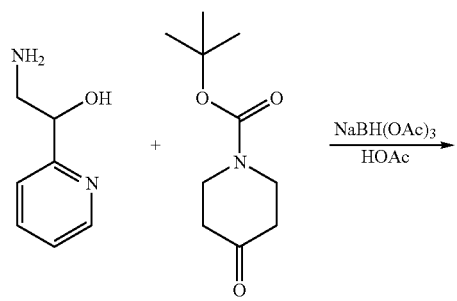

-continued

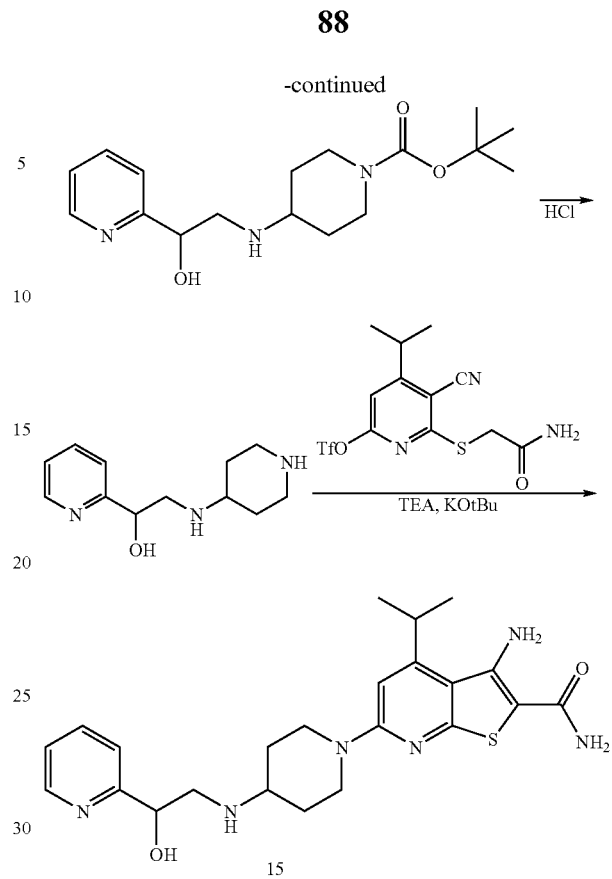

2-Amino-1-pyridin-2-yl-ethanol (0.700 g, 5.07 mmol) and N-boc-piperidone (1.20 g, 5.90 mmol) was dissolved in 5 mL of 1,2-dichloroethane. Glacial acetic acid (0.40 mL, 7.0 mmol) was added followed by sodium tricaetoxyborohydride (2.00 g, 8.97 mmol). This mixture was stirred at room temperature under argon for 16 h. The solvent was removed in vacuo and the residue was purified by flash chromatography (silica gel 12 g, eluted with dichloromethane, MeOH and ammonium hydroxide 100 to 95:4.9: 0.1) to give 4-(2-hydroxy-2-pyridin-2-yl-ethylamino)-piperidine-1-carboxylic acid tert-butyl ester as a brown oil (1.46 g, 90%).

4-(2-Hydroxy-2-pyridin-2-yl-ethylamino)-piperidine-1-carboxylic acid tert-butyl ester (1.46 g, 4.54 mmol) was dissolved in 5 mL of MeOH. HCl in 1,4-dioxane (4.0 M, 5 mL, 20 mmol) was added. This solution was stirred at room temperature for 40 min. The solvent was removed in vacuo. The residue was triturated with ether to give2-(Piperidin-4-ylamino)-1-pyridin-2-yl-ethanol dihydrochloride salt as a brown solid (1.314 g, 88%)

The above solid (265 mg, 0.801 mmol) and trifluoromethanesulfonic acid 6-carbamoylmethylsulfanyl-5-cyano-4-isopropyl-pyridin-2-yl ester (310 mg, 0.809 mmol) was dissolved/suspended in 10 mL of dioxane. Triethylamine (0.56 mL, 4.0 mmol) was added. This reaction mixture was heated at 80° C. for 2 h. Potassium t-butoxide (230 mg, 1.95 mmol) was added. This reaction mixture was heated at 80° C. for an additional 4 h. The solvent was removed in vacuo and the residue was purified by silica gel flash chromatography eluted with 0–5% ammonia/MeOH (0.1% ammonia) in dichloromethane to give the title compound as a crystalline product. Yield: 143 mg, 39%. ES+ 455 m/z (MH+).

3-Amino-4-cyclopropyl-6-[4-(2-hydroxy-2-pyridin-2-yl-ethylamino)-piperidin-1-yl]-thieno[2,3-b]pyridine-2-carboxylic acid amide was prepared via the methods described in example 13 and Scheme II (ES+ 453 m/z (MH+)).

3-Amino-4-ethyl-6-[4-(2-hydroxy-2-pyridin-2-yl-ethylamino)-piperidin-1-yl]-thieno[2,3-b]pyridine-2-carboxylic acid amide was prepared via the methods described in example 14 and Scheme II (ES+ 441 m/z (MH+)).

Example 16

3-Amino-6-[4-(2-hydroxy-2-pyridin-2-yl-ethylamino)-piperidin-1-yl]-4-(2,2,2-trifluoro-ethoxy)-thieno[2,3-b]pyridine-2-carboxylic acid amide

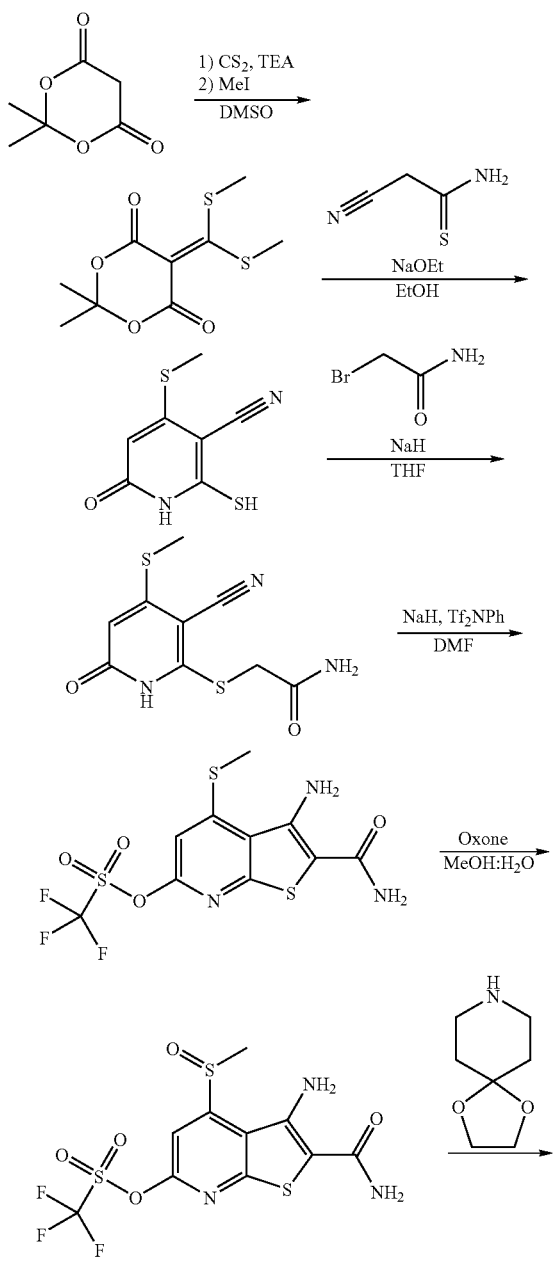

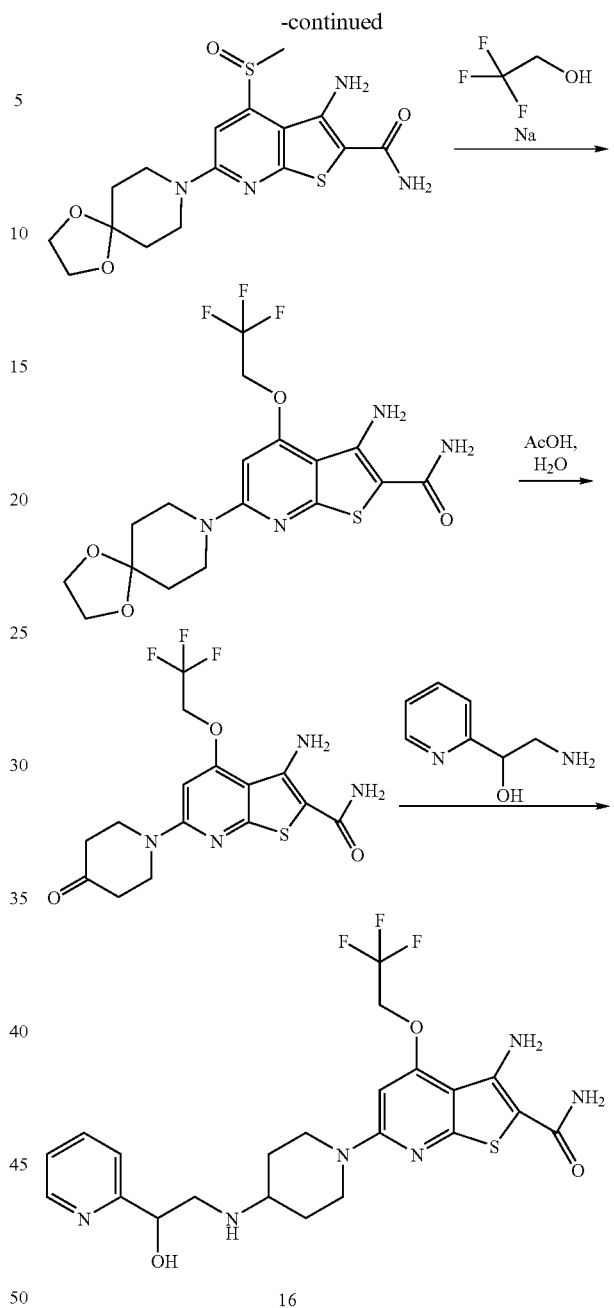

16

To a solution of 2,2-dimethyl-1,3-dioxane-4,6-dione (60.0 g, 416 mmol) in DMSO (150 mL) was added carbon disulfide (25 mL, 420 mmol) and triethylamine (116 mL, 832 mmol). The mixture was stirred at room temperature for 1 h then cooled to 0° C. and 52 mL (830 mmol) of iodomethane was added. The reaction mixture was allowed to slowly warm to room temperature and stirred for 15h. The mixture was decanted into an ice—H2O mixture and a solid was precipitated by agitation of the solution. The solid was collected by filtration, washed with a 1:1 mixture of petroleum ether: Et2O, and dried under vacuum to provide 29.7 g (28.8%) of 5-(bis-methylsulfanyl-methylene)-2,2-dimethyl-[1,3]dioxane-4,6-dione as an orange solid.

To a solution of sodium ethoxide (40.0 mL, 123 mmol) in ETOH (150 mL) was added cyanothioacetamide (12.5 g, 122 mmol). The mixture was stirred at room temperature for 15 min then 30.0 g (121 mmol) of the above dione was added as a solution in EtOH (100 mL). The suspension was heated to reflux for 15 h. The mixture was cooled to room temperature and the solid was collected by filtration. The material was wash with EtOH and dried under reduced pressure to provide 12.5 (52.2%) of 2-mercapto-4-methyl-sulfanyl-6-oxo-1,6-dihydro-pyridine-3-carbonitrile as a yellow solid.

To a solution of the above 2-mercapto-4-methylsulfanyl-6-oxo-1,6-dihydro-pyridine-3-carbonitrile (12.5 g, 63.0 mmol) in DMF (300 mL), cooled to 0° C., was added sodium hydride (2.60 g, 65.0 mmol) as a 60% dispersion in mineral oil. The mixture was stirred at 0° C. for 30 min then 2-bromoacetamide (8.80 g, 63.8 mmol) was added as a solid in one portion. The mixture was allowed to slowly warm to room temperature and stirred for 15 h. The mixture poured into ice—H$_2$O and stirred until all of the ice had melted, during which time a solid precipitated from solution. The mixture was acidified with 2N HCl then cooled to 0° C. and the solid collected by filtration. The material was washed with Et$_2$O followed by hexanes to provide 11.2 g (69.9%) of 2-(3-cyano-4-methylsulfanyl-6-oxo-1,6-dihydro-pyridin-2-ylsulfanyl)-acetamide as a tan solid.

To a solution of 2-(3-cyano-4-methylsulfanyl-6-oxo-1,6-dihydro-pyridin-2-ylsulfanyl)-acetamide (11.2 g, 44.1 mmol) in DMF (300 mL), cooled to 0° C., was added sodium hydride (3.60 g, 90.0 mmol) as a 60% dispersion in mineral oil. The mixture was stirred at 0° C. for 30 min and N-phenyltrifluoromethanesulfonimide was then (15.8 g, 44.2 mmol) added as a solution in DMF (100 mL). The mixture was allowed to slowly warm to room temperature and stirred for 15h. The mixture was poured into H$_2$O which caused a solid to precipitate from solution. The solid was collected by filtration, washed with H$_2$O and dried under reduced pressure to provide 8.95 (52.4%) of trifluoro-methanesulfonic acid 3-amino-2-carbamoyl-4-methylsulfanyl-thieno[2,3-b]pyridin-6-yl ester as a yellow powder.

To a suspension of the above trifluoro-methanesulfonic acid 3-amino-2-carbamoyl-4-methylsulfanyl-thieno[2,3-b]pyridin-6-yl ester (8.95 g, 23.1 mmol) in a 1:1 mixture of H$_2$O and MeOH (200 mL), cooled to 0° C., was added oxzone (17.0 g, 27.7 mmol) as a solid in one portion. The reaction mixture was allowed to slowly warm to room temperature and stirred for 6h. LCMS indicated the presence of the desired product with a trace that exhibited a peak at mass 404.08 [M+H]$^+$. The yellow solid was collected by filtration and washed with H$_2$O. The residue was purified by washing with EtOAc and drying under reduced pressure to provide 3.00 g (32.2%) of trifluoro-methanesulfonic acid 3-amino-2-carbamoyl-4-methanesulfinyl-thieno[2,3-b]pyridin-6-yl ester as a yellow powder.

To a solution of trifluoro-methanesulfonic acid 3-amino-2-carbamoyl-4-methanesulfinyl-thieno[2,3-b]pyridin-6-yl ester (3.00 g, 7.44 mmol) in DMF (100 mL) was added 1,4-dioxa-8-azaspiro[4,5]-decane (2.20 g, 15.4 mmol). The mixture was heated to 70° C. for 1 h. The mixture was cooled to room temperature, diluted with H$_2$O, and washed with CH$_2$Cl$_2$. The combined organic phase was dried over anhydrous Na$_2$SO$_4$ and concentrated under reduced pressure. The residue was purified by flash silica gel chromatography to provide 1.25 g (42.2%) of 3-amino-6-(1,4-dioxa-8-aza-spiro[4.5]dec-8-yl)-4-methanesulfinyl-thieno[2,3-b]pyridine-2-carboxylic acid amide as a yellow solid.

To 30 mL of 2,2,2-trifluoroethanol cooled to 0° C. was added sodium metal (0.60 g, 15 mmol), cut fresh and washed in hexanes, in small portions. The mixture was allowed to warm up to room temperature and let stir until all of the sodium metal had reacted. To the mixture was added 3-amino-6-(1,4-dioxa-8-aza-spiro[4.5]dec-8-yl)-4-methane-sulfinyl-thieno[2,3-b]pyridine-2-carboxylic acid amide (1.30 g, 3.28 mmol) as a solid in one portion. The mixture was heated to 70° C. for 15 h. The mixture was cooled to room temperature and diluted with H$_2$O. The mixture was washed with CH$_2$Cl$_2$ and the combined organic phase was dried over anhydrous Na$_2$SO$_4$ and concentrated under reduced pressure. The residue was purified by flash silica gel chromatography to provide 0.940 g of 3-amino-6-(1,4-dioxa-8-aza-spiro[4.5]dec-8-yl)-4-(2,2,2-trifluoro-ethoxy)-thieno[2,3-b]pyridine-2-carboxylic acid amide as a white powder.

A solution of 3-amino-6-(1,4-dioxa-8-aza-spiro[4.5]dec-8-yl)-4-(2,2,2-trifluoro-ethoxy)-thieno[2,3-b]pyridine-2-carboxylic acid amide as a white powder (0.940 g, 2.17 mmol) in a 4:1 mixture of acetic acid: H$_2$O (20 mL) was heated to 80° C. for 4h then cooled to room temperature and made basic by the addition of a saturated aqueous solution of NaHCO$_3$ which caused a solid to precipitate from solution. The solid was collected by filtration and dried under reduced pressure to provide 0.680 g (80.5%) of 3-amino-6-(4-oxo-piperidin-1-yl)-4-(2,2,2-trifluoro-ethoxy)-thieno[2,3-b]pyridine-2-carboxylic acid amide as a clear oil.

The title compound was prepared from ther above intermediate using a procedure analogous to that described in Example 1. ES$^+$ 511.22 m/z (MH$^+$)

Example 17

3-Amino-6-{4-[2-hydroxy-3-(pyridin-4-yloxy)-propylamino]-piperidin-1-yl}-4-propyl-thieno[2,3-b]pyridine-2-carboxylic acid amide

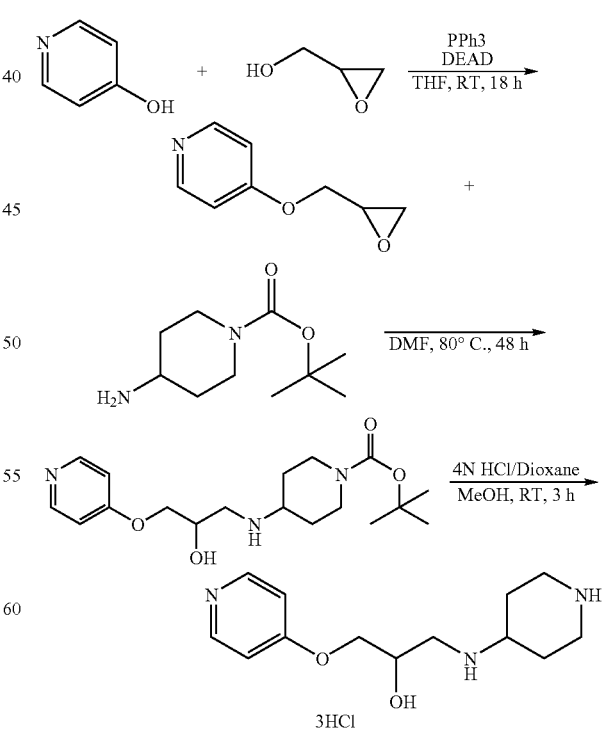

17

To a round bottom flask was added 4-hydroxypyridine (250 mg, 2.63 mmol), glycidol (194.74 mg, 2.63 mmol) and triphenylphosphine (758.45 mg, 2.89 mmol) in 20 mL of dry THF, followed by the addition of diethyl azodicarboxylate (503.6 mg, 2.89 mmol). The reaction mixture was stirred at room temperature for 18 h. The reaction mixture was concentrated in vacuo. The residue was diluted with $CH_2Cl_2$. The organic phase was washed with saturated $NaHCO_3$ and brine. The organic phase was dried over anhydrous $Na_2SO_4$, filtered and concentrated. The residue was loaded to a flash chromatography column. The column was eluted with 0–5% $MeOH/CH_2Cl_2$. The product fractions were collected and concentrated to afford 80 mg (20.1%) of 4-oxiranylmethoxy-pyridine. (TLC: Rf=0.4, 5% $MeOH/CH_2Cl_2$, UV). $MH^+$=152.31.

To a sealed tube was added 4-oxiranylmethoxy-pyridine (80 mg, 0.529 mmol) in 4 mL of DMF, followed by the addition of 4-amino-1-N-boc-piperidine (148 mg, 0.739 mmol). The reaction mixture was stirred at 80° C. for 48 h. The reaction mixture was concentrated in vacuo. The residue was loaded to a flash chromatography column. The column was eluted with 0–5% 2M $NH_3$ in $MeOH/CH_2Cl_2$. The product fractions were collected and concentrated to afford 68 mg (36.6%) of 4-[2-hydroxy-3-(pyridin-4-yloxy)-propylamino]-piperidine-1-carboxylic acid tert-butyl ester as a light brown oil. (TLC: Rf=0.15, 5% 2M $NH_3$ in $MeOH/CH_2Cl_2$, UV). $ES^+$ 352.43 m/z ($MH^+$)

To a round bottom flask was added 4-[2-hydroxy-3-(pyridin-4-yloxy)-propylamino]-piperidine-1-carboxylic acid tert-butyl ester (68 mg, 0.194 mmol) in 5 mL of HCl (4.0 M in 1,4-dioxane) and 5 mL of MeOH. The reaction mixture was stirred at room temperature for 3 h. The reaction mixture was concentrated by high vacuum pump to afford 69 mg (98.9%) of off-white solid product 1-(piperidin-4-ylamino)-3-(pyridin-4-yloxy)-propan-2-ol 3 HCl salt. $ES^+$ 252.41 m/z ($MH^+$)

To a sealed tube was added trifluoro-methanesulfonic acid 6-carbamoylmethylsulfanyl-5-cyano-4-propyl-pyridin-2-yl ester (66.7 mg, 0.174 mmol) in 4 mL of dry DMF, followed by the addition of 1-(piperidin-4-ylamino)-3-(pyridin-4-yloxy)-propan-2-ol trihydrochloride salt (69 mg, 0.191 mmol) and N-N-diisopropylethylamine (180 mg, 1.39 mmol). The reaction mixture was stirred at 70° C. for 2 h. DMF was removed in vacuo. The residue was dissolved in 5 mL of MeOH, followed by the addition of sodium methoxide, 0.5 M solution in MeOH (1.74 mL, 0.86 mmol). The reaction mixture was stirred at 70° C. for 2 h. The reaction mixture was concentrated in vacuo. The residue was loaded onto a flash chromatography column. The column was eluted with 0–5% 2M $NH_3$ in $MeOH/CH_2Cl_2$. The product fractions were collected, concentrated and dried under high vacuum pump to afford 24 mg (28.5%) of the title compound as a light brown solid product. (TLC: Rf=0.4, 5% 2M $NH_3$ in $MeOH/CH_2Cl_2$, UV). $ES^+$ 485.29 m/z ($MH^+$)

3-Amino-6-{4-[2-hydroxy-3-(quinolin-4-yloxy)-propylamino]-piperidin-1-yl}-4-propyl-thieno[2,3-b]pyridine-2-carboxylic acid amide was prepared via the methods described in example 17 and Scheme II. $ES^+$ 535.44 m/z ($MH^+$)

3-Amino-6-{4-[2-hydroxy-3-(isoquinolin-5-yloxy)-propylamino]-piperidin-1-yl}-4-propyl-thieno[2,3-b]pyridine-2-carboxylic acid amide was prepared via the methods described in example 17 and Scheme II. $ES^+$ 535.45 m/z ($MH^+$)

3-Amino-6-{4-[2-hydroxy-3-(quinolin-5-yloxy)-propylamino]-piperidin-1-yl}-4-propyl-thieno[2,3-b]pyridine-2-carboxylic acid amide was prepared via the methods described in example 17 and Scheme II. $ES^+$ 535.30 m/z ($MH^+$)

3-Amino-6-{4-[2-hydroxy-3-(quinolin-6-yloxy)-propylamino]-piperidin-1-yl}-4-propyl-thieno[2,3-b]pyridine-2-carboxylic acid amide was prepared via the methods described in example 17 and Scheme II. $ES^+$ 535.33 m/z ($MH^+$)

3-Amino-6-{4-[(S)-2-hydroxy-3-(quinolin-6-yloxy)-propylamino]-piperidin-1-yl}-4-trifluoromethyl-thieno[2,3-b]pyridine-2-carboxylic acid amide was prepared via the methods described in example 17 and Scheme II. $ES^+$ 561.31 m/z ($MH^+$)

3-Amino-6-{4-[(R)-2-hydroxy-3-(quinolin-6-yloxy)-propylamino]-piperidin-1-yl}-4-trifluoromethyl-thieno[2,3-b]pyridine-2-carboxylic acid amide was prepared via the methods described in example 17 and Scheme II. $ES^+$ 561.31 m/z ($MH^+$)

3-Amino-6-[4-(2-hydroxy-2-pyrimidin-5-yl-ethylamino)-piperidin-1-yl]-4-trifluoromethyl-thieno[2,3-b]pyridine-2-carboxylic acid amide $ES^+$ 482.30 m/z ($MH^+$) was prepared via the methods described in example 8 and scheme II.

3-Amino-6-{4-[2-(6-bromo-pyridin-2-yl)-2-hydroxyethylamino]-piperidin-1-yl}-4-trifluoromethyl-thieno[2,3-b]pyridine-2-carboxylic acid amide m/z ($MH^+$) was prepared via the methods described in example 8 and scheme II. $ES^+$ 559.08/562.07

3-Amino-6-{4-[2-hydroxy-2-(6-hydroxy-pyridin-2-yl)-ethylamino]-piperidin-1-yl}-4-trifluoromethyl-thieno[2,3-b]pyridine-2-carboxylic acid amide was prepared from 6-tert-Butoxy-pyridine-2-carbaldehyde via the methods described in example 8 and scheme II. $ES^+$ 497.58 m/z ($MH^+$)

3-Amino-6-{4-[2-hydroxy-2-(6-hydroxy-pyridin-2-yl)-ethylamino]-piperidin-1-yl}-4-propyl-thieno[2,3-b]pyridine-2-carboxylic acid amide was prepared from 6-tert-Butoxy-pyridine-2-carbaldehyde via the methods described in example 8 and scheme II. $ES^+$ 471.35 m/z ($MH^+$)

3-Amino-6-{4-[2-(6-chloro-pyridin-3-yl)-2-hydroxyethylamino]-piperidin-1-yl}-4-trifluoromethyl-thieno[2,3-b]pyridine-2-carboxylic acid amide was prepared via the methods described in example 8 and scheme II. $ES^+$ 515.49/517.49 m/z ($MH^+$)

3-Amino-6-{4-[2-hydroxy-2-(6-methoxy-pyridin-3-yl)-ethylamino]-piperidin-1-yl}-4-trifluoromethyl-thieno[2,3-b]pyridine-2-carboxylic acid amide was prepared via the methods described in example 8 and scheme II. $ES^+$ 511.45 m/z ($MH^+$)

3-Amino-6-{4-[2-hydroxy-2-(1-methyl-1H-imidazol-2-yl)-ethylamino]-piperidin-1-yl}-4-trifluoromethyl-thieno[2,3-b]pyridine-2-carboxylic acid amide was prepared via the methods described in example 1 and scheme II. $ES^+$ 484.23 m/z ($MH^+$)

3-Amino-6-{4-[2-hydroxy-2-(2-methyl-3H-imidazol-4-yl)-ethylamino]-piperidin-1-yl}-4-trifluoromethyl-thieno[2,3-b]pyridine-2-carboxylic acid amide was prepared via the methods described in example 12 and scheme II. $ES^+$ 484.13 m/z ($MH^+$)

3-Amino-6-{4-[2-hydroxy-2-(2-hydroxy-pyridin-4-yl)-ethylamino]-piperidin-1-yl}-4-trifluoromethyl-thieno[2,3-b]pyridine-2-carboxylic acid amide was prepared from 2-Hydroxy-pyridine-4-carbaldehyde via the methods described in example 12 and scheme II. $ES^+$ 497.37 m/z ($MH^+$)

2-Hydroxy-pyridine-4-carbaldehyde was available from 4-Methyl-pyridin-2-ol as described in *J. Am. Chem Soc.* 1997 115, 3619.

Example 18

3-Amino-6-[4-(2-[3,3']bipyridinyl-6-yl-2-hydroxy-ethylamino)-piperidin-1-yl]-4-trifluoromethyl-thieno[2,3-b]pyridine-2-carboxylic acid amide

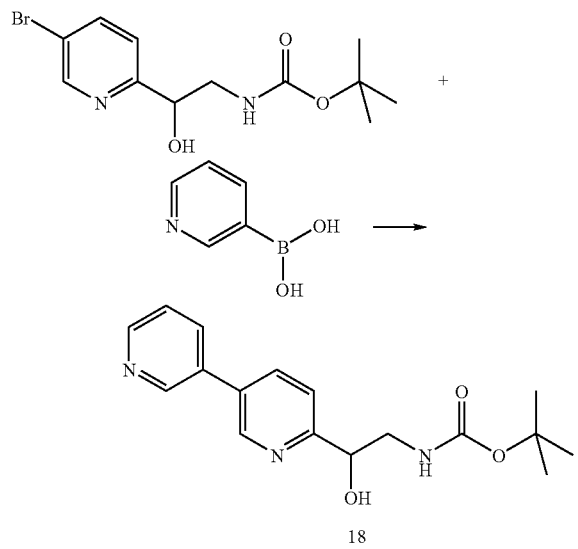

18

An N$_2$-purged suspension of [2-(5-Bromo-pyridin-2-yl)-2-hydroxy-ethyl]-carbamic acid tert-butyl ester (460 mg, 1.45 mmol), tetrakis(triphenylphosphine)-palladium(0) (168 mg, 0.145 mmol), potassium carbonate (401 mg, 2.90 mmol), and pyridine-3-boronic acid (207 mg, 1.60 mmol) in dry DMF (15 ml) and water (3 ml) was sealed and heated to 85° C. for 18h. The reaction was quenched with 100 ml water and extracted with 3×150 ml ethyl acetate. The combined organic phases were dried with Na$_2$SO$_4$, filtered and concentrated in vacuo. The residue was dissolved in a small amount of DMF, applied to a celite plug, and purified by SiO$_2$ chromatography (0–100% EtOAc/CH$_2$Cl$_2$, then 0–25% MeOH/EtOAc) to give 442 mg, 87.0%, of (2-[3,3']Bipyridinyl-6-yl-2-hydroxy-ethyl)-carbamic acid tert-butyl ester ES$^+$ 316.5 m/z (MH$^+$).

3-Amino-6-[4-(2-[3,3']bipyridinyl-6-yl-2-hydroxy-ethylamino)-piperidin-1-yl]-4-trifluoromethyl-thieno[2,3-b]pyridine-2-carboxylic acid amide was prepared via the methods described in scheme II.

3-Amino-6-{4-[2-hydroxy-2-(5-quinolin-3-yl-pyridin-2-yl)-ethylamino]-piperidin-1-yl}-4-trifluoromethyl-thieno[2,3-b]pyridine-2-carboxylic acid amide was prepared via the methods described in example 18 and Scheme II. ES$^+$ 608.6 m/z (MH$^+$)

3-Amino-6-{4-[2-hydroxy-2-(5-phenyl-pyridin-2-yl)-ethylamino]-piperidin-1-yl}-4-trifluoromethyl-thieno[2,3-b]pyridine-2-carboxylic acid amide was prepared via the methods described in example 18 and Scheme II. ES$^+$ 557.7 m/z (MH$^+$)

3-Amino-6-{4-[2-(6'-dimethylamino-[3,3']bipyridinyl-6-yl)-2-hydroxy-ethylamino]-piperidin-1-yl}-4-trifluoromethyl-thieno[2,3-b]pyridine-2-carboxylic acid amide was prepared via the methods described in example 18 and Scheme II. ES$^+$ 601.9 m/z (MH$^+$)

3-Amino-6-{4-[2-hydroxy-2-(5-pyrimidin-5-yl-pyridin-2-yl)-ethylamino]-piperidin-1-yl}-4-trifluoromethyl-thieno[2,3-b]pyridine-2-carboxylic acid amide was prepared via the methods described in example 18 and Scheme II. ES$^+$ 559.9 m/z (MH$^+$)

3-Amino-6-[4-(2-[3,4']bipyridinyl-6-yl-2-hydroxy-ethylamino)-piperidin-1-yl]-4-trifluoromethyl-thieno[2,3-b]pyridine-2-carboxylic acid amide was prepared via the methods described in example 18 and Scheme II. ES$^+$ 558.9 m/z (MH$^+$)

3-Amino-6-{4-[2-hydroxy-2-(5-quinolin-8-yl-pyridin-2-yl)-ethylamino]-piperidin-1-yl}-4-trifluoromethyl-thieno[2,3-b]pyridine-2-carboxylic acid amide was prepared via the methods described in example 18 and Scheme II. ES$^+$ 608.9 m/z (MH$^+$)

3-Amino-6-{4-[2-hydroxy-2-(5-isoquinolin-4-yl-pyridin-2-yl)-ethylamino]-piperidin-1-yl}-4-trifluoromethyl-thieno[2,3-b]pyridine-2-carboxylic acid amide was prepared via the methods described in example 18 and Scheme II. ES$^+$ 608.8 m/z (MH$^+$)

3-Amino-6-{4-[2-(5-bromo-pyridin-2-yl)-2-hydroxy-ethylamino]-piperidin-1-yl}-4-trifluoromethyl-thieno[2,3-b]pyridine-2-carboxylic acid amide was prepared via the methods described in example 1 and scheme II. ES$^+$ 559.6/561.6 m/z (MH$^+$)

Example 19

3-Amino-6-(4-{2-hydroxy-2-[5-(3-methanesulfonyl-phenyl)-pyridin-2-yl]-ethylamino}-piperidin-1-yl)-4-trifluoromethyl-thieno[2,3-b]pyridine-2-carboxylic acid amide

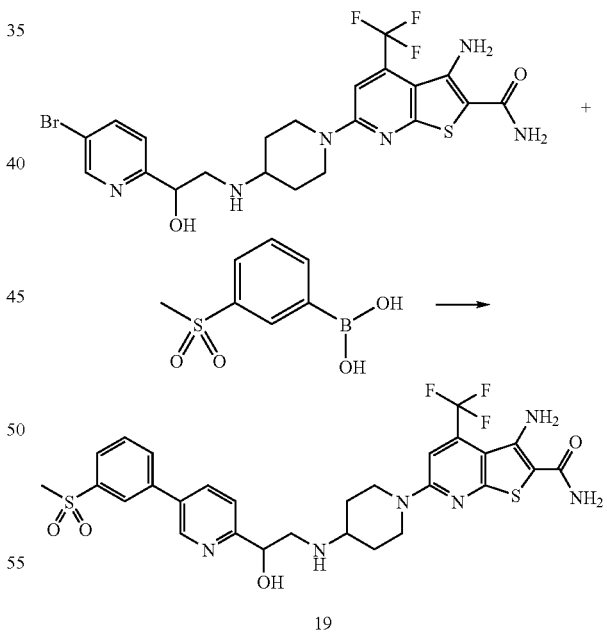

19

A N$_2$-purged suspension of 3-Amino-6-{4-[2-(5-bromo-pyridin-2-yl)-2-hydroxy-ethylamino]-piperidin-1-yl}-4-trifluoromethyl-thieno[2,3-b]pyridine-2-carboxylic acid amide (60 mg, 0.107 mmol), (3-methylsulfonylphenyl)boronic acid (24 mg, 0.118 mmol), tetrakis(triphenylphosphine)palladium(0) (19 mg, 0.016 mmol), and potassium carbonate (30 mg, 0.214 mmol) in dry DMF (4 ml) and water (1 ml) was sealed and heated to 85° C. for 18h. The crude reaction mixture was applied to a celite plug and purified by SiO₂ chromatography (0–25% MeOH/CH₂Cl₂ with 1% NH₄OH). Fractions containing product were pooled and concentrated. The solid yellow residue was dissolved in 1 ml DMF, applied to a 2 mm prep plate (Merck) and eluted twice with 10% MeOH/CH₂Cl₂ with 1% NH₄OH. The recovered yellow residue was dissolved in 0.5 ml water, 2 ml MeOH, 10 ml CH₂Cl₂, and 10 ml EtOAc and crystallized by the addition of 50 ml hexanes to give 29.0 mg, 42.3% of 3-Amino-6-(4-{2-hydroxy-2-[5-(3-methanesulfonyl-phenyl)-pyridin-2-yl]-ethylamino}-piperidin-1-yl)-4-trifluoromethyl-thieno[2,3-b]pyridine-2-carboxylic acid amide product. ES⁺ 635.1 m/z (MH⁺).

3-Amino-6-(4-{2-hydroxy-2-[5-(3-hydroxy-phenyl)-pyridin-2-yl]-ethylamino}-piperidin-1-yl)-4-trifluoromethyl-thieno[2,3-b]pyridine-2-carboxylic acid amide was prepared via the methods described in example 19 and Scheme II. ES⁺ 573.1 m/z (MH⁺)

3-Amino-6-(4-{2-hydroxy-2-[5-(3-methanesulfonylamino-phenyl)-pyridin-2-yl]-ethylamino}-piperidin-1-yl)-4-trifluoromethyl-thieno[2,3-b]pyridine-2-carboxylic acid amide was prepared via the methods described in example 19 and Scheme II. ES⁺ 650.2 m/z (MH⁺)

3-Amino-6-(4-{2-hydroxy-2-[5-(3-hydroxymethyl-phenyl)-pyridin-2-yl]-ethylamino}-piperidin-1-yl)-4-trifluoromethyl-thieno[2,3-b]pyridine-2-carboxylic acid amide was prepared via the methods described in example 19 and Scheme II. ES⁺ 587.3 m/z (MH⁺)

3-Amino-6-(4-{2-[5-(3-amino-phenyl)-pyridin-2-yl]-2-hydroxy-ethylamino}-piperidin-1-yl)-4-trifluoromethyl-thieno[2,3-b]pyridine-2-carboxylic acid amide was prepared via the methods described in example 19 and Scheme II. ES⁺ 572.4 m/z (MH⁺)

3-Amino-6-(4-{2-[5-(3-dimethylamino-phenyl)-pyridin-2-yl]-2-hydroxy-ethylamino}-piperidin-1-yl)-4-trifluoromethyl-thieno[2,3-b]pyridine-2-carboxylic acid amide was prepared via the methods described in example 19 and Scheme II. ES⁺ 600.2 m/z (MH⁺)

3-Amino-6-(4-{2-hydroxy-2-[5-(3-methylcarbamoyl-phenyl)-pyridin-2-yl]-ethylamino}-piperidin-1-yl)-4-trifluoromethyl-thieno[2,3-b]pyridine-2-carboxylic acid amide was prepared via the methods described in example 19 and Scheme II. ES⁺ 614.3 m/z (MH⁺)

3-Amino-6-(4-{2-[5-(3-dimethylcarbamoyl-phenyl)-pyridin-2-yl]-2-hydroxy-ethylamino}-piperidin-1-yl)-4-trifluoromethyl-thieno[2,3-b]pyridine-2-carboxylic acid amide was prepared via the methods described in example 19 and Scheme II. ES⁺ 628.3 m/z (MH⁺)

6-(4-{2-[5-(3-Acetylamino-phenyl)-pyridin-2-yl]-2-hydroxy-ethylamino}-piperidin-1-yl)-3-amino-4-trifluoromethyl-thieno[2,3-b]pyridine-2-carboxylic acid amide was prepared via the methods described in example 19 and Scheme II. ES⁺ 614.3 m/z (MH⁺)

3-Amino-6-{4-[2-(6'-amino-[3,3']bipyridinyl-6-yl)-2-hydroxy-ethylamino]-piperidin-1-yl}-4-trifluoromethyl-thieno[2,3-b]pyridine-2-carboxylic acid amide was prepared via the methods described in example 19 and Scheme II. ES⁺ 573.3 m/z (MH⁺)

3-Amino-6-(4-{2-[5-(3-carbamoyl-phenyl)-pyridin-2-yl]-2-hydroxy-ethylamino}-piperidin-1-yl)-4-trifluoromethyl-thieno[2,3-b]pyridine-2-carboxylic acid amide was prepared via the methods described in example 19 and Scheme II. ES⁺ 600.3 m/z (MH⁺)

3-Amino-6-[4-(2-hydroxy-2-{5-[3-(morpholine-4-carbonyl)-phenyl]-pyridin-2-yl}-ethylamino)-piperidin-1-yl]-4-trifluoromethyl-thieno[2,3-b]pyridine-2-carboxylic acid amide was prepared via the methods described in example 19 and Scheme II. ES⁺ 670.4 m/z (MH⁺)

3-Amino-6-(4-{2-hydroxy-2-[5-(2-methoxy-pyrimidin-5-yl)-pyridin-2-yl]-ethylamino}-piperidin-1-yl)-4-trifluoromethyl-thieno[2,3-b]pyridine-2-carboxylic acid amide was prepared via the methods described in example 19 and Scheme II. ES⁺ 589.3 m/z (MH⁺)

3-Amino-6-{4-[2-hydroxy-2-(6'-methoxy-[3,3']bipyridinyl-6-yl)-ethylamino]-piperidin-1-yl}-4-trifluoromethyl-thieno[2,3-b]pyridine-2-carboxylic acid amide was prepared via the methods described in example 19 and Scheme II. ES⁺ 588.4 m/z (MH⁺)

Example 20

3-Amino-6-(4-{2-hydroxy-2-[5-(2-oxo-2,3-dihydro-1H-indol-6-yl)-pyridin-2-yl]-ethylamino}-piperidin-1-yl)-4-trifluoromethyl-thieno[2,3-b]pyridine-2-carboxylic acid amide

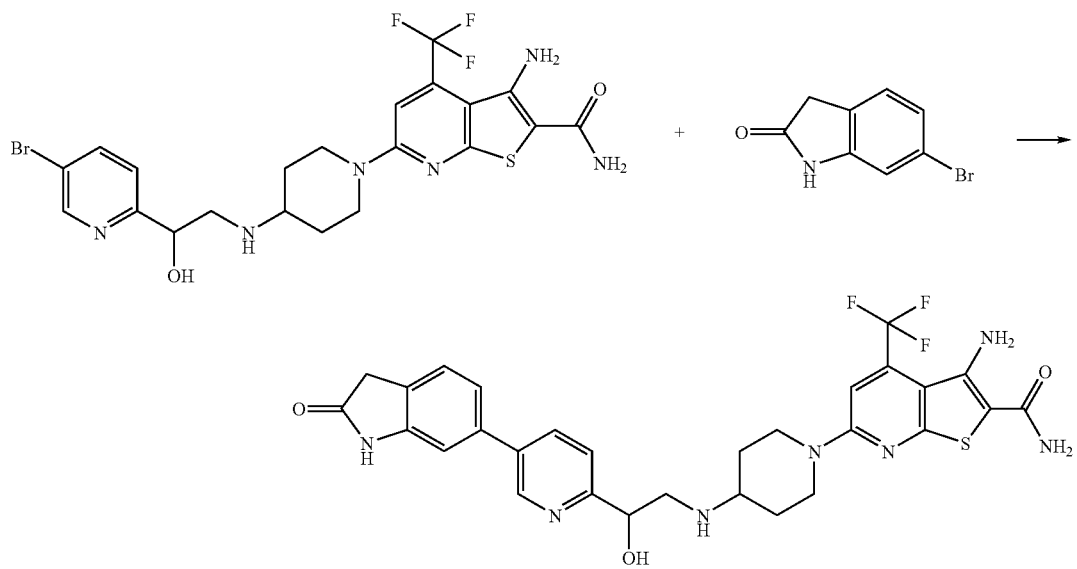

An N$_2$-purged suspension of 3-Amino-6-{4-[2-(5-bromo-pyridin-2-yl)-2-hydroxy-ethylamino]-piperidin-1-yl}-4-trifluoromethyl-thieno[2,3-b]pyridine-2-carboxylic acid amide (150 mg, 0.268 mmol), bis(pinacolato)diboron (153 mg, 0.590 mmol), [1,1'-bis(diphenylphosphino)ferrocene]dichloropalladium(II)-CH$_2$Cl$_2$ complex (33 mg, 0.040 mmol), and potassium acetate (133 mg, 1.34 mmol) in dry DMF (4 ml) was heated at 80° C. for 2.5 h. The crude reaction mixture was then added directly via syringe to a stirring, N$_2$-purged suspension of 6-bromo-2-oxindole (65 mg, 0.295 mmol), tetrakis(triphenylphosphine)palladium(0) (47 mg, 0.040 mmol), and potassium carbonate (74 mg, 0.536 mmol) in dry DMF (6 ml) and water (2 ml) at rt. The sealed mixture was heated to 85° C. for 4 h. The crude reaction was applied direcly to a SiO$_2$ column and purified (0–25% MeOH/CH$_2$Cl$_2$ with NH$_4$OH). Fractions containing desired product were pooled and concentrated. The yellow residue was dissolved in 2 ml DMF and applied to a 2 mm prep plate (Merck) eluting with 10% MeOH/CH$_2$Cl$_2$ with 1% NH$_4$OH. The yellow product crystallized at the origin and the impurities were removed by being carried up the plate. The recovered yellow residue was dissolved in 1 ml DMF, 2 ml MeOH, 5 ml EtOAc, and 5 ml CH$_2$Cl$_2$ and crystallized by the addition of 30 ml hexanes to give 20.5 mg, 11.9% of 3-Amino-6-(4-{2-hydroxy-2-[5-(2-oxo-2,3-dihydro-1H-indol-6-yl)-pyridin-2-yl]-ethylamino}-piperidin-1-yl)-4-trifluoromethyl-thieno[2,3-b]pyridine-2-carboxylic acid amide product. ES$^+$ 612.4 m/z (MH$^+$).

3-Amino-6-(4-{2-hydroxy-2-[5-(2-oxo-2,3-dihydro-1H-indol-5-yl)-pyridin-2-yl]-ethylamino}-piperidin-1-yl)-4-trifluoromethyl-thieno[2,3-b]pyridine-2-carboxylic acid amide was prepared via the methods described in example 20 and Scheme II. ES$^+$ 612.5 m/z (MH$^+$)

3-Amino-6-{4-[2-hydroxy-2-(5-thiazol-2-yl-pyridin-2-yl)-ethylamino]-piperidin-1-yl}-4-trifluoromethyl-thieno[2,3-b]pyridine-2-carboxylic acid amide was prepared via the methods described in example 20 and Scheme II. ES$^+$ 564.4 m/z (MH$^+$)

3-Amino-6-[4-(2-hydroxy-2-quinolin-8-yl-ethylamino)-piperidin-1-yl]4-propyl-thieno[2,3-b]pyridine-2-carboxylic acid amide was prepared via the methods described in example 8 and Scheme II. ES$^+$ 505.60 m/z (MH$^+$)

3-Amino-6-[4-(2-hydroxy-2-quinolin-8-yl-ethylamino)-piperidin-1-yl]-4-trifluoromethyl-thieno[2,3-b]pyridine-2-carboxylic acid amide was prepared via the methods described in example 8 and Scheme II. ES$^+$ 531.64 m/z (MH$^+$)

Example 21

3-Amino-6-{4-[2-hydroxy-2-(2-phenyl-1H-benzoimidazol-5-yl)-ethylamino]-piperidin-1-yl}-4-propyl-thieno[2,3-b]pyridine-2-carboxylic acid amide

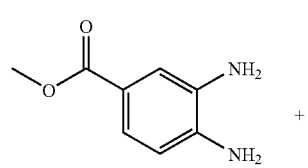

+

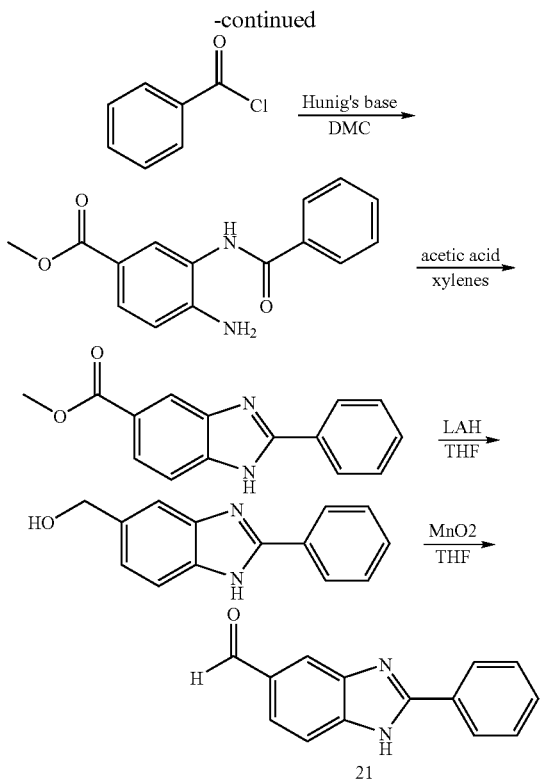

3,4-Diamino-benzoic acid methyl ester (2 g, 12.035 mmol) was dispersed in 40 mL DCM. Added hunig's base (2.516 mL, 14.442 mmol) and stirred at RT until everything was in solution. Added benzoyl chloride (1.397 mL, 12.035 mmol) dropwise into the mixture and stirred at RT for 1 hour. Added sat. NaHCO3 aq. solution into the reaction mixture. Extracted with DCM three times. Combined all organic extracts and washed with brine. Dried over Na2SO4. Filtered and removed solvent in vacuo. Purified by flash chromatography using 10% MeOH/DCM as eluent mixtures. 4-Amino-3-benzoylamino-benzoic acid methyl ester was triturated in hot ethyl acetate and 1.667 g (51.2%) white solid was obtained.

Cylization to benzimidazole was using the procedure found in *Tetrahedron* 2001, 57 (9), 1793–1799

2-Phenyl-1H-benzoimidazole-5-carboxylic acid methyl ester (1.178 g, 4.67 mmol) was dissolved in 20 mL THF. Cooled to 0° C. and then added LAH (886 mg, 23.35 mmol). The mixture was heated to 50° C. overnight. Added 0.9 mL water, 0.9 mL 15% NaOH aqu. solution then 3 mL water. Stirred at RT for 30 mins. Filtered through celite and washed the celite with ethyl acetate. Washed the filtrate with brine. Dried over Na2SO4. Filtered and removed solvent in vacuo. Obtained 783 mg (74.8%) of (2-Phenyl-1H-benzoimidazol-5-yl)-methanol as an off white foam.

(2-Phenyl-1H-benzoimidazol-5-yl)-methanol (783 mg, 3.49 mmol) was dissolved in 20 mL THF. Added MnO2 (3.035 g, 34.91 mmol) and stirred at RT for 1 hour. Filtered through celite and removed solvent in vacuo. Obtained 769 mg (99.1%) of 2-Phenyl-1H-benzoimidazole-5-carbaldehyde as a light yellow foam.

3-Amino-6-{4-[2-hydroxy-2-(2-phenyl-1H-benzoimidazol-5-yl)-ethylamino]-piperidin-1-yl}-4-propyl-thieno[2,3- b]pyridine-2-carboxylic acid amide was was prepared via the methods described in example 2 and Scheme II. ES+ 570.57 m/z (MH+)

3-Amino-6-{4-[2-hydroxy-2-(2-phenyl-1H-benzoimidazol-5-yl)-ethylamino]-piperidin-1-yl}-4-trifluoromethyl-thieno[2,3-b]pyridine-2-carboxylic acid amide was prepared via the methods described in example 21, example 2 and Scheme II. ES+ 596.54 m/z (MH+)

3-Amino-6-{4-[2-hydroxy-2-(2-isopropyl-1H-benzoimidazol-5-yl)-ethylamino]-piperidin-1-yl}-4-trifluoromethyl-thieno[2,3-b]pyridine-2-carboxylic acid amide was prepared via the methods described in example 21, example 2 and Scheme II. ES+ 562.54 m/z (MH+)

Example 22

3-Amino-6-[4-((R)-2-hydroxy-2-pyridin-2-yl-ethylamino)-piperidin-1-yl]-4-trifluoromethyl-thieno[2,3-b]pyridine-2-carboxylic acid amide The enantioselective synthesis of 2-chloro-6-(R)-oxiranyl-pyridine was accomplished in 89% ee using (+)-DIP Chloride according to the method described by Merck and Co., U.S. Pat. No. 5,561,142, Oct. 1, 1996, starting from 6-hydroxypicolinic acid.

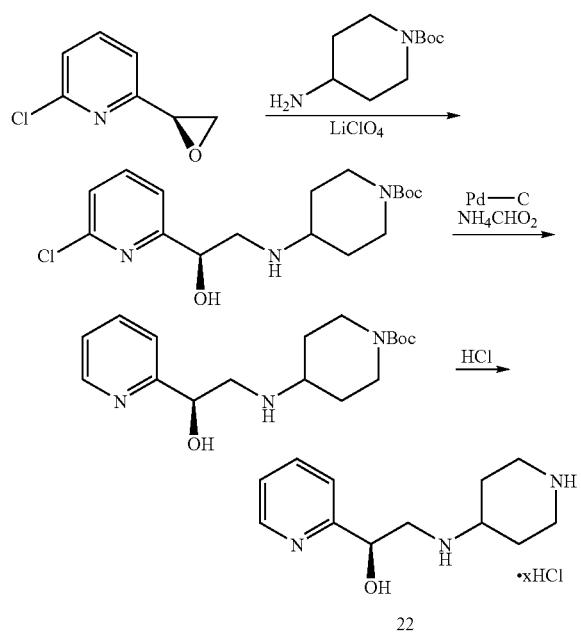

The 2-Chloro-6-(S)-oxiranyl-pyridine was opened with tert-butyl-4-amino-1-piperidine-carboxylate in the presence of lithium perchlorate (see Scheme above). The resulting 4-[(R)-2-(6-chloro-pyridin-2-yl)-2-hydroxy-ethylamino]-piperidine-1-carboxylic acid tert-butyl ester was dechlorinated by transfer hydrogenation from ammonium formate and 10% palladium-on-carbon in 70% yield. The piperidine was then de-protected by treatment with HCl in 1,4-dioxane/methanol as described before, in quantitative yield. 3-Amino-6-[4-((R)-2-hydroxy-2-pyridin-2-yl-ethylamino)-piperidin-1-yl]-4-trifluoromethyl-thieno[2,3-b]pyridine-2-carboxylic acid amide 95.0% ee, Mp: 165–167° C. was prepared via the methods described in scheme II. ES+ 481 m/z (MH+)

3-Amino-6-[4-((S)-2-hydroxy-2-pyridin-2-yl-ethylamino)-piperidin-1-yl]-4-trifluoromethyl-thieno[2,3-b]pyridine-2-carboxylic acid amide 95.4% ee, Mp: 165–167° C. was prepared via the methods described in example 22 and scheme II. ES+ 481 m/z (MH+)

3-Amino-6-{4-[(S)-2-(6-chloro-pyridin-2-yl)-2-hydroxy-ethylamino]-piperidin-1-yl}-4-propyl-thieno[2,3-b]pyridine-2-carboxylic acid amide was prepared via the methods described in example 22 and scheme II. ES+ 489.56 m/z (MH+)

3-Amino-6-{4-[(R)-2-(6-chloro-pyridin-2-yl)-2-hydroxy-ethylamino]-piperidin-1-yl}-4-propyl-thieno[2,3-b]pyridine-2-carboxylic acid amide was prepared via the methods described in example 22 and scheme II. ES+ 489.54 m/z (MH+)

3-Amino-6-{4-[(S)-2-(6-chloro-pyridin-2-yl)-2-hydroxy-ethylamino]-piperidin-1-yl}-4-trifluoromethyl-thieno[2,3-b]pyridine-2-carboxylic acid amide amide was prepared via the methods described in example 22 and scheme II. ES+ 515.37/517.37 m/z (MH+)

3-Amino-6-{4-[(R)-2-(6-chloro-pyridin-2-yl)-2-hydroxy-ethylamino]-piperidin-1-yl}-4-trifluoromethyl-thieno[2,3-b]pyridine-2-carboxylic acid amide amide was prepared via the methods described in example 22 and scheme II. ES+ 515.33/517.33 m/z (MH+)

Example 23

3-Amino-6-{4-[(R)-2-hydroxy-2-(6-methyl-pyridin-2-yl)-ethylamino]-piperidin-1-yl}-4-trifluoromethyl-thieno[2,3-b]pyridine-2-carboxylic acid amide

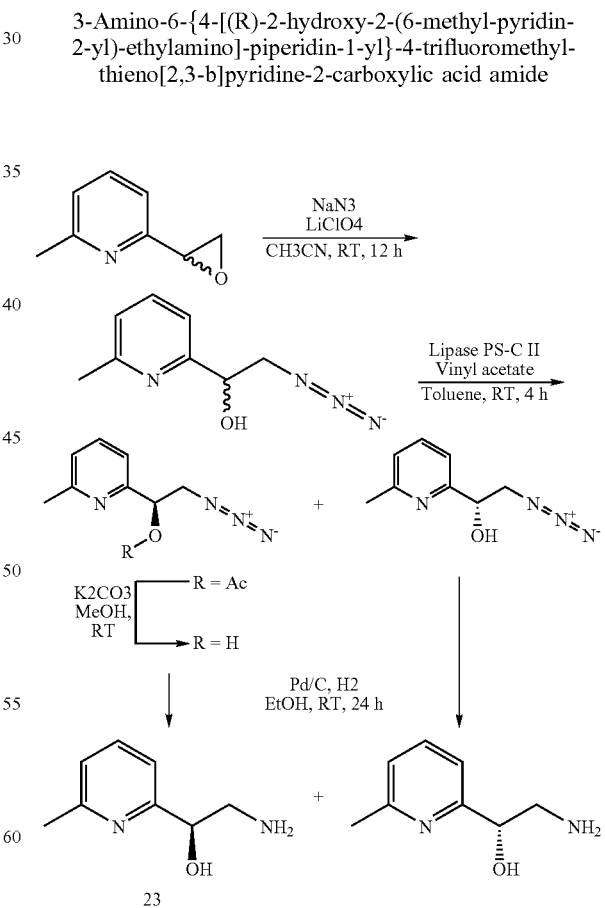

-Methyl-6-oxiranyl-pyridine (9.49 g, 70.29 mmol) was dissolved into 50 mL of CH$_3$CN. To this was added sodium azide (5.53 g, 85.00 mmol) and lithium perchlorate (9.043 g, 85.00 mmol). The mixture stirred overnight. LC-MS analysis indicated a complete reaction. Concentrated the mixture to a thick oil. Dissolved in CH$_2$Cl$_2$, applied to a SiO$_2$ column and purified (20% EtOAc/hexanes) to give 5.00 g of 2-azido-1-(6-methyl-pyridin-2-yl)-ethanol.

Dissolved 2-Azido-1-(6-methyl-pyridin-2-yl)-ethanol (4.300 g, 24.130 mmol) into 200 mL of toluene. To this was added vinyl acetate (9.22 mL, 100.00 mmol) and Lipase PS-C II (4.00 g). The mixture stirred for 4.5 h at RT and was monitored by $^1$H NMR. The reaction mixture was filtered through a bed of celite and rinsed with 100 mL of toluene. The filtrate was concentrated in vacuo. Dissolved residue into CH$_2$Cl$_2$, applied to a SiO$_2$ Column and purified (5–30% EtOAc/hexanes) to give 2.20g of acetic acid (R)-2-azido-1-(6-methyl-pyridin-2-yl)-ethyl ester and 2.11 of (S)-2-azido-1-(6-methyl-pyridin-2-yl)-ethanol, ee % >99.

Dissolved acetic acid (R)-2-azido-1-(6-methyl-pyridin-2-yl)-ethyl ester (2.20 g, 9.90 mmol) into 50 mL of MeOH. To this was added K$_2$CO$_3$ (1.50 g) and the heterogenous mixture stirred for 2 h. LC-MS analysis indicated completion of the reaction. The mixture was concentrated and 100 mL of H$_2$O was added. The mixture was extracted with 2×100 mL of CH$_2$Cl$_2$, dried with MgSO$_4$, filtered and concentrated to give 1.78 g of (R)-2-azido-1-(6-methyl-pyridin-2-yl)-ethanol. ee % >99.

Suspended 10% Pd/C (0.50g) into 100 mL EtOH under Ar. To this was added (R)-2-azido-1-(6-methyl-pyridin-2-yl)-ethanol (3.57 g, 20.74 mmol). The reaction was placed under atm. H$_2$ for 12 h. LC-MS analysis indicted some remaining azide. Recharge with H$_2$ atmospher and stir an additional 12 h. LC-MS analysis indicated complete reaction. The mixture was filtered through a bed of celite. The celite was rinsed with 100 mL of EtOH. The filtrate was concentrated to give 2.99 g of (R)-2-amino-1-(6-methyl-pyridin-2-yl)-ethanol.

3-Amino-6-{4-[(S)-2-hydroxy-2-(6-methyl-pyridin-2-yl)-ethylamino]-piperidin-1-yl}-4-trifluoromethyl-thieno[2,3-b]pyridine-2-carboxylic acid amide was prepared via the methods described in example 6 and scheme 11. ES$^+$ 495.54 m/z (MH$^+$)

3-Amino-6-{4-[(S)-2-hydroxy-2-(6-methyl-pyridin-2-yl)-ethylamino]-piperidin-1-yl}-4-trifluoromethyl-thieno[2,3-b]pyridine-2-carboxylic acid amide was prepared from (S)-2-azido-1-(6-methyl-pyridin-2-yl)-ethanol via the methods described in example 6 and scheme II. ES$^+$ 495.24 m/z (MH$^+$)

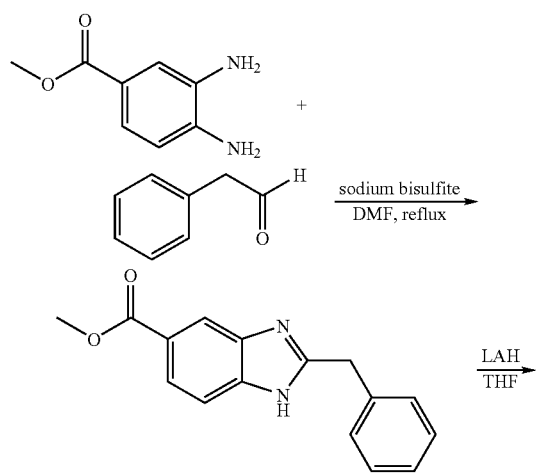

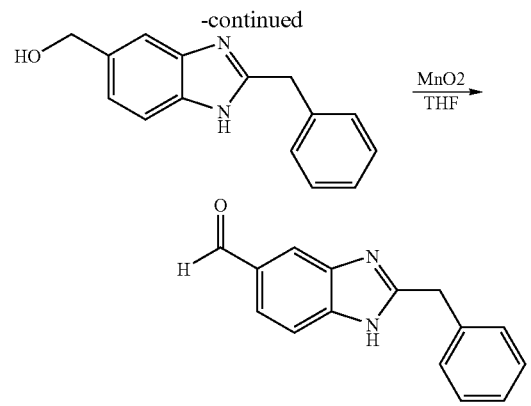

3-Amino-6-{4-[2-(2-benzyl-1H-benzoimidazol-5-yl)-2-hydroxy-ethylamino]-piperidin-1-yl}-4-trifluoromethyl-thieno[2,3-b]pyridine-2-carboxylic acid amide was prepared via the methods described in example 21, example 2 and Scheme II. ES$^+$ 610.5 m/z (MH$^+$).

3-Amino-6-(4-{2-hydroxy-2-[5-(3-methyl-3H-imidazol-4-yl)-pyridin-2-yl]-ethylamino}-piperidin-1-yl)-4-trifluoromethyl-thieno[2,3-b]pyridine-2-carboxylic acid amide. was prepared via the methods described in example 20 and Scheme II. ES$^+$ 608.4 m/z (MH$^+$). ES$^+$ 561.4 m/z (MH$^+$).

3-Amino-6-{4-[2-hydroxy-2-(6-phenyl-pyridin-3-yl)-ethylamino]-piperidin-1-yl}-4-trifluoromethyl-thieno[2,3-b]pyridine-2-carboxylic acid amide was prepared via the methods described in example 19 and Scheme II. ES$^+$ 557.5 m/z (MH$^+$).

3-Amino-6-[4-(2-[2,3']bipyridinyl-5-yl-2-hydroxy-ethylamino)-piperidin-1-yl]-4-trifluoromethyl-thieno[2,3-b]pyridine-2-carboxylic acid amide was prepared via the methods described in example 19 and Scheme II. ES$^+$ 558.5 m/z (MH$^+$).

3-Amino-6-{4-[2-hydroxy-2-(6-pyrimidin-5-yl-pyridin-3-yl)-ethylamino]-piperidin-1-yl}-4-trifluoromethyl-thieno[2,3-b]pyridine-2-carboxylic acid amide was prepared via the methods described in example 19 and Scheme II. ES$^+$ 559.5 m/z (MH$^+$).

3-Amino-6-(4-{2-hydroxy-2-[6-(2-methoxy-pyrimidin-5-yl)-pyridin-3-yl]-ethylamino}-piperidin-1-yl)-4-trifluoromethyl-thieno[2,3-b]pyridine-2-carboxylic acid amide was prepared via the methods described in example 19 and Scheme II. ES$^+$ 589.5 m/z (MH$^+$).

3-Amino-6-{4-[2-hydroxy-2-(6'-methoxy-[2,3']bipyridinyl-5-yl)-ethylamino]-piperidin-1-yl}-4-trifluoromethyl-thieno[2,3-b]pyridine-2-carboxylic acid amide was prepared via the methods described in example 19 and Scheme II. ES$^+$ 588.5 m/z (MH$^+$).

3-Amino-6-{4-[2-hydroxy-2-(6-quinolin-8-yl-pyridin-3-yl)-ethylamino]-piperidin-1-yl}-4-trifluoromethyl-thieno[2,3-b]pyridine-2-carboxylic acid amide was prepared via the methods described in example 19 and Scheme II. ES$^+$ 608.4 m/z (MH$^+$).

3-Amino-6-{4-[2-(6-bromo-pyridin-3-yl)-2-hydroxy-ethylamino]-piperidin-1-yl}-4-trifluoromethyl-thieno[2,3-b]pyridine-2-carboxylic acid amide. was prepared via the methods described in example 8 and Scheme II. ES$^+$ 608.4 m/z (MH$^+$). ES$^+$ 559.3/561.3 m/z (MH$^+$).

3-Amino-6-{4-[2-(6-carbamoylmethylsulfanyl-pyridin-3-yl)-2-hydroxy-ethylamino]-piperidin-1-yl}-4-trifluoromethyl-thieno[2,3-b]pyridine-2-carboxylic acid amide was a side product of the preceeding example ES+ 570.5 m/z (MH+).

3-Amino-6-{4-[2-hydroxy-2-(6-methoxy-pyridin-2-yl)-ethylamino]-piperidin-1-yl}-4-trifluoromethyl-thieno[2,3-b]pyridine-2-carboxylic acid amide was prepared via the methods described in example 1 and Scheme II. ES+ 511.3 m/z (MH+).

Assessment of Biological Properties

The inhibition of IKKα and IKKβ by the compounds of the present invention was determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1–54).

The reaction mixtures (60 μl) contained 20 mM HEPES pH 7.5, 10 mM $MgCl_2$, 2 mM $MnCl_2$, 100 mM NaCl, 100 μM $Na_3VO_4$, 20 mM β-glycerophosphate, 1 mM DTT, 2% DMSO, 250 nM ATP, 0.4 nM [$^{33}$P]ATP (specific activity, 3000 Ci/mmol), IκBα substrate, IKK enzyme and test compound. The reaction mixtures contained either 3.6 μg/ml IKKα and 245 μg/ml IκBα or 0.9 μg/ml IKKβ and 53 μg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 μl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 μl of $ddH_2O$ using the Packard Filtermate Harvester. Filtration plates were then air dried, supplemented with 40 μl of Microscint 20 scintillation fluid and the $^{33}$P-labeled reaction products were quantified using the Packard TopCount scintillation counter.

Compounds were tested in three-fold serial dilutions and inhibitor concentrations to achieve 50% inhibition of enzyme activity (i.e., $IC_{50}$) were derived from dose-reponse curves using SAS software (SAS Institute, Cary N.C.). A non-linear regression analysis based on the Hill equation was applied to the percent inhibition versus concentration data. In all cases, compound concentrations were verified by HPLC.

Compounds in the Table in the Detailed Description of the Invention section were all evaluated in the assay for IKKβ inhibition and had $IC_{50}$'s of about 1 μM or below.

The compounds were all also evaluated in the assay for IKKα inhibition amd had $IC_{50}$'s of about 20 μM or below.

What is claimed is:

1. A compound of formula (I):

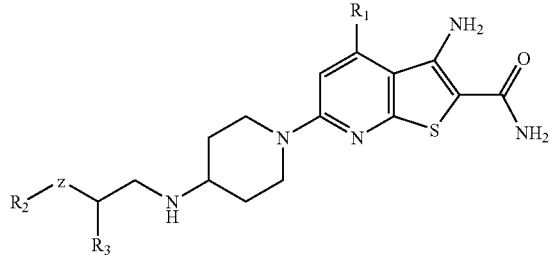

wherein:
$R_1$ is
(a) phenyl or heteroaryl selected from furanyl, thienyl, pyridyl, pyrrolyl, imidazolyl and benzofuranyl, optionally substituted with one to two $R_4$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_7(CH_2)_mO$—,
(d) $R_7OCH_2$—,
(e) $R_7(CH_2)_mNH$—,
(f) $R_7(CH_2)_p(CH=CH)_m$—,
(g) $C_{1-6}$alkyl, optionally partially or fully halogenated and optionally substituted with one to two $R_8$,
(h) $C_{1-8}$alkoxy, optionally partially or fully halogenated and optionally substituted with one to two $R_8$,
(i) $C_{1-8}$alkylS(O)$_n$—, optionally partially of fully halogenated and optionally substituted with one to two $R_8$,
(j) —$N(R_5)(R_6)$, or
(k) —C(O)NHR', wherein R' is $R_7$, pyridyl or —$CH_3$;
$R_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, substituted with one to three $R_4$;
$R_3$ is —OH or —H;
$R_4$ is chosen from, $C_{1-6}$alkoxy, hydroxy$C_{1-6}$alkyl, halogen, —CN, —$CO_2H$, —$CO_2C_{1-6}$alkyl, —$S(O)C_{1-6}$alkyl, —S(O)$_n$-p-tolyl, —$NO_2$, —OH, —$CF_3$, —$N(R_5)(R_6)$, —$NHC(O)NHC_{1-6}$alkyl, —$C(O)N(R_5)(R_6)$—, and $R_9$;
$R_5$ and $R_6$ are independently selected from H, $C_{1-6}$alkyl, —$C(O)C_{1-6}$alkyl, —$SO_2C_{1-6}$alkyl, phenyl, pyridyl, benzyl, piperidinyl, phenylethyl and $(CH_3)_3COC(O)$—;
$R_7$ is a phenyl group optionally substituted with one or two groups selected from halogen, $C_{1-6}$alkyl, —CN, —$CO_2C_{1-6}$alkyl, —$C(O)NR_5R_6$, —$SO_2NH_2$, —$NO_2$, —OH, —$NH_2$, —$CF_3$ and $C_{1-6}$alkoxy, or $R_7$ is $C_{3-6}$cycloalkyl, —$CH_2OH$, naphthalene-2-yl, naphthalene-1-yl, pyridyl or thienyl;
$R_8$ is selected from oxo, —OH, —$NR_4R_5$, —$CO_2H$ and $C_{1-6}$alkoxy;
$R_9$ is is a heteroaryl selected from the group of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl and methyl imidizolyl, carbanomethylsulfanyl, methoxypiperdinyl, methoxypyridinyl, bromopyridynyl and methoxypyrimidynyl;

m is 0 or 1;
n is 0, 1 or 2;
p is 0, 1, 2 or 3;
Z is a bond or —O—CH$_2$—;
or a pharmaceutically acceptable salt, ester, tautomer, individual isomers, and mixtures of isomers thereof.

2. The compound of claim 1 wherein:
$R_1$ is
(a) $R_7$(CH═CH)—,
(b) C$_{1-6}$alkyl optionally partially or fully halogenated;
(c) —C$_{2-3}$alkylOH,
(d) —CF$_3$,
(e) —C$_{1-6}$alkoxy, optionally partially or fully halogenated
(f) —OC$_{2-3}$alkylOH,
(g) —C$_{1-6}$alkylthio, or
(h) —C(O)NHR', wherein R' is $R_6$, pyridyl or —CH$_3$;
$R_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, benzofuranyl, benzothienyl, benzimidazolyl, benzthiazolyl, benzoxazolyl, quinolinyl, isoquinolinyl, quinazolinyl, quinoxalinyl and naphthyridinyl, substituted with one to three $R_4$;
$R_3$ is —OH or —H;
$R_4$ is chosen from C$_{1-6}$alkoxy, hydroxyC$_{1-6}$alkyl, halogen, —CN, —CO$_2$H, —CO$_2$C$_{1-6}$alkyl, —S(O)$_{n1}$C$_{1-6}$alkyl, —S(O)$_n$-p-tolyl, —NO$_2$, —OH, —CF$_3$, —N($R_5$)($R_6$), —NHC(O)NHC$_{1-6}$alkyl, —C(O)N($R_5$)($R_6$), and heteroaryl chosen from $R_9$;
$R_5$ and $R_6$ are independently selected from H, C$_{1-6}$alkyl, —C(O)C$_{1-6}$alkyl, —SO$_2$C$_{1-6}$alkyl, phenyl, pyridyl, benzyl, piperidinyl, phenylethyl and (CH$_3$)$_3$COC(O)—;
$R_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or $R_7$ is C$_{3-6}$cycloalkyl, —CH$_2$OH, naphthalene-2-yl, naphthalene-1-yl, pyridyl or thienyl;
$R_9$ is a heteroaryl selected from the group of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl and methyl imidizolyl, carbanomethylsulfanyl, methoxypiperdinyl, methoxypyridinyl, bromopyridynyl and methoxypyrimidynyl;
n is 0, 1 or 2;
Z is a bond or —O—CH$_2$—;
and a pharmaceutically acceptable salt, ester, tautomer, individual isomer, or mixtures of isomers thereof.

3. The compound of claim 1 wherein:
$R_1$ is
(a) $R_7$(CH═CH)—,
(b) C$_{1-6}$alkyl optionally partially or fully halogenated,
(c) —CF$_3$,
(d) —C$_{1-6}$alkoxy, optionally partially or fully halogenated
(e) —C$_{1-6}$alkylthio, or
(f) —C(O)NHR', wherein R' is $R_6$, pyridyl or —CH$_3$;
$R_2$ is heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, benzofuranyl, benzothienyl, benzimidazolyl, benzthiazolyl, benzoxazolyl, quinolinyl, isoquinolinyl, quinazolinyl, quinoxalinyl and naphthyridinyl substituted with one to three $R_4$;
$R_3$ is —OH;
$R_4$ is chosen from C$_{1-6}$alkoxy, hydroxyC$_{1-6}$alkyl, halogen, —CN, —CO$_2$H, —CO$_2$C$_{1-6}$alkyl, —S(O)$_1$C$_{1-6}$alkyl, —S(O)$_n$-p-tolyl, —NO$_2$, —OH, —CF$_3$, —N($R_5$)($R_6$), and —C(O)N($R_5$)($R_6$);
$R_5$ and $R_6$ are independently selected from H, C$_{1-6}$alkyl, —C(O)C$_{1-6}$alkyl, —SO$_2$C$_{1-6}$alkyl, phenyl, pyridyl, benzyl, piperidinyl, phenylethyl and (CH$_3$)$_3$COC(O)—;
$R_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or $R_7$ is C$_{3-6}$cycloalkyl, —CH$_2$OH, naphthalene-2-yl, naphthalene-1-yl, pyridyl or thienyl;
n is 0, 1 or 2;
Z is a bond or —O—CH$_2$—;
and a pharmaceutically acceptable salt, ester, tautomer, individual isomer, or and mixtures of isomers thereof.

4. The compound of claim 1 wherein:
$R_1$ is
(a) $R_7$(CH═CH)—,
(b) C$_{1-6}$alkyl optionally partially or fully halogenated,
(c) —CF$_3$,
(d) —C$_{1-6}$alkoxy, optionally partially or fully halogenated
(e) —C$_{1-6}$alkylthio, or
(f) —C(O)NHR', wherein R' is $R_6$, pyridyl or —CH$_3$;
$R_2$ is heteroaryl selected from the group consisting of, thienyl, thiazolyl, imidazolyl, pyridinyl, pyrimidinyl, pyrazinyl, indolyl, benzothienyl, benzimidazolyl, benzthiazolyl, quinolinyl and isoquinolinyl substituted with one to three $R_4$;
$R_3$ is —OH;
$R_4$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —S(O)$_n$-p-tolyl, —NO$_2$, —OH, —CF$_3$, —N($R_5$)($R_6$), and —C(O)N($R_5$)($R_6$);
$R_5$ and $R_6$ are independently selected from H, C$_{1-6}$alkyl, —C(O)C$_{1-6}$alkyl, —SO$_2$C$_{1-6}$alkyl, phenyl, pyridyl, benzyl, piperidinyl and phenylethyl;
$R_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or $R_7$ is C$_{3-6}$cycloalkyl, —CH$_2$OH, naphthalene-2-yl, naphthalene-1-yl, pyridyl or thienyl;
n is 0, 1 or 2;
Z is a bond or —O—CH$_2$—;
and pharmaceutically acceptable salts, esters, tautomers, individual isomers, and mixtures of isomers thereof.

5. The compound of claim 1 wherein:
$R_1$ is
(a) $R_7$(CH═CH)—,
(b) C$_{1-6}$alkyl optionally partially or fully halogenated
(c) —CF$_3$,
(d) —C$_{1-6}$alkoxy, optionally partially or fully halogenated
(e) —C$_{1-6}$alkylthio, or
(f) —C(O)NHR', wherein R' is $R_6$, pyridyl or —CH$_3$;

R$_2$ is heteroaryl selected from the group consisting of, 3-thienyl, 2-thiazolyl, 2-imidazolyl, 2-, 3- and 4-pyridinyl, 4-pyrimidinyl, 2-pyrazinyl, 2-indolyl, 2-benzothienyl, 2-benzimidazolyl, 2-benzthiazolyl, 2-, 3-, 4- and 6-quinolinyl and 1- and 3-isoquinolinyl; substituted with one to three R$_4$;

R$_3$ is —OH;

R$_4$ is chosen from C$_{1-6}$alkoxy, hydroxyC$_{1-6}$alkyl, halogen, —CN, —CO$_2$H, —CO$_2$C$_{1-6}$alkyl, —S(O)$_1$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

R$_5$ and R$_6$ are independently selected from H, C$_{1-6}$alkyl, —C(O)C$_{1-6}$alkyl, —SO$_2$C$_{1-6}$alkyl, phenyl, pyridyl, benzyl, piperidinyl and phenylethyl;

R$_7$ is a phenyl group optionally substituted with one or two groups selected from halogen, C$_{1-6}$alkyl, —CN, —CO$_2$C$_{1-6}$alkyl, —C(O)NR$_5$R$_6$, —SO$_2$NH$_2$, —NO$_2$, —OH, —NH$_2$, —CF$_3$ and C$_{1-6}$alkoxy, or R$_7$ is C$_{3-6}$cycloalkyl, —CH$_2$OH, naphthalene-2-yl, naphthalene-1-yl, pyridyl or thienyl;

n is 0, 1 or 2;

Z is a bond or —O—CH$_2$—;

and pharmaceutically acceptable salt, ester, tautomer, individual isomer or and mixtures of isomers thereof.

6. The compound of claim 1 wherein:

R$_1$ is
(a) C$_{1-3}$alkyl partially fluorinated,
(b) —CF$_3$, or
(c) OCH$_2$CF$_3$ R$_2$ is heteroaryl selected from the group consisting of, 3-thienyl, 2-thiazolyl, 2-imidazolyl, 2-, 3- and 4-pyridinyl, 4-pyrimidinyl, 2-pyrazinyl, 2-indolyl, 2-benzothienyl, 2-benzimidazolyl, 2-benzthiazolyl, 2-, 3-, 4- and 6-quinolinyl and 1- and 3-isoquinolinyl; substituted with one to three R$_4$;

R$_3$ is —OH;

R$_4$ is chosen from C$_{1-6}$alkoxy, hydroxyC$_{1-6}$alkyl, halogen, —CN, —CO$_2$H, —CO$_2$C$_{1-6}$alkyl, —S(O)$_1$C$_{1-6}$alkyl, —S(O)$_n$-p-tolyl, —NO$_2$, —OH, —CF$_3$, —N(R$_5$)(R$_6$), and —C(O)N(R$_5$)(R$_6$);

R$_5$ and R$_6$ are independently selected from H, C$_{1-6}$alkyl, —C(O)C$_{1-6}$alkyl, —SO$_2$C$_{1-6}$alkyl, phenyl, pyridyl, benzyl, piperidinyl and phenylethyl;

n is 0, 1 or 2;

Z is a bond;

or a pharmaceutically acceptable salt, ester, tautomer, individual isomer, or mixtures of isomers thereof.

7. A compound selected from the group consisting of:

3-Amino-6-(4-{2-hydroxy-2-[1-(toluene-4-sulfonyl)-1H-indol-2-yl]-ethylamino}-pyridine-1-yl)-4-propyl-thieno[2,3-b]pyridine-2-carboxylic acid amide;

3-Amino-6-{4-[2-(5-cyano-pyridin-2-hydroxy-ethylamino]-piperidin-1-yl}-4-propyl-thieno[2,3-b]pyridine-2-carboxylic acid amide;

3-Amino-6-{4-[2-(5-benzylcarbamoyl-pyridin-2-yl)-2-hydroxy-ethylamino]-piperidin-1-yl}-4-propyl-thieno[2,3-b]pyridine-2-carboxylic acid amide;

3-Amino-6-{4-[2-(6-cyano-pyridin-2-yl)-2-hydroxy-ethylamino]-piperidin-1-yl}-4-propyl-thieno[2,3-b]pyridine-2-carboxylic acid amide;

3-Amino-6-{4-[2-(6-carbamoyl-pyridin-2-yl)-2-hydroxy-ethylamino]-piperidin-1-yl}-4-propyl-thieno[2,3-b]pyridine-2-carboxylic acid amide;

3-Amino-6-{4-[2-hydroxy-2-(2-methylsulfanyl-pyrimidin-4-yl)-ethylamino]-piperidin-1-yl}-4-propyl-thieno[2,3-b]pyridine-2-carboxylic acid amide; and 3-Amino-6-{4-[2-hydroxy-2-(2-methylsulfanyl-pyrimidin-4-yl)-ethylamino]-piperidin-1-yl}-4-trifluoromethyl-thieno[2,3-b]pyridine-2-carboxylic acid amide.

8. A pharmaceutical composition comprising a therapeutically effective amount of a compound according to claim 1.

9. A method of treating an inflammatory disease or autoimmune condition comprising administering to a patient in need thereof a therapeutically effective amount of a compound according to claim 1 wherein said inflammatory disease or autoimmune condition is selected from the list consisting of osteoarthritis, reperfusion injury, asthma, multiple sclerosis, Guillain-Barre syndrome, Crohn's disease, ulcerative colitis, psoriasis, graft versus host disease, systemic lupus erythematosus, rheumatoid arthritis, toxic shock syndrome, insulin-dependent diabetes mellitis, acute and chronic pain, thermal injury, adult respiratory distress syndrome (ARDS), chronic obstructive pulmonary disease (COPD), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis.

10. The method of claim 9 wherein the inflammatory disease or autoimmune condition is selected from osteoarthritis, rheumatoid arthritis, Crohn's disease, ulcerative colitis, asthma, adult respiratory distress syndrome (ARDS) and chronic obstructive pulmonary disease (COPD).

11. A method of treating atherosclerosis, myocardial infarction or stroke, said method comprising administering to a patient in need of such treatment a therapeutically effective amount of a compound according to claim 1.

12. A method of making a compound of formula (I):

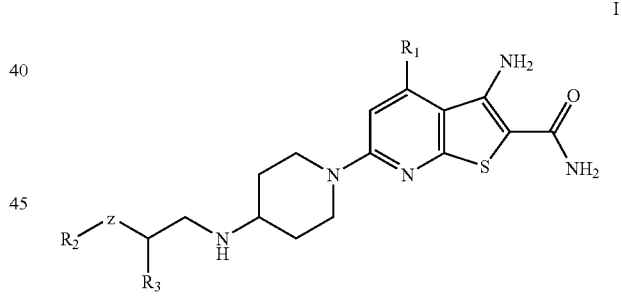

where R$_1$, R$_2$, R$_3$ and Z are as defined in claim 1, the method comprising:

reacting a compound of formula II with an amine of formula III under reductive amination conditions to provide the desired compound of formula I:

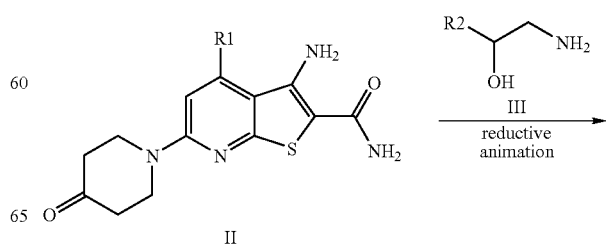

-continued
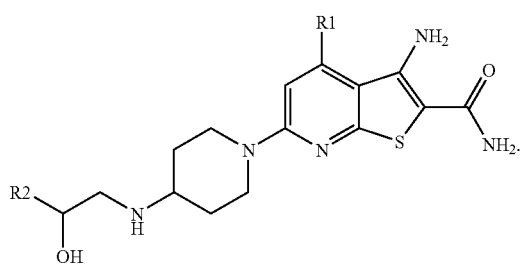
I
13. A method of making a compound of formula (I):
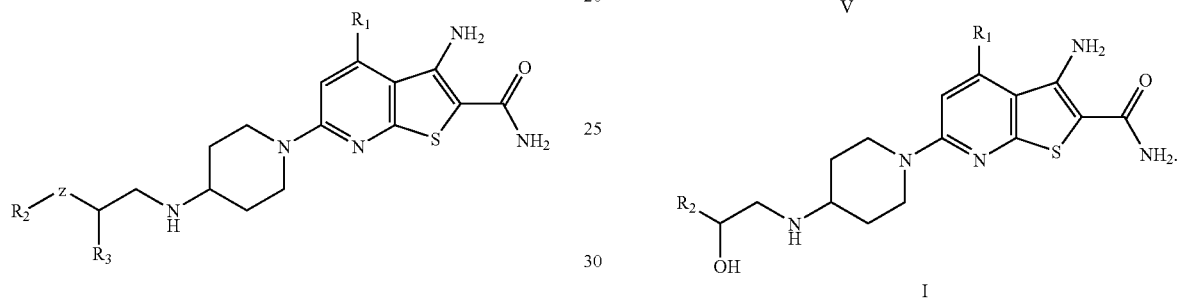
where $R_1$, $R_2$, $R_3$ and Z are as defined in claim 1, the method comprising:
reacting a compound of formula IV, wherein X is a leaving group, with a compound of formula V, in the presence of a suitable base to provide the desired compound of formula I:
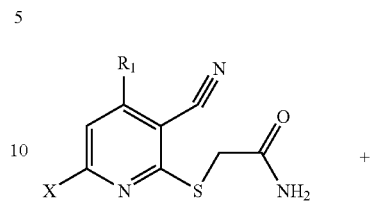
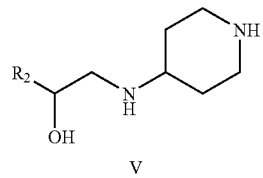
* * * * *